(12) United States Patent
Parada Valdecantos et al.

(10) Patent No.: US 8,492,093 B2
(45) Date of Patent: Jul. 23, 2013

(54) METHOD FOR THE IDENTIFICATION AND QUANTIFICATION OF MICROORGANISMS USEFUL IN BIOMINING PROCESSES

(75) Inventors: Pilar Angélica Parada Valdecantos, Santiago (CL); Katia Nicole Ehrenfeld Stolzenbach, Santiago (CL); Igor Alejandro Pacheco Cruz, Santiago (CL); Alejandro Eduardo Maass Sepúlveda, Santiago (CL); Andrés Octavio Aravena Duarte, Santiago (CL); Mauricio Alejandro Gonzalez Canales, Santiago (CL); Servet Martinez Aguilera, Santiago (CL)

(73) Assignee: Biosigma S.A., Colina (CL)

( * ) Notice: Subject to any disclaimer, the term of this patent is extended or adjusted under 35 U.S.C. 154(b) by 258 days.

(21) Appl. No.: 12/945,407

(22) Filed: Nov. 12, 2010

(65) Prior Publication Data
US 2011/0136125 A1 Jun. 9, 2011

Related U.S. Application Data

(63) Continuation-in-part of application No. 11/509,870, filed on Aug. 25, 2006, now abandoned.

(30) Foreign Application Priority Data

Aug. 26, 2005 (CL) .................................. 2179-2005

(51) Int. Cl.
  *C12Q 1/68* (2006.01)
  *C07H 21/04* (2006.01)
(52) U.S. Cl.
  USPC ..................... 435/6.12; 536/24.32; 536/24.33
(58) Field of Classification Search
  None
  See application file for complete search history.

(56) References Cited

PUBLICATIONS

Rawlings. "Characteristics and Adaptability of Iron-and Sulfur-oxidizing Microorganisms used for the Recovery of Metals from Minerals and their Concentrates." *Microbial Cell Factories* vol. 4, No. 13. 2005. pp. 1-15.
Rawlings. "Heavy Metal Mining Using Microbes." *Annu. Rev. Microbial.* vol. 56. 2002. pp. 65-91.
Labrenz et al. "Development and Application of a Real-Time PCR Approach for Quantification of Uncultured Bacteria in the Central Baltic Sea." *Applied and Environmental Microbiology.* vol. 70. No. 8 2004. pp. 4971-4979.
Burton et al. "Microbiology of acidic, geothermal springs of Montserrat: environmental rDNA analysis." *Extremophiles* vol. 4. 2000. pp. 315-320.
Dopson et al. "Chracterization of Ferroplasma Isolates and *Ferroplasma acidarmanus* sp. nov., Extream Acidophiles from Acid Mine Drainage and Industrial Bioleaching Environments." *Applied and Environmental Microbiology.* vol. 70. No. 4. 2004. pp. 2079-2088.
GenBank AY2222042 [online] Apr. 6, 2004 [retrieved on Apr. 12, 2009] retrieved from http://www.ncbi.nlm.nih.gov/nuccore/29150701?report=genbank.
Kuske et al. "Small-Scale DNA Sample Preparation Method for Field PCR Detection of Microbial Cells and Spores in Soil." *Applied and Environmental Microbiol.* vol. 64. No. 7. 1998. pp. 2463-2472.
Park et al. "Normalizatoin of soil DNA extraction for accurate quantification of target genes by real-time PCR and DGGE."*BioTechniques.* vol. 38. No. 4. 2005. pp. 579-585.
Nichols et al. "Identification of *Cryptosporidium* spp. Oocysts in United Kingdom Noncarbonated Natural Mineral Waters and Drinking Waters by Using a Modified Nested PCR-Restriction Fragment Length Polymorphism Assay." *Applied & Environ. Microbiol.* vol. 69. No. 7. 2003. pp. 4183-4189.
Rodrigues et al. "Use of both 16S rRNA and engineered functional genes with real-time PCR to quantify an engineered, PCB-degrading *Rhodococcus* in soil." *Jr. of Microbiol. Methods.* vol. 51. 2002. pp. 181-189.
Di Fiori, R. Genome Sizes [online] Jun. 25, 2007 [retrieved on Oct. 3, 2009] retrieved from: http://web.mac.com/redifiori/Russell_Di_Fiori/Molecular_Origin_of_Novelty:_Plant_Evolution_filed/Genome%20Sizes.pdf.
Ahmad, M. "Evaluating the efficacy of two *Leptothrix* specis for removal of iron." *J. of Applied Sci. Res.* vol. 4. No. 10. 2008. pp. 1230-1241.
Garcia-Moyano et al. "Evaluation of *Leptospirillum* spp. In the Rio Tino, a model of interest of biohydrometallurty." *Hydrometallurgy.* vol. 94. 2008. pp. 155-161.
Karavaiko et al. "Investigation of the phylogenetic position of aerobic, moderately thermophilic bacteria oxidizing Fe2+, SO, and sulfide minerals and affiliated to the genus *Sulfobacillus.*" *Microbiology.* vol. 69. No. 6 2000. pp. 732-735.
Karavaiko et al. Phylogenetic heterogeneity of the species *Acidithiobacillus ferrooxidans.* *Int. J. of Systematic and Evolutionary Microbiology.* vol. 53. 2003. pp. 113-119.
Reysenbach et al. "Complete and draft genome sequences of six members of the Aquificales." *Journal of Bacteriology* 191(6):1992-1993 (2009).
*Acidiphilium cryptum* JF-51nfo [online] [retrieved on May 10, 2010] retrieved from http://genome.jgi-psf.org/acicr/acicr.info.html.
Siezen et al. "Bioleaching genomics." *Molecular Biotechnology* vol. 2 No. 3. :297-303 (2009).
*Leptothrix cholodnii* SP-6, complete genome [online] [retrieved on May 10, 2010] retrieved from http://www.ncbi.nlm.nih.gov/nuccore/NC_010524 (one page).

*Primary Examiner* — Samuel Woolwine
(74) *Attorney, Agent, or Firm* — Merchant & Gould P.C.

(57) ABSTRACT

The present invention discloses a method to identify and quantify environmental microorganisms useful in biomining processes. These microorganisms are basically 10, belonging to Bacteria: *Acidiphilium* sp., *Leptospirillum* sp., *Sulfobacillus* sp., *Acidithiobacillus ferrooxidans* and *Acidithiobacillus thiooxidans*; and Archaea: *Acidianus* sp., *Ferroplasma* sp., *Metallosphaera* sp., *Sulfolobus* sp. and *Thermoplasma* sp.
The method comprises performing a PCR with specific primers designed in our laboratories for different taxons SEQ ID No. 4 to SEQ ID No.: 407. With qPCR results and other data obtained from the analyzed sample, the microorganism concentration of each analyzed taxon present in the sample is calculated using a mathematical formula.

1 Claim, 1 Drawing Sheet

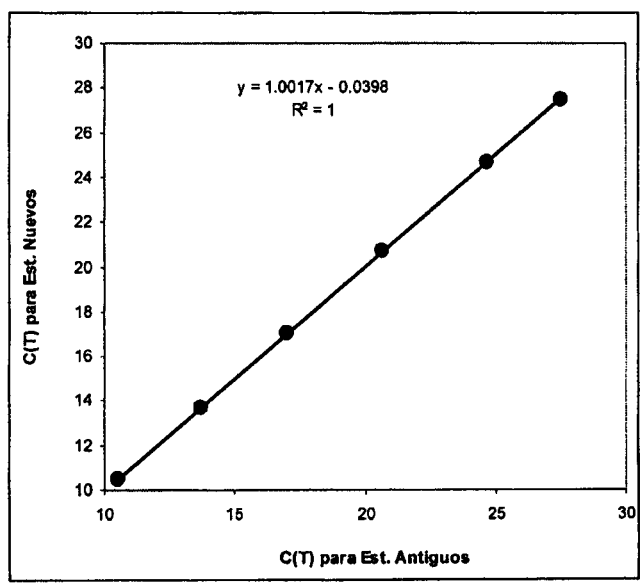
Standard DNA mixture
Diution 1:10
Dilution 1:100
Dilution 1:1000
Dilution 1:10000
Dilution 1:100000

METHOD FOR THE IDENTIFICATION AND QUANTIFICATION OF MICROORGANISMS USEFUL IN BIOMINING PROCESSES

This application is a Continuation-in-Part of U.S. Ser. No. 11/509,870, which claims benefit of Serial No. 2179-2005, filed 26 Aug. 2005 now abandoned in Chile and which applications are incorporated herein by reference. To the extent appropriate, a claim of priority is made to each of the above disclosed applications.

FIELD OF THE INVENTION

The present invention discloses a method to identify and quantify microorganisms useful in biomining processes that are present in a given sample. This method is presented as a useful tool in biomining, in every case where the present microbiological population needs to be evaluated, whether on the mineral, in solutions, in bioleaching heaps, in biomining laboratories or in any other circumstance that involves the use of such microorganisms.

BACKGROUND OF THE INVENTION

Biomining is, in general terms, the use of microorganisms for metal recovery from mineral ores. Its most traditional expression is bioleaching, but not only this process is understood as biomining, but also the monitoring and intervention in such process, as these techniques are complex and are under constant development; and also laboratory research associated to process improvement or the development of new methodologies.

Until now, bioleaching continues to be the most important process in biomining field, and is defined as a method to solubilize metals from complex matrixes in an acid medium, using direct or indirect microorganism action. The microorganisms that are useful in these processes belong to Bacteria or Archaea kingdoms, and fulfill two basic conditions: they are acidophilic and chemolithotrophic.

Microbiological Diversity in Communities Associated to Bioleaching Processes.

Various microorganisms have been described to be useful in bioleaching processes, and ten taxons could be identified among them: 3 genera and 2 species from the Bacteria kingdom, namely *Acidiphilium* sp., *Leptospirillum* sp., *Sulfobacillus* sp. genera and *Acidithiobacillus ferrooxidans* and *Acidithiobacillus thiooxidans* species, and five genera from the Archaea kingdom, namely *Acidianus* sp., *Ferroplasma* sp., *Metallosphaera* sp., *Sulfolobus* sp. and *Thermoplasma* sp. (Rawlings D E. Heavy metal mining using microbes. Annu Rev Microbiol. 2002; 56:65-91; Rawlings D E. Characteristics and adaptability of iron- and sulfur-oxidizing microorganisms used for the recovery of metals from minerals and their concentrates. Microb Cell Fact. 2005 May 6; 4(1):13).

Factors Determining Diversity and Metabolic Activity of the Microbial Community Associated to a Bioleaching Process.

Each of the above mentioned genera or species catalyzes different reactions and require in its turn different conditions to perform such reaction, which could be, for instance, aerobic or anaerobic, or could require some specific nutrient. Therefore, the environmental conditions in which a bioleaching process is performed will modify the bacterial composition of the community.

Additionally, the participation of microorganisms in a bioleaching process has been proposed to be direct and/or indirect (Rawlings D E. Characteristics and adaptability of iron- and sulfur-oxidizing microorganisms used for the recovery of metals from minerals and their concentrates. Microb Cell Fact. 2005 May 6; 4(1):13). When the action is direct, microorganisms directly oxidize the target metal or its counter-ion, in both cases liberating into the solution a target metal ion. On the other hand, when the action is indirect, the substrate of the microorganism is not the target metal neither its counter-ion, but instead chemical conditions are generated that allow the solubilization of said metal, either by acidification of the medium (e.g., by generating sulfuric acid) or by the generation of an oxidizing agent that ultimately interacts with the salt (metal and counter-ion) to be solubilized.

Regarding this aspect, it is possible that the bacterial community changes its species composition as a function of the bioleaching type being performed in different mineral samples and/or the environmental conditions in which this process is carried out.

For instance, *Acidithiobacillus* species are able to catalyze the oxidation of reduced sulfur compounds (e.g., sulfide, elemental sulfur, thionates, etc.) using oxygen as electronic acceptor and generating sulfuric acid as final product and reducing species like sulfite and thiosulfate as intermediate products, which allows the solubilization of metals associated to sulfides in the mineral. *Acidithiobacillus ferrooxidans* and *Leptospirillum ferrooxidans* are able to catalyze the oxidation of iron(II) to iron(III) using oxygen as electron acceptor, being the generated iron(III) a great oxidizing agent that can oxidize sulfides in the mineral or any other compound to be oxidized.

The usual mining practice in bioleaching processes is to leave a mineral heap in an acid medium, generally sulfuric acid, and constantly remove the acid medium to recover the metal by electrolysis. Usually heaps in which the recovery yield of the metal is efficient are obtained, and also "inefficient" heaps that have a low yield under the same operation conditions and characteristics of the substrate to be leached. The explanation to this unequal result requires the elucidation of differences in abundance and types of species in the microbiological community between both heaps. In this way, the low yield problem could be explained by the microbial community composition, and could be solved in its turn by inoculation of microorganisms that catalyze the reaction to be maintained during the bioleaching process. However, a method that enables to quantify the population of archaea and bacteria useful in biomining processes is not available up to this date.

In this patent, a method is described that solves the technical problem previously described, by designing a method to identify and quantify the presence of known microorganisms that are most relevant in biomining processes, namely the bacteria: *Acidiphilium* sp., *Leptospirillum* sp., *Sulfobacillus* sp., *Acidithiobacillus ferrooxidans* and *Acidithiobacillus thiooxidans*; and the archaea: *Acidianus* sp., *Ferroplasma* sp., *Metallosphaera* sp., *Sulfolobus* sp. and *Thermoplasma* sp.

Nested polymerase chain reaction (PCR) was the technique selected to develop this method. In this technique, a conserved genome region of the microorganisms is firstly amplified in a first PCR reaction, either on bacteria or archaea. We have selected gene 16SrDNA as the conserved region. Then, taxon-specific primers (targeting genera or species) are used to identify the presence of target microorganisms in a second PCR reaction. This second PCR reaction is performed using an equipment that allows measuring the increase of amplified product in each amplification cycle, and this information allows the quantification, by interpolation, of the original abundance of the target genome in the sample being analyzed. PCR reaction under these conditions is called quantitative PCR or qPCR.

A critical step in nested PCR technique is the design of primers for the second amplification reaction, which have to be specific for the taxon to be determined, and this aspect has a vital importance in this particular case, as the samples to which the process will be applied will usually be metagenomic samples. Therefore, it is necessary to reduce the possibility of primer unspecific hybridization to sequences present in the genome of microorganisms that have not yet been identified in the community. We have generated two fundamental tools for the design of these primers: firstly, a depurated 16SrDNA sequence database obtained from all disclosed 16SrDNA sequences; and a computational program for primer design that uses as input such database and allows designing thermodynamically stable taxon specific primers.

In the state of the art there are many examples of the application of nested PCR or qPCR, but none of them is focused to bacteria or archaea useful in biomining processes. For instance, J. L. M. Rodrigues et al (Journal of Microbiological Methods 51 (2002) 181-189) describe a qPCR to detect and quantify PCB-degrading Rhodococcus present in soil, where the 16SrDNA gene belonging to the strain with the target activity is sequenced, specific primers for said sequence are designed and qPCR reactions are carried out using said primers. In this document, a direct qPCR approach is used, instead of a nested qPCR, and it is directed to other type of microorganisms, whose handling has been widely studied and many techniques for DNA extraction are available. Another document that uses a similar approach is Patent Application EP 1 484 416, which discloses a method for the detection and quantification of pathogen bacteria and fungi present in an environment sample using qPCR. The method comprises the extraction of DNA from bacteria and fungi present in an environment sample, obtaining specific sense and antisense primers for each of the taxons to be detected and quantified; and performing qPCR reactions using a pair of primers for each of the target pathogens.

Although it is possible to enumerate documents in which microorganisms are identified and quantified using quantitative PCR techniques, as they are well known techniques in the art, the relevant point is the generation of a depurated database that allows to design specific primers and has not been implemented before for the identification of microorganisms useful in biomining processes, which is subject matter of this invention.

BRIEF DESCRIPTION OF THE DRAWING

FIG. 1 shows a standard curve obtained with dilutions of the standard DNA mixture.

DETAILED DESCRIPTION OF THE INVENTION

As has been anticipated, the invention relates to a method that allows the identification and quantification of essential microorganisms in biomining processes. These essential microorganisms belong to 10 taxons, the genera *Acidiphilium* sp., *Leptospirillum* sp., *Sulfobacillus* sp. and the species *Acidithiobacillus ferrooxidans* and *Acidithiobacillus thiooxidans* belonging to the Bacteria kingdom; and the genera *Acidianus* sp., *Ferroplasma* sp, *Metallosphaera* sp, *Sulfolobus* sp. and *Thermoplasma* sp. belonging to the Archaea kingdom.

As previously indicated, a method to identify and quantify biomining microorganisms would have applications in different industrial tasks and areas. For instance, a good tool for suitable control of bioleaching process could be the identification of microorganisms that are present in a bioleaching heap and how abundant they are, as it could be established whether is necessary to inoculate some particular microorganism or simply determine which nutrients should be added to the mixture, thus maximizing the quantity of mineral recovered in the process. The idea is to correlate the recovery efficiency of different metals present in the heap with the composition of the microbiological community in the heap, referred to the number and type of present individuals.

In general terms, samples to be analyzed in the method of the invention will be biomining samples, but this does not limit the scope of the invention, as the described method could be applied any time that one or more of the 10 taxons subject of this invention is to be identified and quantified.

In the description of the invention, all oligonucleotide sequences are written in direction 5' to 3'. Described oligonucleotides correspond to primers for PCR reactions, which can be sense or antisense primers, which could be indicated specifically (e.g., as table titles) or alternatively by including letter "F" for sense or forward primers and "R" for antisense or reverse primers in the name of the primer.

The following is the description of each of the stages of the method in detail.

DNA Preparation.

In a first stage, it is necessary to extract DNA from the sample. Different methods to extract DNA from mineral or soil samples have been disclosed and any of them can be used, considering in each case the particular nature of the sample (Appl Environ Microbiol. 2003 July; 69(7):4183-9; Biotechniques. 2005 April; 38(4):579-86). In the case that total extracted DNA (from mineral samples, being e.g. grounded chalcopyrite type 1 or other) is turbid or has a yellow or orange color, it is recommended to re-purify the sample using any existing purification technique; in our laboratories this step is performed using commercial DNA purification columns. The purified fraction is resuspended in sterile nuclease-free $H_2O$.

Once total DNA samples have been purified, total DNA present in the sample should be quantified; again, this quantification could be performed using any existing method to quantify DNA; in our laboratories it is done by spectrophotometry.

After quantifying total DNA present in the sample, an aliquot is taken and diluted to a concentration suitable for the method, which finally ranges from 0.5 to 40 ng/µl, preferably from 1 to 30 ng/µl, and most preferably from 1 to 10 ng/µl. The dilution must be done using sterile nuclease-free water.

All determinations of biomining microorganisms presented here are based in a specific recognition of a fragment of 16S rDNA genes being unique for the taxon under analysis and not presenting any cross reaction with other microorganisms. The method claims the protection of several oligonucleotide primers that specifically amplify a fragment of 16S rDNA being used as identification tag. This method is even useful when analyzing complex samples with DNA coming from different microorganisms. The method comprises a standard curve construction, a qPCR reaction with the designed specific primers and the final data transformation.

The standard curve is constructed using the specific PCR product fragment of the 16S rDNA gene produced by the designed primers in different dilutions of a mixed DNA standard sample.

PCR Reaction.

A plurality of PCR is carried out, specific for each taxon to be identified, using specific primers that amplify inside the 16S rDNA region.

In this stage it is crucial to have specific and efficient primers to amplify the target fragment that have no cross-reaction with organisms from other taxons and are thermodynamically stable, i.e. do not form hairpins, homodimers or heterodimers. The primers used in this application have been designed using the method disclosed in Patent Application CL 2102-2005 filled by Biosigma; as said method guarantees the efficiency and specificity of the designed primers.

PCR will be performed on all the reaction products. Advantageously, all reactions are carried out in duplicate, and a negative control is added.

It is important to point out that the method of the invention can be carried out to identify and quantify either all the described taxons or only one of them, and also all the possible intermediate combinations, and as a consequence every one of these options will remain being comprised inside the scope of the present invention.

The PCR is a quantitative PCR (qPCR), therefore it should be performed in a suitable thermocycler and using fluorescent reagents for qPCR. There are different commercially available alternatives, either for equipment or reagents, and any of them can be selected to carry out the present method.

For the PCR reaction the following mix is prepared:

TABLE 4

| | |
|---|---|
| Sterile nuclease-free $H_2O$ | 10.5 µl |
| Sense primer (10 µM) | 0.5 µl |
| Antisense primer (10 µM) | 0.5 µl |
| qPCR reagent | 12.5 µl |

To the mix described in Table 4, 1 µl of DNA or sterile water for the qPCR blank is added.

Primers for the PCR

As previously indicated, the requirements to be fulfilled by each primer pair selected for the PCR are: being specific for each taxon, having no cross-reactivity and being thermodynamically stable to assure primer availability in the PCR reaction. Our laboratory has developed a primer design program that gives a large amount of primers fulfilling these requirements. The method of the invention can be performed by combining any sense primer with any antisense primer designed by our program. In following tables, we give 20 sense primers and 20 antisense primers for each taxon, where any possible combination thereof could be selected for the qPCR.

(Note: the sequences of the designed primers have been compared, by using Blast from NCBI, with previously existent sequence disclosures, thus guaranteeing its novelty as primers.)

Bacteria Kingdom:

TABLE 5

*Acidiphilium* sp.

| Sense primers | Seq ID Nos. | Antisense primers | Seq ID Nos. |
|---|---|---|---|
| CAA CCA CGG TCG GGT CAG A | (SEQ ID NO: 4) | TCT CTG ACC CGA CCG TGG TT | (SEQ ID NO: 24) |
| GAC CTT AAG TTG ATG CGC T | (SEQ ID NO: 5) | TCA ACT TAA GGT CAA ACC AA | (SEQ ID NO: 25) |
| AGT CAA CCA CGG TCG GGT C | (SEQ ID NO: 6) | GGA GCT TAT TCT GCG GGT A | (SEQ ID NO: 26) |
| GGT TTG ACC TTA AGT TGA TG | (SEQ ID NO: 7) | GCA TCA ACT TAA GGT CAA AC | (SEQ ID NO: 27) |
| CTT AAG TTG ATG CGC TAA C | (SEQ ID NO: 8) | AGC GCA TCA ACT TAA GGT CA | (SEQ ID NO: 28) |
| GGC AGT CAA CCA CGG TCG G | (SEQ ID NO: 9) | GTT AGC GCA TCA ACT TAA GG | (SEQ ID NO: 29) |
| CGA TGC TGA GCT GAT CCT G | (SEQ ID NO: 10) | CCG ACC GTG GTT GAC TGC C | (SEQ ID NO: 30) |
| AAG TTG ATG CGC TAA CCG C | (SEQ ID NO: 11) | GGA TCA GCT CAG CAT CGC TG | (SEQ ID NO: 31) |
| AAA GTC GCC TAA GGA GGA G | (SEQ ID NO: 12) | TCA GGA TCA GCT CAG CAT CG | (SEQ ID NO: 32) |
| GTC GCC TAA GGA GGA GCC T | (SEQ ID NO: 13) | CGG TTA GCG CAT CAA CTT A | (SEQ ID NO: 33) |
| AAG GAG GAG CCT GCG TCT G | (SEQ ID NO: 14) | GGC TCC TCC TTA GGC GAC TT | (SEQ ID NO: 34) |
| AGG AGC CTG CGT CTG ATT A | (SEQ ID NO: 15) | GTT GAC TGC CTC CTT GCG GT | (SEQ ID NO: 35) |
| AGG AGG CAG TCA ACC ACG GT | (SEQ ID NO: 16) | TCC TCC TTA GGC GAC TTT CG | (SEQ ID NO: 36) |
| GCG AAA GTC GCC TAA GGA G | (SEQ ID NO: 17) | GTG GTT GAC TGC CTC CTT GC | (SEQ ID NO: 37) |
| GCC TAA GGA GGA GCC TGC GT | (SEQ ID NO: 18) | ACC GTG GTT GAC TGC CTC CT | (SEQ ID NO: 38) |
| GCA AGG AGG CAG TCA ACC A | (SEQ ID NO: 19) | GCA GGC TCC TCC TTA GGC GA | (SEQ ID NO: 39) |
| GCA AGT CGC TCG GGC AGT A | (SEQ ID NO: 20) | GAC GCA GGC TCC TCC TTA GG | (SEQ ID NO: 40) |
| ACC CGT AGG AAT CTA TCC T | (SEQ ID NO: 21) | TCA GAC GCA GGC TCC TCC TT | (SEQ ID NO: 41) |
| GCA CAG TCA GGC GTG AAA TA | (SEQ ID NO: 22) | TGC TAC TGC CCG AGC GAC TT | (SEQ ID NO: 42) |
| ACA CAT GCA AGT CGC TCG GG | (SEQ ID NO: 23) | TGA CCC GAC CGT GGT TGA C | (SEQ ID NO: 43) |

TABLE 6

*Leptospirillum* sp.

| Sense primers | Seq ID Nos. | Antisense primers | Seq ID Nos. |
|---|---|---|---|
| TGA GGG GAC TGC CAG CGA C | (SEQ ID NO: 44) | CTA GAC GGG TAC CTT GTT AC | (SEQ ID NO: 64) |
| TAA ATA TCC CCG ATG ACG G | (SEQ ID NO: 45) | CCG TCA TCG GGG ATA TTT A | (SEQ ID NO: 65) |
| TTG TCC GGA ACC GTG AAG GG | (SEQ ID NO: 46) | TTC ACG GTT CCG GAC AAT AT | (SEQ ID NO: 66) |
| GGA ACC GTG AAG GGT TTC G | (SEQ ID NO: 47) | CGG TTC CGG ACA ATA TTC G | (SEQ ID NO: 67) |
| CCG AAT ATT GTC CGG AAC C | (SEQ ID NO: 48) | CCC TTC ACG GTT CCG GAC AA | (SEQ ID NO: 68) |
| CGA CAG AGT TTG ATC GTG G | (SEQ ID NO: 49) | CCA CGA TCA AAC TCT GTC GA | (SEQ ID NO: 69) |
| AAT ATT GTC CGG AAC CGT G | (SEQ ID NO: 50) | AAA CCC TTC ACG GTT CCG GA | (SEQ ID NO: 70) |
| TCC GGA ACC GTG AAG GGT T | (SEQ ID NO: 51) | TTC CGG ACA ATA TTC GGT AT | (SEQ ID NO: 71) |
| AAA TCG GGC CAT CAC ACA G | (SEQ ID NO: 52) | CCG AAA CCC TTC ACG GTT CC | (SEQ ID NO: 72) |
| CAA AGA GAC TGG CAG ACT AGA | (SEQ ID NO: 53) | TAG TCT GCC AGT CTC TTT GGC | (SEQ ID NO: 73) |
| TCG GGC CAT CAC ACA GGT G | (SEQ ID NO: 54) | GCA CCT GTG TGA TGG CCC GAT | (SEQ ID NO: 74) |
| AGA GAC TGG CAG ACT AGA G | (SEQ ID NO: 55) | CTC TAG TCT GCC AGT CTC TTT | (SEQ ID NO: 75) |
| GGG GGG GCA ATA CCG AAT AGA | (SEQ ID NO: 56) | GCA GCA CCT GTG TGA TGG CCC | (SEQ ID NO: 76) |
| ATA TCA AAT AAA TAT CCC CG | (SEQ ID NO: 57) | CCT GTG TGA TGG CCC GAT TT | (SEQ ID NO: 77) |
| AAG GGA TAT CGA ATA AAT AT | (SEQ ID NO: 58) | TCT ATT CGG TAT TGC CCC CCC | (SEQ ID NO: 78) |
| CTA GAG GCT GGG AGA GGG AAG | (SEQ ID NO: 59) | CCC CTT TCG GTT CCC TAC TCG | (SEQ ID NO: 79) |
| GAC GCA GCA ACG CCA GCA GTG | (SEQ ID NO: 60) | TCC CTC TCC CAG CCT CTA GTC | (SEQ ID NO: 80) |
| AAA TAA ATA TCC CCG ATG A | (SEQ ID NO: 61) | TCG GGG ATA TTT ATT TGA T | (SEQ ID NO: 81) |
| CAG TGT GGG AAG AAG GCT TTC | (SEQ ID NO: 62) | CAT ACC TTG GGC GGC TCC CT | (SEQ ID NO: 82) |
| AAC AAG GTA CCC GTC TAG A | (SEQ ID NO: 63) | CAG CCT CTA GTC TGC CAG T | (SEQ ID NO: 83) |

TABLE 7

*Sulfobacillus* sp.

| Sense primers | Seq ID Nos. | Antisense primers | Seq ID Nos. |
|---|---|---|---|
| CGA AGG CGG TGC ACT GGC C | (SEQ ID NO: 84) | CAG TGC ACC GCC TTC GCC A | (SEQ ID NO: 104) |
| GTG GCG AAG GCG GTG CAC T | (SEQ ID NO: 85) | GGC CAG TGC ACC GCC TTC G | (SEQ ID NO: 105) |
| AGG TGT CGC GGG GGT CCA CC | (SEQ ID NO: 86) | GGT GGA CCC CCG CGA CAC C | (SEQ ID NO: 106) |
| TGT CTG TCG GGA CGA GGA C | (SEQ ID NO: 87) | GGT CCT CGT CCC GAC AGA C | (SEQ ID NO: 107) |
| GAG GGC AGG AGA GGT GCA T | (SEQ ID NO: 88) | CAT GCA CCT CTC CTG CCC TC | (SEQ ID NO: 108) |
| GTC CAC CTC GCG GTG CCG G | (SEQ ID NO: 89) | TTA GCT CCG GCA CCG CGA GG | (SEQ ID NO: 109) |
| CAC CTC GCG GTG CCG GAG C | (SEQ ID NO: 90) | GCG AGG TGG ACC CCC GCG A | (SEQ ID NO: 110) |
| GGG GGT CCA CCT CGC GGT GC | (SEQ ID NO: 91) | TGC ACC GCC TTC GCC ACC G | (SEQ ID NO: 111) |
| CTC GCG GTG CCG GAG CTA A | (SEQ ID NO: 92) | CGT ATC CAT CGT TTA CGG CG | (SEQ ID NO: 112) |
| TGT CGC GGG GGT CCA CCT C | (SEQ ID NO: 93) | GAC CCC GCG ACA CCT CGT A | (SEQ ID NO: 113) |
| GGA TAC GAG GTG TCG CGG G | (SEQ ID NO: 94) | GAG TGC GTT AGC TCC GGC AC | (SEQ ID NO: 114) |
| CGG AGC TAA CGC ACT CAG T | (SEQ ID NO: 95) | TCC ACC AGG AAT TCC ATG C | (SEQ ID NO: 115) |
| GTA AAC GAT GGA TAC GAG GT | (SEQ ID NO: 96) | GCC AGG CCA GTG CAC CGC C | (SEQ ID NO: 116) |

TABLE 7-continued

*Sulfobacillus* sp.

| Sense primers | Seq ID Nos. | Antisense primers | Seq ID Nos. |
|---|---|---|---|
| TGA GTG GGG GAT ATC GGG C | (SEQ ID NO: 97) | CCA GGA ATT CCA TGC ACC TC | (SEQ ID NO: 117) |
| TAC GAG GTG TCG CGG GGG T | (SEQ ID NO: 98) | CCT CGT ATC CAT CGT TTA CG | (SEQ ID NO: 118) |
| AGC TAA CGC ACT CAG TAT C | (SEQ ID NO: 99) | ACT GAG TGC GTT AGC TCC GG | (SEQ ID NO: 119) |
| ACG ATG GAT ACG AGG TGT CG | (SEQ ID NO: 100) | GAT ACT GAG TGC GTT AGC TC | (SEQ ID NO: 120) |
| GTG CCG GAG CTA ACG CAC TC | (SEQ ID NO: 101) | GCG ACA CCT CGT ATC CAT CG | (SEQ ID NO: 121) |
| AGG TGC ATG GAA TTC CTG GT | (SEQ ID NO: 102) | CGG GAT ACT GAG TGC GTT AG | (SEQ ID NO: 122) |
| TGC ATG GAA TTC CTG GTG GA | (SEQ ID NO: 103) | GCC CGA TAT CCC CCA CTC A | (SEQ ID NO: 123) |

TABLE 8

*Acidithiobacillus ferrooxidans*

| Sense primers | Seq ID Nos. | Antisense primers | Seq ID Nos. |
|---|---|---|---|
| CGG GTT CTA ATA CAA TCT G | (SEQ ID NO: 124) | AGA ACC CGC CTT TTC GTC CT | (SEQ ID NO: 144) |
| AGG ACG AAA AGG CGG GTT CT | (SEQ ID NO: 125) | CCG CCT TTT CGT CCT CCA C | (SEQ ID NO: 145) |
| GTG GAG GAC GAA AAG GCG G | (SEQ ID NO: 126) | CAG ATT GTA TTA GAA CCC G | (SEQ ID NO: 146) |
| ACG AAA AGG CGG GTT CTA AT | (SEQ ID NO: 127) | ATT AGA ACC CGC CTT TTC GT | (SEQ ID NO: 147) |
| AAA AGG CGG GTT CTA ATA CA | (SEQ ID NO: 128) | TGT ATT AGA ACC CGC CTT TT | (SEQ ID NO: 148) |
| AGG CGG GTT CTA ATA CAA T | (SEQ ID NO: 129) | CTC TGC AGA ATT CCG GAC AT | (SEQ ID NO: 149) |
| TTC TAA TAC AAT CTG CTG TT | (SEQ ID NO: 130) | AAC AGC AGA TTG TAT TAG AA | (SEQ ID NO: 150) |
| TAA TAC AAT CTG CTG TTG AC | (SEQ ID NO: 131) | GTC AAC AGC AGA TTG TAT TA | (SEQ ID NO: 151) |
| TAC AAT CTG CTG TTG ACG TG | (SEQ ID NO: 132) | CAC GTC AAC AGC AGA TTG TA | (SEQ ID NO: 152) |
| AAT CTG CTG TTG ACG TGA AT | (SEQ ID NO: 133) | ATT CAC GTC AAC AGC AGA TT | (SEQ ID NO: 153) |
| CGC TAA GGG AGG AGC CTA CG | (SEQ ID NO: 134) | GTA GGC TCC TCC CTT AGC GC | (SEQ ID NO: 154) |
| GCG GAC TAG AGT ATG GGA G | (SEQ ID NO: 135) | GCTC CTC CCT TAG CGC GAG | (SEQ ID NO: 155) |
| CTA GAG TAT GGG AGA GGG TG | (SEQ ID NO: 136) | CCA TAC TCT AGT CCG CCG GT | (SEQ ID NO: 156) |
| CCT CGC GCT AAG GGA GGA G | (SEQ ID NO: 137) | TCT AGT CCG CCG GTT CCA | (SEQ ID NO: 157) |
| GGC GGA CTA GAG TAT GGG AG | (SEQ ID NO: 138) | GAC GTA GGC TCC TCC CTT AG | (SEQ ID NO: 158) |
| GGG AGG AGC CTA CGT CTG AT | (SEQ ID NO: 139) | TAC TCT AGT CCG CCG GTT T | (SEQ ID NO: 159) |
| CGC GCT AAG GGA GGA GCC T | (SEQ ID NO: 140) | TCA GAC GTA GGC TCC TCC CT | (SEQ ID NO: 160) |
| CGG ACC TCG CGC TAA GGG AG | (SEQ ID NO: 141) | CCT CCC TTA GCG CGA GGT CC | (SEQ ID NO: 161) |
| GGC GGA CTA GAG TAT GGG A | (SEQ ID NO: 142) | TAG TGC GCC GGT TTC ACC C | (SEQ ID NO: 162) |
| TAA GGG AGG AGC CTA CGT CT | (SEQ ID NO: 143) | ATT GTA TTA GAA CCC GCC T | (SEQ ID NO: 163) |

TABLE 9

Acidithiobacillus thiooxidans

| Sense primers | Seq ID Nos. | Antisense primers | Seq ID Nos. |
|---|---|---|---|
| GGG AGA CGA AAA GGT AAT CG | (SEQ ID NO: 164) | ATC CCC CGG TTT CTC CCT C | (SEQ ID NO: 184) |
| AAA GTT CTT TCG GTG ACG GG | (SEQ ID NO: 165) | ATA TTA GCG ATT ACC TTT T | (SEQ ID NO: 185) |
| CGG GGA AGG TTG ATA TGT TA | (SEQ ID NO: 166) | CAA CCT TCC CCG TCA CCG AA | (SEQ ID NO: 186) |
| GAG GGA GAA ACC GGG GGA T | (SEQ ID NO: 167) | CCG AAG ATC CCC CGG TTT CT | (SEQ ID NO: 187) |
| AAT CGC TAA TAT CGG TTA C | (SEQ ID NO: 168) | CTC CAA TAG CAC GAG GTC CG | (SEQ ID NO: 188) |
| CCG GGG GAT CTT CGG ACC TC | (SEQ ID NO: 169) | ACC GAT ATT AGC GAT TAC CT | (SEQ ID NO: 189) |
| TAA TAT CGCC TGC TGT TGA C | (SEQ ID NO: 170) | AAG ATC CCC CGG TTT CTC C | (SEQ ID NO: 190) |
| TCG GTG ACG GGG AAG GTT G | (SEQ ID NO: 171) | TAT CAA CCT TCC CCG TCA CC | (SEQ ID NO: 191) |
| GGA GAA ACC GGG GGA TCT T | (SEQ ID NO: 172) | GGT TTC TCC CTC AGG ACG TA | (SEQ ID NO: 192) |
| ACG TCC TGA GGG AGA AAC CG | (SEQ ID NO: 173) | GGT CCG AAG ATC CCC CGG TT | (SEQ ID NO: 193) |
| AGA CGA AAA GGT AAT CGC TA | (SEQ ID NO: 174) | TTT CAC GAC AGA CCT AAT G | (SEQ ID NO: 194) |
| GTG ACG GGG AAG GTT GAT A | (SEQ ID NO: 175) | GTA ACC GAT ATT AGC GAT TA | (SEQ ID NO: 195) |
| GAA ACC GGG GGA TCT TCG G | (SEQ ID NO: 176) | ACA TAT CAA CCT TCC CCG TC | (SEQ ID NO: 196) |
| TCC TGA GGG AGA AAC CGG GG | (SEQ ID NO: 177) | CCC GGT TTC TCC CTC AGG AC | (SEQ ID NO: 197) |
| CGA AAA GGT AAT CGC TAA TA | (SEQ ID NO: 178) | GCG ATT ACC TTT TCG TCT CC | (SEQ ID NO: 198) |
| AAA GGT AAT CGC TAA TAT CG | (SEQ ID NO: 179) | CCC CGT CAC CGA AAG AAC TT | (SEQ ID NO: 199) |
| TCG TGG GAG ACG AAA AGG TA | (SEQ ID NO: 180) | TTA ACA TAT CAA CCT TCC CC | (SEQ ID NO: 200) |
| CGG ACC TCG TGC TAT TGG AG | (SEQ ID NO: 181) | TTA GCG ATT ACC TTT TCG TC | (SEQ ID NO: 201) |
| GTT CTT TCG GTG ACG GGG A | (SEQ ID NO: 182) | CTT CCC CGT CAC CGA AAG AA | (SEQ ID NO: 202) |
| CTT TCG GTG ACG GGG AAG G | (SEQ ID NO: 183) | ATT ACC TTT TCG TCT CCC | (SEQ ID NO: 203) |

Archaea Kingdom:

TABLE 10

Acidianus sp.

| Sense primers | Seq ID Nos. | Antisense primers | Seq ID Nos. |
|---|---|---|---|
| GGG AAA CCG TGA GGG CGC T | (SEQ ID NO: 204) | CCG CAT TGG GGA CGT TTC GCG | (SEQ ID NO: 226) |
| GCG AAA CGT CCC CAA TGC GG | (SEQ ID NO: 205) | GCG CCC TCA CGG TTT CCC GCA | (SEQ ID NO: 227) |
| CCG CAG GGA AAC CGG TAA GCC | (SEQ ID NO: 206) | CCG CAT TGG GGA CGT TTC GCG | (SEQ ID NO: 228) |
| CCC GGG AAA GGG CAG TGA TA | (SEQ ID NO: 207) | GCG CCC TCA CGG TTT CCC GCA | (SEQ ID NO: 229) |
| GGG AAA GGG CAG TGA TAC T | (SEQ ID NO: 208) | TTC CCG CAT TGG GGA CGT TTC | (SEQ ID NO: 230) |
| AAT CCG GGG CAG GCG AAG GG | (SEQ ID NO: 209) | TAG CGC CCT CAC GGT TTC CC | (SEQ ID NO: 231) |
| AGG GTA CTG GAA CGT CCC TT | (SEQ ID NO: 210) | GGC TTA CCG GTT CCC CTG CG | (SEQ ID NO: 232) |
| AAG CGT CCG GCC AGA ACG CGC | (SEQ ID NO: 211) | CTG CCC TTT CCC GGG TTG A | (SEQ ID NO: 233) |
| CGC CTA AAG GGG CAT GGG CT | (SEQ ID NO: 212) | TCA CTG CCC TTT CCC GGG T | (SEQ ID NO: 234) |
| GGC TAT TTC CCG CTC ATG CC | (SEQ ID NO: 213) | GTA TCA CTG CCC TTT CCC G | (SEQ ID NO: 235) |
| CGT ACG CCC TCG GGT AAG AGG | (SEQ ID NO: 214) | GCC CGG GTC TTT AAG CAG TG | (SEQ ID NO: 236) |
| AAC GGC CCG CCA AAC CGA TA | (SEQ ID NO: 215) | CTC CCG CCC CCT AGC CCT GCA | (SEQ ID NO: 237) |
| AGC CGG CCC TGC AAG TCA C | (SEQ ID NO: 216) | CCC GGG ATC TGT GGA TTT CGC | (SEQ ID NO: 238) |

TABLE 10-continued

Acidianus sp.

| Sense primers | Seq ID Nos. | Antisense primers | Seq ID Nos. |
|---|---|---|---|
| CAC TGC TTA AAG ACC CGG G | (SEQ ID NO: 217) | TAC CCG AGG GCG TAC GAC T | (SEQ ID NO: 239) |
| GGA GCT AAT CCG GGG CAG GCG | (SEQ ID NO: 218) | CCT CTT ACC CGA GGG CGT ACG | (SEQ ID NO: 240) |
| AAA CCG TGA GGG CGC TAC CC | (SEQ ID NO: 219) | TTC GCC TGC CCC GGA TTA G | (SEQ ID NO: 241) |
| AGG CGA AGG GTA CTG GAA CGT | (SEQ ID NO: 220) | GGC GGC AGG CTT ACC GGT TTC | (SEQ ID NO: 242) |
| ACC CCC AGT GCT CCC GAA AG | (SEQ ID NO: 221) | CGG ATT AGC TCC AGT TTC CCG | (SEQ ID NO: 243) |
| CCC TTC GCC TAA GGG GCA TG | (SEQ ID NO: 222) | GGA CGT TCC AGT ACC CTT C | (SEQ ID NO: 244) |
| GCA TGG GCT ATT CCC GCC TCA | (SEQ ID NO: 223) | CCC CGG ATT AGC TCC AGT TT | (SEQ ID NO: 245) |
| GGG AAA CCG TGA GGG CGC T | (SEQ ID NO: 224) | TAC CCT TCG CCT GCC CCG GAT | (SEQ ID NO: 246) |
| GCG AAA CGT CCC CAA TGC GG | (SEQ ID NO: 225) | CCA TGC CCC TTT AGG CGA A | (SEQ ID NO: 247) |

TABLE 11

Ferroplasma sp.

| Sense primers | Seq ID Nos. | Antisense primers | Seq ID Nos. |
|---|---|---|---|
| AGA GTC AAC CTG ACG AGC TTA | (SEQ ID NO: 248) | AAG CTC GTC AGG TTG ACT CT | (SEQ ID NO: 268) |
| GTC AAC CTG ACG AGC TTA CTC | (SEQ ID NO: 249) | GTA AGC TCG TCA GGT TGA C | (SEQ ID NO: 269) |
| TGA GAG TCA ACC TGA CGA GC | (SEQ ID NO: 250) | CGA GTA AGC TCG TCA GGT T | (SEQ ID NO: 270) |
| GAG CTT ACT CGA TAG CAG GAG | (SEQ ID NO: 251) | CTG CTA TCG AGT AAG CTC G | (SEQ ID NO: 271) |
| TTT AAT TCG AGA GGG TTA A | (SEQ ID NO: 252) | TTT AAC CCT CTC GAA TTA A | (SEQ ID NO: 272) |
| CTT ACT CGA TAG CAG GAG AGG | (SEQ ID NO: 253) | CTC CTG CTA TCG AGT AAG C | (SEQ ID NO: 273) |
| AAT CAA ATC TGA TGT CGG TGA | (SEQ ID NO: 254) | TCA GAT TTG ATT AAA CCC TC | (SEQ ID NO: 274) |
| GGT TAA ATC AAA TCT GAT G | (SEQ ID NO: 255) | ACC CTC CTC ACC GAC ATC AG | (SEQ ID NO: 275) |
| TTC GAG AGG GTT AAA TCA AAT | (SEQ ID NO: 256) | ACA TCA GAT TTG ATT AAA C | (SEQ ID NO: 276) |
| CAA ATC TGA TGT CGG TGA GGA | (SEQ ID NO: 257) | CCG ACA TCA GAT TTG ATT T | (SEQ ID NO: 277) |
| TAA ATC AAA TCT GAT GTC G | (SEQ ID NO: 258) | TGA TTT AAC CCT CTC GAA T | (SEQ ID NO: 278) |
| GAG AGG GTT AAA TCA AAT CTG | (SEQ ID NO: 259) | TCA CCG ACA TCA GAT TTG A | (SEQ ID NO: 279) |
| ATC TGA TGT CGG TGA GGA GGG | (SEQ ID NO: 260) | ATT TGA TTT AAC CCT CTC G | (SEQ ID NO: 280) |
| AAT TCG AGA GGG TTA AAT C | (SEQ ID NO: 261) | CTA CCT GAT AGG TTG CAG ACT | (SEQ ID NO: 281) |
| GAT GTC GGT GAG GAG GGT T | (SEQ ID NO: 262) | GCA CCA CCT CTC TGC TAT CG | (SEQ ID NO: 282) |
| GAG GGA TGG CAG TGT CGG A | (SEQ ID NO: 263) | ATC CCT CAA CGG AAA AGC A | (SEQ ID NO: 283) |
| TGG CCA AGA CTT TTC TCA T | (SEQ ID NO: 264) | ACA CTT AAA GTG AAC GCC CT | (SEQ ID NO: 284) |
| GAT GAG TCT GCA ACC TAT CA | (SEQ ID NO: 265) | TCG CTC CGA CAC TGC CAT C | (SEQ ID NO: 285) |
| TAG CAG AGA GGT GGT GCA TGG | (SEQ ID NO: 266) | CCG ATC TCA TGT CTT GCA GT | (SEQ ID NO: 286) |
| ACG GCC ACT GCT ATC AAG TTC | (SEQ ID NO: 267) | ATG AGA AAA GTC TTG GCC A | (SEQ ID NO: 287) |

TABLE 12

Metallosphaera sp.

| Sense primers | Seq ID Nos. | Antisense primers | Seq ID Nos. |
|---|---|---|---|
| AGG GCG TTA CCC CTA GTG C | (SEQ ID NO: 288) | GGC ACT AGG GGT AAC GCC C | (SEQ ID NO: 308) |
| TAC CCC TAG TGC CCT CGC A | (SEQ ID NO: 289) | AGA AGC TCG ACC TCC CAC CC | (SEQ ID NO: 309) |
| GCG CCC GTA GCC GGC CTG TAA | (SEQ ID NO: 290) | TAC AGG CCG GCT ACG GGC GC | (SEQ ID NO: 310) |
| GAG CTT CTC CTC CGC GAG GGG | (SEQ ID NO: 291) | AGC TCG ACC TCC CAC CCC G | (SEQ ID NO: 311) |
| GCA CCA GGC GCG AAA CGT CCC | (SEQ ID NO: 292) | CCC CTC GCG GAG GAG AAG C | (SEQ ID NO: 312) |
| GAG GTC GAG CTT CTC CTC CG | (SEQ ID NO: 293) | TGC GAG GGC ACT AGG GGT A | (SEQ ID NO: 313) |
| CCC TAG TGC CCT CGC AAG A | (SEQ ID NO: 294) | TGA CTT TAC AGG CCG GCT ACG | (SEQ ID NO: 314) |
| CCC GTA GCC GGC CTG TAA AGT | (SEQ ID NO: 295) | CAT GGC TTA GCC CTA CCC CTA | (SEQ ID NO: 315) |
| CGG GGT GGG AGG TCG AGC TTC | (SEQ ID NO: 296) | AGG AGA AGC TCG ACC TCC CA | (SEQ ID NO: 316) |
| GTC GAG CTT CTC CTC CGC GA | (SEQ ID NO: 297) | GAC GTT CCG CGC CTG GTG C | (SEQ ID NO: 317) |
| GGT GGG AGG TCG AGC TTC TCC | (SEQ ID NO: 298) | CTT TAC AGG CCG GCT ACG GG | (SEQ ID NO: 318) |
| TCG GGG TGG GAG GTC GAG C | (SEQ ID NO: 299) | TCT TGC GAG GGC ACT AGG G | (SEQ ID NO: 319) |
| GCG TTA CCC CTA GTG CCC T | (SEQ ID NO: 300) | CGG AGG AGA AGC TCG ACC TC | (SEQ ID NO: 320) |
| TAG GGG TAG GGC TAA GCC ATG | (SEQ ID NO: 301) | TCG CGG AGG AGA AGC TCG AC | (SEQ ID NO: 321) |
| CGC ACC AGG CGC GGA ACG T | (SEQ ID NO: 302) | GAG GGC ACT AGG GGT AAC G | (SEQ ID NO: 322) |
| GGG AGG TCG AGC TTC TCC T | (SEQ ID NO: 303) | ACC CCG AGG GGC AAG AGG CC | (SEQ ID NO: 323) |
| AGG TGG AGG AAT AAG CGG GG | (SEQ ID NO: 304) | GGG GTT ATC CAG ATC CCA AGG | (SEQ ID NO: 324) |
| GAA AGG TGG AGG AAT AAG C | (SEQ ID NO: 305) | GCC ACG CCC TCT TCC CGA GA | (SEQ ID NO: 325) |
| GGG AGT CGT ACG CTC TCG GGA | (SEQ ID NO: 306) | GTT ATC CAG ATC CCA AGG GC | (SEQ ID NO: 326) |
| CTA ACC TGC CCT TGG GAT CTG | (SEQ ID NO: 307) | CTT ATT CCT CCA CCT TTC TGG | (SEQ ID NO: 327) |

TABLE 13

Sulfolobus sp.

| Sense primers | Seq ID Nos. | Antisense primers | Seq ID Nos. |
|---|---|---|---|
| TAA ACC CTG CCG CAG TTG G | (SEQ ID NO: 328) | CCA ACT GCG GCA GGG TTT A | (SEQ ID NO: 348) |
| CCT TAA ACC CTG CCG CAG T | (SEQ ID NO: 329) | ACT GCG GCA GGG TTT AAG G | (SEQ ID NO: 349) |
| GTC CTG GAA CGG TTC CTC G | (SEQ ID NO: 330) | CGA GGA ACC GTT CCA GGA CTC | (SEQ ID NO: 350) |
| CTC TAC AAA GGC GGG GGA ATA | (SEQ ID NO: 331) | AAC CGT TCC AGG ACT CCT CG | (SEQ ID NO: 351) |
| CTG GAA CGG TTC CTC GCT GA | (SEQ ID NO: 332) | TCC AGG ACT CCT CGC CTA TGG | (SEQ ID NO: 352) |
| GGC GAG GAG TCC TGG AAC GGT | (SEQ ID NO: 333) | CCT TTG TAG AGC GGG GAA A | (SEQ ID NO: 353) |
| TTT CCC CGC TCT ACA AAG G | (SEQ ID NO: 334) | AGC GAG GAA CCG TTC CAG GA | (SEQ ID NO: 354) |
| TAC AAA GGC GGG GGA ATA AGC | (SEQ ID NO: 335) | CGT TCC AGG ACT CCT CGC CTA | (SEQ ID NO: 355) |
| CGC TCT ACA AAG GCG GGG G | (SEQ ID NO: 336) | CCC CCG CCT TTG TAG AGC G | (SEQ ID NO: 356) |
| ATA GGC GAG GAG TCC TGG AA | (SEQ ID NO: 337) | TTC AGC GAG GAA CCG TTC CA | (SEQ ID NO: 357) |
| CCA TAG GCG AGG AGT CCT G | (SEQ ID NO: 338) | ATT CCC CCG CCT TTG TAG A | (SEQ ID NO: 358) |
| GCT TTT CCC CGC TCT ACA A | (SEQ ID NO: 339) | TTG TAG AGC GGG GAA AAG C | (SEQ ID NO: 359) |
| GCT AAC CTA CCC TGA GGA GG | (SEQ ID NO: 340) | ATC TCC CTC CTC AGG GTA GGT | (SEQ ID NO: 360) |

TABLE 13-continued

Sulfolobus sp.

| Sense primers | Seq ID Nos. | Antisense primers | Seq ID Nos. |
|---|---|---|---|
| TCT CCC ATA GGC GAG GAG TC | (SEQ ID NO: 341) | GGG TTA TCT CCC TCC TCA G | (SEQ ID NO: 361) |
| TGG CTA ACC TAC CCT GAG G | (SEQ ID NO: 342) | TCG CCT ATG GGA GAT TAT C | (SEQ ID NO: 362) |
| ATA ATC TCC CAT AGG CGA G | (SEQ ID NO: 343) | TCA GGG TAG GTT AGC CAC GT | (SEQ ID NO: 363) |
| TGA GGA GGG AGA TAA CCC CG | (SEQ ID NO: 344) | CCT CAG GGT AGG TTA GCC A | (SEQ ID NO: 364) |
| ACA CGT GGC TAA CCT ACC CTG | (SEQ ID NO: 345) | CCG GGT TAT CTC CCT CCT | (SEQ ID NO: 365) |
| CCT GAG GAG GGA GAT AAC C | (SEQ ID NO: 346) | TCC TCG CCT ATG GGA GAT T | (SEQ ID NO: 366) |
| AAA CTG GGA TAA TCT CCC | (SEQ ID NO: 347) | CCT CCT CAG GGT AGG TTA G | (SEQ ID NO: 367) |

TABLE 14

Thermoplasma sp.

| Sense primers | Seq ID Nos. | Antisense primers | Seq ID Nos. |
|---|---|---|---|
| TCC TGA AAG GAC GAC CGG TG | (SEQ ID NO: 368) | CAG GGG CAT ATT CAC CGT AG | (SEQ ID NO: 388) |
| GGA CTG AGG GCT GTA ACT C | (SEQ ID NO: 369) | TCA GGA TTA CAG GAT TTT A | (SEQ ID NO: 389) |
| GAG GTT GAA TGT ACT TTC AGG | (SEQ ID NO: 370) | ACC CTG AAA GTA CAT TCA ACC | (SEQ ID NO: 390) |
| GGT GGC GAA AGC GTT CAA CT | (SEQ ID NO: 371) | GCC ACC GGT CGT CCT TTC A | (SEQ ID NO: 391) |
| GCC CTC ACG AAT GTG GAT T | (SEQ ID NO: 372) | CTA GTT GAA CGC TTT CGC C | (SEQ ID NO: 392) |
| ACC TCG AAA CCC GTT CGT AG | (SEQ ID NO: 373) | TCG TCC TTT CAG GAT TAC AGG | (SEQ ID NO: 393) |
| TCC GTA GTA ATC GTA GGT C | (SEQ ID NO: 374) | ACG CTT TCG CCA CCG GTC GTC | (SEQ ID NO: 394) |
| ATC CTG TAA TCC TGA AAG GAC | (SEQ ID NO: 375) | GGG TTT CGA GGT TAG CTT C | (SEQ ID NO: 395) |
| GTA GTC AGG ACT GAG GGC TG | (SEQ ID NO: 376) | CCC TCA GTC CTG ACT ACG A | (SEQ ID NO: 396) |
| AGG ACG ACC GGT GGC GAA AGC | (SEQ ID NO: 377) | CTG AAG ATT TAT AAG ACC GG | (SEQ ID NO: 397) |
| TAA CTC GCC CTC ACG AAT GT | (SEQ ID NO: 378) | TTA CAG CCC TCA GTC CTG ACT | (SEQ ID NO: 398) |
| GAA GGT GTT AAG TGG GTC A | (SEQ ID NO: 379) | AAT CCA CAT TCG TGA GGG CGA | (SEQ ID NO: 399) |
| AAA CCC GTT CGT AGT CAG GAC | (SEQ ID NO: 380) | ATG GGG TCT TGC TCG TTA T | (SEQ ID NO: 400) |
| TAC GGT GAA TAT GCC CCT GC | (SEQ ID NO: 381) | GCT GTT GAC CTA CGA TTA C | (SEQ ID NO: 401) |
| CAC TTG GTG TTG CTT CTC CGT | (SEQ ID NO: 382) | CCT ACG ATT ACT ACG GAA TCC | (SEQ ID NO: 402) |
| GAT CAC TTT TAT TGA GTC T | (SEQ ID NO: 383) | ACC CAC TTA ACA CCT TCG C | (SEQ ID NO: 403) |
| AGC ATC AGG AAT AAG GGC TG | (SEQ ID NO: 384) | CCC AAG TCT TAC AGT CTC TT | (SEQ ID NO: 404) |
| AAG ACC CCA TCT CTA ATT | (SEQ ID NO: 385) | CTA CCC TGA AGT ACA TTC A | (SEQ ID NO: 405) |
| CCG GTC TTA TAA ATC TTC A | (SEQ ID NO: 386) | CAG CCC TTA TTC CTG ATG C | (SEQ ID NO: 406) |
| ATA ACG AGC AAG ACC CCC AT | (SEQ ID NO: 387) | GGT CGT CCT TTC AGG ATT AC | (SEQ ID NO: 407) |

In PCRs a reaction is also included to quantify total bacteria or archaea present in the sample; in this case known universal primers are used for both kingdoms which are selected among the primers included in Table 15.

TABLE 15

PCR

| | | Seq ID Nos. |
|---|---|---|
| Bacteria primers | | |
| Eub27[1] F | AGA GTT TGA TCC TGG CTC AG | (SEQ ID NO: 1) |
| Univ533-F[1] | GTG CCA GCM GCC GCG GTA | (SEQ ID NO: 408) |
| Bact358-F[2] | CCT ACG GGA GGC AGC AG | (SEQ ID NO: 409) |
| Univ907-R[3] | CCG TCA ATT CCT TTG AGT T | (SEQ ID NO: 410) |
| Bact338-R[4] | GCT GCC TCC CGT AGG AGT | (SEQ ID NO: 411) |
| Bact1387-R[5] | GGG CGG WGT GTA CAA GGC | (SEQ ID NO: 412) |
| Archaea primers | | |
| Arch344-F[6] | ACG GGG CGC AGC AGG CGC GA | (SEQ ID NO: 413) |
| Univ515-F[7] | GTG CCA GCA GCC GCG GTA A | (SEQ ID NO: 414) |
| Arch958-R[8] | YCC GGC GTT GAM TCC AAT T | (SEQ ID NO: 415) |
| Arch915-R[4] | GTG CTC CCC CGC CAA TTC CT | (SEQ ID NO: 416) |
| Univ534-R[5] | ATT ACC GCG GCT GCT GG | (SEQ ID NO: 417) |

Each PCR has a specific cycle, wherein the alignment temperature changes, said temperature being specific for each used primer pair. Table 16 summarizes general conditions for all qPCR cycles.

TABLE 16

| | Step | Temperature (° C.) | Time (s) |
|---|---|---|---|
| 1 | Initial denaturation | 95 | 120 |
| 2 | Denaturation | 95 | 30 |
| 3 | Alignment | (*) | 30 |
| 4 | Extension | 72 | 40 |
| 5 | Pre-reading | 80 | 10 |
| 6 | Reading | 80 | — |
| | Repeat 40 times from step 2 to step 6 (qPCR cycle) | | |
| 7 | Denaturation curve | Between 70 and 100° C., reading each 0.2° C. | |

(*) specific temperature for each used primer pair

Denaturation curve carried out at the end of cycle 40, gives the Tm of the amplification product, and is also used to establish whether more than one amplification product is present in the amplified sample, as each would generate its own curve.

The qPCR thermocycler gives a result corresponding to DNA concentration present in each reaction, and this information is used to calculate the number of microorganisms present in the sample, which is called Q. This value is inferred by the computational program associated to the thermocycler based on: DNA concentration in calibration curve reactions and the cycle in which sample begins to amplify (or to exponentially increase its fluorescence value). The correlation between the logarithm of DNA concentration and the cycle in which amplification is observed generates a linear equation, from which DNA concentration in the analyzed samples is inferred.

Calculation of the Number of Microorganisms Present in the Sample.

Taking into account the qPCR result and other data generated during the process, the inventors have developed a mathematical formula that allows calculating the exact number of microorganisms from a given taxon present in a given sample, specially a biomining sample.

By applying the method of the invention, the number of microorganisms belonging to the taxons *Acidiphilium* sp., *Leptospirillum* sp., *Sulfobacillus* sp. *Acidithiobacillus ferrooxidans* and *Acidithiobacillus thiooxidans*, *Acidianus* sp., *Ferroplasma* sp, *Sulfolobus* sp., *Metallosphaera* sp, and/or *Thermoplasma* sp. present in a sample can be determined.

The method comprises a standard curve construction, a qPCR reaction with the designed specific primers and the final data transformation.

The standard curve is constructed using the specific PCR product fragment of the 16S rDNA gene produced by the designed primers in different dilutions of a mixed DNA standard sample.

The standard curve obtained with the dilutions of the standard DNA mixture will have a profile as shown in FIG. 1.

Whereas C(T) is the value given by the equipment that is related to the DNA concentration of the samples used with known concentration (different dilutions) of the same taxon. One standard curve has to be made for each taxon to be analyzed.

Using this information and the following equation it is possible to correlate the concentration of DNA with the number of molecules of 16S rDNA and therefore microorganisms of specific taxon. The standard curve can contain a mixture of DNAs coming from different species but even in this case one can be able to determine the number of molecules of specific specie knowing the length of the PCR product to be amplified by the specific primers and the concentration of initial DNA as it was added for the standard curve.

$$Q_{N° \text{ of molecules}} = \frac{6.023 \times 10^{23}_{mol/molec} * A_{ng/uL}}{B * 660_{g/mol} * 1 \times 10^{-9}_{ng}} \quad (1)$$

Whereas
1 bp=660 g/mol
$6.023 \times 10^{23}$ molecules or copies (Avogadro number)
A=DNA concentration in ng/uL
B=Length of the PCR product
As only A and B are variables, formula can be expressed as:

$$Q_{N° \text{ of molecules}} = 9.126 \times 10^{+11}_{molec/ng} * \frac{(A_{ng/ul})}{B} \quad (2)$$

For problem samples the qPCR reaction is performed according to the best conditions recommended for the PCR product to be amplify and the result obtained as a C(T) value is then interpolated in the standard curve to obtain the concentration of specific DNA fragment tag present in the sample. With the concentration and equation (2) one can obtain the number of molecules present in a sample as determined by the qPCR reaction.

Finally to estimate microorganisms concentration the following equation must be applied:

$$N_{Cell/(mL)or(g)} = \frac{Q_{N° \, molecules} * T_{ng}}{C_{molecules/cell} * U_{ng} * Cm_{(mL)or(g)}}. \quad (3)$$

N=Estimated Concentration of microorganisms.
Q=Number of Molecules as calculated with the standard curve using the C(T) value given by the equipment.
T=Total DNA isolated from original sample.
U=Amount of DNA used in the qPCR reaction.
C=Number of molecules or copies by genome of the specific DNA fragment detected.
Cm=Amount in "g" or "ml" of the processed sample.

In all cases number of molecules present by genome's microorganisms (C) is known either by sequence available publicly or Southern blot performed in our lab. For example, in the case of *A. ferrooxidans* it is known that the specie DSM 16786 Wenelen has only one copy of 16S rDNA gene but in the case of *Leptospirillum* DSM 17947 Yagan it is reported to have 2 copies of the 16S rDNA gene.

EXAMPLES

Example 1

Quantification of *Acidithiobacillus thiooxidans, Acidithiobacillus ferrooxidans, Leptospirillum* Sp. And *Acidiphilium* Sp. Present in a Biomining Sample Two solid samples obtained from mineral bioleaching heaps (SS-1 and SS-2) and 2 liquid samples recovered from bioleaching effluents (LS-1 and LS-2) were analyzed and total DNA was extracted from each sample.

For all solid samples a further step was necessary, a re-purification of DNA, which consisted in a sample re-purification using any existing purification technique; in our laboratories this step is performed using commercial DNA purification columns to obtain a translucent appearance in the extraction solution.

Total DNA was quantified in each sample using a Nano-Drop 1.0 spectrophotometer. Total extracted DNA nanograms (T) are shown in Table 1-1 together with the initial sample volumes ($C_m$). Registered results were:

TABLE 1-1

| Sample | T | $C_m$ |
|---|---|---|
| SS-1 | 543.2 | 100 g |
| SS-2 | 1660.4 | 20 g |
| LS-1 | 11365.2 | 45 mL |
| LS-2 | 16364.6 | 45 mL |

Each of these samples was diluted with sterile nuclease-free water in order to obtain a concentration in the range 0.5 to 30 ng/μl. Table 1-2 shows the final volume to which the DNA solution was brought and its final concentration.

TABLE 1-2

| Sample | Final volume (μl) | Concentration (ng/μl) |
|---|---|---|
| SS-1 | 70 | 7.76 |
| SS-2 | 70 | 23.72 |
| LS-1 | 421 | 27 |
| LS-2 | 545.5 | 30 |

A calibration curve was simultaneously prepared for each taxon to allow the calculation of molecule number of the target gene in experimental samples. The standard DNA was prepared for each taxon using PCR products obtained with specific primers shown in table 1-3.

TABLE 1-3

| Microorganism to be determined | Alignment temperature | Used primers | Amplify lengths (bp) |
|---|---|---|---|
| Total bacteria | 56° C. | (P.1) 533-F: 5'-GTG CCA GCA GCC GCG GTA-3' | 374 |
| | | (P.2) 907-R: 5'-CCG TCA ATT CCT TTG AGT T-3' | |
| A. ferrooxidans | 60° C. | (P.13) F: 5'-CTA GAG TAT GGG AGA GGG TG-3' | 365 |
| | | (P.6) R: 5'-CTC TGC AGA ATT CCG GAC AT-3' | |
| A. thiooxidans | 56° C. | (P.7) F: 5'-TAA TAT CGCC TGC TGT TGA C-3' | 146 |
| | | (P.11) R: 5'-TTT CAC GAC AGA CCT AAT G-3' | |
| Leptospirillum sp. | 58° C. | (P.4) F: 5'-GGA ACC GTG AAG GGT TTC G-3' | 315 |
| | | (P.2) R: 5'-CCG TCA TCG GGG ATA TTT A-3' | |

TABLE 1-3-continued

| Microorganism to be determined | Alignment temperature | Used primers | Amplify lengths (bp) |
|---|---|---|---|
| Acidiphilium sp. | 61° C. | (P.10) F: 5'-GTC GCC TAA GGA GGA GCC T-3' | 263 |
|  |  | (P.3) R: 5'-GGA GCT TAT TCT GCG GGT A-3' |  |

The PCR reaction to obtain the PCR products was carried out using as substrate the respective genomic DNA (200 ng) from each of the following microorganisms: *Acidithiobacillus thiooxidans, Acidithiobacillus ferrooxidans, Leptospirillum* sp. and *Acidiphilium* sp. The composition of PCR mix is detailed in table 1-4. The PCR product was purified using commercial DNA purification columns and concentration of the respective PCR products was determinate using Nano-Drop 1.0 spectrophotometer.

TABLE 1-4

| Reagent | 1 reaction |
|---|---|
| Sterile nuclease-free H$_2$O | 18.35 μl |
| PCR Buffer 10x | 2.5 μl |
| MgCl$_2$ (50 mM) | 1.5 μl |
| dNTPs (10 mM each) | 0.5 μl |
| Primer Forward* (10 μM) | 0.5 μl |
| Primer Reverse* (10 μM) | 0.5 μl |
| Hot Start Taq (5 U/μl) | 0.15 μl |

*Used primers are described in Table 1-3.

More specifically, the PCR products were obtained using genomic DNA from the following strains:

*A. ferrooxidans* DSM 16786;
*A. thiooxidans* DSM 504;
*Leptospirillum* sp. DSM 1931 and
*Acidiphilium acidophilus* DSMZ 700.

The number of molecules for each PCR product was calculated using the equation (2) described above.

Each standard curves was prepared using five serial dilutions containing 1×10$^8$ molecules of specific PCR products in a final volume of 20 μl, which is included in the calibration curve.

A reaction "master mix" for the quantitative PCR was prepared wherein the amount of each constituent was multiplied by the total number of reactions to be carried out in order to homogenize reagent concentrations in the different PCR tubes. The reaction mix was aliquoted in 0.2 ml tubes, using a volume of 24 μl of reaction mix per tube.

Subsequently 5 quantitative PCR were performed, one for each taxon: *Acidithiobacillus thiooxidans, Acidithiobacillus ferrooxidans, Leptospirillum* sp., *Acidiphilium* sp. and one for total bacteria, using specific primers for each of them. Sense and antisense primers were selected for the different taxons from those designed specifically by our method. Primers used for each taxon and their respective annealing temperatures are indicated in Table 1-3.

In the present Example, the following reactions were performed in duplicate:

a) Five reaction for each sample (n=4) and
b) Five reactions for each point of calibration curve (n=6), corresponding to standard DNA master mix concentrations of 1×10$^8$, 1×10$^7$, 1×10$^6$, 1×10$^5$ and 1×10$^4$ molecules, and a blank.

One quantitative PCR reaction was carried out on each sample and on standard DNA, these reactions being performed in duplicate. The qPCR was carried out using Mix SYBR Green qPCR. Each quantitative PCR reaction was carried out by duplicate which gives a total of 40 reactions per each taxon.

The quantitative PCR reaction mix for each taxon is shown in Table 1-5, where primers used are those described on Table 1-3.

TABLE 1-5

|  | 1 reaction | 20 reactions |
|---|---|---|
| Sterile nuclease-free H$_2$O | 16.1 μl | 322 μl |
| Primer 1 (10 μM) | 0.5 μl | 10 μl |
| Primer 2 (10 μM) | 0.5 μl | 10 μl |
| PCR Buffer 10x | 2.5 μl | 50 μl |
| MgCl$_2$ (50 mM) | 1.5 μl | 30 μl |
| dNTPs (10 mM each) | 2.5 μl | 50 μl |
| Hot Start Taq (5 U/μl) | 0.15 μl | 3 μl |
| SYBR Green qPCR 100x | 0.25 μl | 5 μl |

This reaction mix was homogenized and aliquoted in 20 0.2 ml tubes, which were duly labeled. To each of the tubes 1 μl of DNA sample dilution or 1 μl of sterile nuclease-free water for the blank was added.

PCR tubes containing the reaction mix and sample were shaked at vortex for 5 seconds and centrifuged for 1 minute at 2000×g, in order to homogenize and bring the reaction liquid to the bottom of the tube, respectively.

Then, the tubes with quantitative PCR reactions were subjected to temperature cycles for amplification (table 1-6). According to the microorganism to be determined, different primer pairs were used and therefore different amplification programs were used. In the following Table, amplification programs used in the different PCR reactions are shown.

TABLE 1-6

| Step |  | Temperature (° C.) | Time (s) |
|---|---|---|---|
| 1 | Initial denaturation | 95 | 120 |
| 2 | Denaturation | 95 | 30 |
| 3 | Alignment | (*) | 30 |
| 4 | Extension | 72 | 40 |
| 5 | Pre-reading | 80 | 10 |
| 6 | Reading | 80 | — |
|  | Repeat 40 times from step 2 to step 6 (qPCR cycle) | | |
| 7 | Denaturation curve | Range between 70 and 100° C., reading each 0.2° C. | |

(*) specific temperature for each used primer pair, as indicated in Table 1-3.

When the quantitative PCR is finished, all data generated by the qPCR thermocycler are stored, from standard curve is calculated the number of molecules for target gene into each sample; this data corresponds to Q and is shown in Table 1-7, wherein DNA amounts in nanograms used for each reaction are included (U).

TABLE 1-7

| Sample | Total bacteria | A. ferrooxidans | A. thiooxidans | Leptospirillum sp. | Acidiphilium sp. | U |
|---|---|---|---|---|---|---|
| | | | Q | | | |
| SS-1 | 4.85E+05 | 0.005E+05 | 0.06E+05 | 0.005E+05 | 0.45E+05 | 2.5 |
| SS-2 | 3.48E+05 | 0.047E+05 | 0.013E+05 | 0.71E+05 | 0.34E+05 | 2.5 |
| LS-1 | 3.12E+05 | 0.55E+05 | 0 | 0.006E+05 | 0 | 2.5 |
| LS-2 | 2.88E+05 | 0.82E+05 | 0 | 0.006E+05 | 0 | 2.5 |

Calculation of the Number of Microorganisms Present in the Samples

Taking into account the qPCR result and data generated during the process, the following formula described as equation (3) can be applied:

$$N_{Cell/(mL)(g)} = \frac{Q_{N° \, molecules} * T_{ng}}{C_{molecules/cell} * U_{ng} * Cm_{(mL)or(g)}}.$$

N=Estimated Concentration of microorganisms.
Q=Number of Molecules as calculated with the standard curve using the C(T) value given by the equipment.
T=Total DNA isolated from original sample.
U=Amount of DNA used in the qPCR reaction.
C=Number of molecules or copies by genome of the specific DNA fragment detected. (see table 1-8)
Cm=Amount in "g" or "ml" of the processed sample

TABLE 1-8

Number of copies of 16S rDNA gene in the genome of different taxons as described in literature or determined by Southern blot.

| Microorganisms | C |
|---|---|
| A. ferrooxidans | 1 |
| A. thiooxidans | 1 |
| Acidiphillium | 2 |
| Leptospirillum | 2 |
| Bacteria total* | 2 |

*The number of 16S rDNA copies by genome of total bacteria was estimated as an average according to our observations.

According to the previous, the following microbiological populations were determined in the analyzed samples:

TABLE 1-9

| SS-1 | |
|---|---|
| Bacteria | Mo./g of sample |
| Total bacteria | 5.27E+05 |
| A. ferrooxidans | 1.00E+03 |
| A. thiooxidans | 1.29E+04 |
| Leptospirillum sp. | 5.25E+02 |
| Acidiphilium sp. | 4.94E+04 |

TABLE 1-10

| SS-2 | |
|---|---|
| Bacteria | Mo./g of sample |
| Total bacteria | 5.78E+06 |
| A. ferrooxidans | 1.55E+05 |

TABLE 1-10-continued

| SS-2 | |
|---|---|
| Bacteria | Mo./g of sample |
| A. thiooxidans | 4.15E+04 |
| Leptospirillum sp. | 1.17E+06 |
| Acidiphilium sp. | 5.71E+05 |

TABLE 1-11

| LS-1 | |
|---|---|
| Bacteria | Mo./ml of sample |
| Total bacteria | 1.57E+07 |
| A. ferrooxidans | 5.61E+06 |
| A. thiooxidans | 0.00E+00 |
| Leptospirillum sp. | 3.02E+04 |
| Acidiphilium sp. | 0.00E+00 |

TABLE 1-12

| LS-2 | |
|---|---|
| Bacteria | Mo./ml of sample |
| Total bacteria | 2.09E+07 |
| A. ferrooxidans | 1.19E+07 |
| A. thiooxidans | 0.00E+00 |
| Leptospirillum sp. | 4.77E+04 |
| Acidiphilium sp. | 0.00E+00 |

Example 2

Quantification of *Sulfobacillus* sp., *Sulfolobus* sp., and *Ferroplasma* sp. in a Sample One sample obtained from mineral bioleaching heap (SS-3) and one liquid sample recovered from bioleaching effluents (LS-3) were analyzed and total DNA was extracted from each one.

A further DNA re-purification step was required to obtain a translucent appearance in the extraction solution.

Total DNA was quantified in each sample using a Nano-Drop 1.0 spectrophotometer. Total extracted DNA nanograms (T) are shown in Table 2-1 together with the initial sample volumes ($C_m$).

TABLE 2-1

| Sample | T | $C_m$ |
|---|---|---|
| SS-3 | 537.25 | 20 g |
| LS-3 | 16211.3 | 50 mL |

Each of these samples was diluted with sterile nuclease-free water in order to obtain a concentration in the range of 0.5 to 30 ng/μl. Table 2-2 shows the final volume to which the DNA solution was brought and its final concentration.

TABLE 2-2

| Sample | Final volume (μl) | Concentration (ng/μl) |
|---|---|---|
| SS-3 | 70 | 7.67 |
| LS-3 | 540 | 30 |

Five calibration curves were prepared for quantitative PCR that includes total Bacteria, *Sulfobacillus*, total Archaea, *Ferroplasma* and *Sulfolobus*. These calibration curves were used for calculating the molecule number of target gene in experimental samples. The standard DNA was prepared for each taxon using PCR products obtained with specific primers described in table 2-3.

TABLE 2-3

| Microorganism to be determined | Alignment temperature | Used primers | Amplify lengths (bp) |
|---|---|---|---|
| Total bacteria | 59 | (P.1) 27-F: 5'-AGA GTT TGA TCC TGG CTC AG-3' | 374 |
| | | (P.2) 338-R: 5'-GCT GCC TCC CGT AGG AGT-3' | |
| *Sulfobacillus* sp. | 66 | (P.1) F: 5'-CGA AGG CGG TGC ACT GGC C-3' | 122 |
| | | (P.3) R: 5'-GGT GGA CCC CCG CGA CAC C-3' | |
| Total archaea | 60 | (P.1) 515-F: 5'-GTG CCA GCA GCC GCG GTA A-3' | 443 |
| | | (P.2) 958-R: 5'-TCC GGC GTT GAA TCC AAT T-3' | |
| *Sulfolobus* sp. | 60 | (P.3) F: 5'-GTC CTG GAA CGG TTC CTC G-3' | 282 |
| | | (P.9) R: 5'-CCC CCG CCT TTG TAG AGC G-3' | |
| *Ferroplasma* sp. | 56 | (P.17) F: 5'-TGG CCA AGA CTT TTC TCA T-3' | 204 |
| | | (P.19) R: 5'-CCG ATC TCA TGT CTT GCA GT-3' | |

The PCR reaction to obtain the PCR products was carried out using the respective primers and as substrate the respective genomic DNA (200 ng) from each of the following microorganisms: *Sulfobacillus*, *Ferroplasma* y *Sulfolobus*. Substrate for PCR products for standard representing Total Archaea was obtained from the mix of the genomic DNA containing 100 ng of *Ferroplasma* and 100 ng of *Sulfolobus*. Substrate for PCR product representing Total Bacteria was obtained using DNA from *Sulfobacillus* (200 ng). The composition of PCR mix is detailed in table 2-4 and PCR amplification program in table 2-5. The respective PCR products were purified using commercial DNA purification columns and concentration of them was determinate using NanoDrop 1.0 spectrophotometer.

TABLE 2-4

| Reagent | 1 reaction |
|---|---|
| Sterile nuclease-free H$_2$O | 18.35 μl |
| PCR Buffer 10x | 2.5 μl |
| MgCl$_2$ (50 mM) | 1.5 μl |
| dNTPs (10 mM each) | 0.5 μl |
| Primer Forward* (10 μM) | 0.5 μl |
| Primer Reverse* (10 μM) | 0.5 μl |
| Hot Start Taq (5 U/μl) | 0.15 μl |

*Used primers are described in Table 2-3.

TABLE 2-5

| Step | Temperature (° C.) | Time (s) |
|---|---|---|
| 1. Initial denaturation | 95 | 120 |
| 2. Denaturation | 95 | 30 |
| 3. Alignment* | — | 30 |
| 4. Extension | 72 | 120 |

Wherein steps 2 to 4 are to be repeated 28 times.
*The alignment temperature used is according to pairs of primer detailed in table 2-3.

The number of molecules for each PCR product was calculated using the equation (2) described above.

Each standard curves was prepared using five serial dilutions that containing $1 \times 10^8$ molecules of specific PCR products in a final volume of 20 μl, which in its turn is included in the calibration curve.

A reaction "master mix" for the quantitative PCR was prepared wherein the amount of each constituent was multiplied by the total number of reactions to be carried out in order to homogenize reagent concentrations in the different PCR tubes. The reaction mix was aliquoted in 0.2 ml tubes, using a volume of 24 µl of reaction mix per tube.

Subsequently 5 quantitative PCR were performed, one for each taxon: Sulfobacillus, Ferroplasma, Sulfolobus, Total Bacteria and one for Total Archaea, using specific primers for each of them. Sense and antisense primers were selected for the different genera from those included in the description of the tables corresponding to each taxon. Primers used for each taxon and their respective annealing temperatures are indicated in Table 2-3.

In the present Example, the following reactions were performed in duplicate:

a) Five reaction for each sample (n=2) and
b) Five reactions for each point of calibration curve (n=6), corresponding to standard DNA master mix concentrations of 1×10$^8$, 1×10$^7$, 1×10$^6$, 1×10$^5$ and 1×10$^4$ molecules, and a blank.

One quantitative PCR reaction was carried out on each sample and on standard DNA, these reactions being performed in duplicate. The qPCR was carried out using Mix SYBR Green qPCR. Each quantitative PCR reaction was carried out by duplicate which gives a total of 16 reactions per each taxon.

The quantitative PCR reaction mix for each taxon is shown in Table 2-6, where primers are those that are corresponding according to Table 2-3.

TABLE 2-6

|  | 1 reaction | 16 reactions |
|---|---|---|
| Sterile nuclease-free H$_2$O | 16.1 µl | 257.6 µl |
| Primer 1 (10 µM) | 0.5 µl | 8 µl |
| Primer 2 (10 µM) | 0.5 µl | 8 µl |
| PCR Buffer 10x | 2.5 µl | 40 µl |
| MgCl$_2$ (50 mM) | 1.5 µl | 24 µl |
| dNTPs (10 mM each) | 2.5 µl | 40 µl |
| Hot Start Taq (5 U/µl) | 0.15 µl | 2.4 µl |
| SYBR Green qPCR 100x | 0.25 µl | 4 µl |

This reaction mix was homogenized and aliquoted in 20 0.2 ml tubes, which were duly labeled. To each of the tubes 1 µl of DNA sample dilution or 1 µl of sterile nuclease-free water for the blank was added.

PCR tubes containing the reaction mix and sample were shaked at vortex for 5 seconds and centrifuged for 1 minute at 2000×g, in order to homogenize and bring the reaction liquid to the bottom of the tube, respectively.

Then, the tubes with quantitative PCR reactions were subjected to temperature cycles for amplification (table 2-7). According to the microorganism to be determined, different primer pairs were used and therefore different amplification programs were used. In the following Table, amplification programs used in the different PCR reactions are shown.

TABLE 2-7

| Step |  | Temperature (° C.) | Time (s) |
|---|---|---|---|
| 1 | Initial denaturation | 95 | 120 |
| 2 | Denaturation | 95 | 30 |
| 3 | Alignment | (*) | 30 |
| 4 | Extension | 72 | 40 |
| 5 | Pre-reading | 80 | 10 |
| 6 | Reading | 80 | — |
|  | Repeat 40 times from step 2 to step 6 (qPCR cycle) | | |
| 7 | Denaturation curve | Between 70 and 100° C., reading each 0.2° C. | |

(*) specific temperature for each used primer pair, as indicated in Table 2-3.

When the quantitative PCR is finished, all data generated by the qPCR thermocycler are stored, from standard curve is calculated the number of molecules for target gene into each sample; this data corresponds to Q and is shown in Table 2-8, wherein DNA amounts in nanograms used for each reaction are included (U).

TABLE 2-8

| | Q | | | | | |
|---|---|---|---|---|---|---|
| Sample | Total bacteria | Sulfobacillus sp. | Total archaea | Sulfolobus sp. | Ferroplasma sp | U |
| SS-3 | 5.76E+05 | 0.14E+05 | 1.61E+05 | 0 | 0.028E+05 | 2.5 |
| LS-3 | 16.4E+05 | 0.018E+05 | 16.8E+05 | 0.27E+05 | 4.75E+05 | 2 |

Calculation of the Number of Microorganisms Present in the Sample

Taking into account the qPCR result and data generated during the process, the following formula described as equation (3) can be applied:

$$Q_{N° \text{ of molecules}} = \frac{6.023 \times 10^{23}_{mol/molec} * A_{ng/uL}}{B * 660_{g/mol} * 1 \times 10^{-9}_{ng}} \quad (4)$$

N=Estimated Concentration of microorganisms.
Q=Number of Molecules as calculated with the standard curve using the C(T) value given by the equipment.
T=Total DNA isolated from original sample.
U=Amount of DNA used in the qPCR reaction.
C=Number of molecules or copies by genome of the specific DNA fragment detected. (see table 1-8)
Cm=Amount in "g" or "ml" of the processed sample

TABLE 2-9

| Number of copies of 16S rDNA gene in the genome of different taxas | |
|---|---|
| Microorganisms | C |
| Bacteria total* | 2 |
| Sulfobacillus | 1 |
| Archaea total* | 2 |
| Feroplasma | 1 |
| Sulfolobus sp. | 1 |

*The number of 16S rDNA of bacteria total and archaea total was estimated as average according our observations.

According to this, the following microbiological populations were determined in the analyzed samples:

TABLE 2-10

| SS-3 | |
|---|---|
| Microorganism | Mo./g of sample |
| Total bacteria | 3.09E+06 |
| *Sulfobacillus* sp. | 7.72E+04 |
| Total archaea | 8.65E+05 |
| *Sulfolobus* sp. | 0 |
| *Ferroplasma* sp. | 3.02E+04 |

TABLE 2-11

| LS-3 | |
|---|---|
| Microorganism | Mo./ml of sample |
| Total bacteria | 1.06E+08 |
| *Sulfobacillus* sp. | 1.18E+05 |
| Total archaea | 1.09E+08 |
| *Sulfolobus* sp. | 3.53E+06 |
| *Ferroplasma* sp. | 6.16E+07 |

What is claimed is:

1. Method to identify and quantify environmental microorganisms useful in biomining processes, wherein said method comprises the steps of:
   (a) extracting DNA from a sample;
   (b) quantifying the extracted DNA;
   (c) performing a quantitative PCR (qPCR) technique, using said DNA sample, and specific primers selected from SEQ ID No. 4 to SEQ ID No. 407 for each taxon to be determined, where taxons are selected from:
      i. Bacteria: *Acidiphilium* sp., *Leptospirillum* sp., *Sulfobacillus* sp., *Acidithiobacillus ferrooxidans* and *Acidithiobacillus thiooxidans*; and
      ii. Archaea: *Acidianus* sp., *Ferroplasma* sp, *Metallosphaera* sp, *Sulfolobus* sp. and *Thermoplasma* sp.;
   (d) calculating the number of microorganisms in the sample that belong to each of the analyzed taxons according to formula (3)

$$N_{Cell/(mL)\,or\,(g)} = \frac{Q_{N°\,molecules} * T_{ng}}{C_{molecules/cell} * U_{ng} * Cm_{(mL)\,or\,(g)}} \quad (3)$$

wherein:

N=Estimated Concentration of microorganisms;

Q=Number of molecules of taxon specific DNA input in the qPCR as determined by said qPCR;

T=Total DNA isolated from original sample;

U=Amount of DNA used in the qPCR reaction;

C=Number of molecules or copies by genome of the specific DNA fragment detected; and Cm=Amount in "g" or "ml" of the processed sample.

* * * * *

SEQUENCE LISTING

<160> NUMBER OF SEQ ID NOS: 417

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
agagtttgat cctggctcag                           20

<210> SEQ ID NO 2
<211> LENGTH: 19
<212> TYPE: DNA
<213> ORGANISM: Artificial Sequence
<220> FEATURE:
<223> OTHER INFORMATION: PCR primer

<400> SEQUENCE: 2
ggttaccttg ttacgactt                            19

<210> SEQ ID NO 3
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (14)..(14)
<223> OTHER INFORMATION: n is c or t

<400> SEQUENCE: 3
ttccggttga tccngccgga                           20

<210> SEQ ID NO 4
<211> LENGTH: 19
<212> TYPE: DNA
<213> ORGANISM: Artificial Sequence
<220> FEATURE:
<223> OTHER INFORMATION: Sense primer

<400> SEQUENCE: 4
caaccacggt cgggtcaga                            19

<210> SEQ ID NO 5
<211> LENGTH: 19
<212> TYPE: DNA
<213> ORGANISM: Artificial Sequence
<220> FEATURE:
<223> OTHER INFORMATION: Sense primer

<400> SEQUENCE: 5
gaccttaagt tgatgcgct                                              19

<210> SEQ ID NO 6
<211> LENGTH: 19
<212> TYPE: DNA
<213> ORGANISM: Artificial Sequence
<220> FEATURE:
<223> OTHER INFORMATION: Sense primer

<400> SEQUENCE: 6
agtcaaccac ggtcgggtc                                              19

<210> SEQ ID NO 7
<211> LENGTH: 20
<212> TYPE: DNA
<213> ORGANISM: Artificial Sequence
<220> FEATURE:
<223> OTHER INFORMATION: Sense primer

<400> SEQUENCE: 7
ggtttgacct taagttgatg                                             20

<210> SEQ ID NO 8
<211> LENGTH: 19
<212> TYPE: DNA
<213> ORGANISM: Artificial Sequence
<220> FEATURE:
<223> OTHER INFORMATION: Sense primer

<400> SEQUENCE: 8
cttaagttga tgcgctaac                                              19

<210> SEQ ID NO 9
<211> LENGTH: 19
<212> TYPE: DNA
<213> ORGANISM: Artificial Sequence
<220> FEATURE:
<223> OTHER INFORMATION: Sense primer

<400> SEQUENCE: 9
ggcagtcaac cacggtcgg                                              19

<210> SEQ ID NO 10
<211> LENGTH: 19
<212> TYPE: DNA
<213> ORGANISM: Artificial Sequence
<220> FEATURE:
<223> OTHER INFORMATION: Sense primer

<400> SEQUENCE: 10
cgatgctgag ctgatcctg                                              19

<210> SEQ ID NO 11
<211> LENGTH: 19
<212> TYPE: DNA
<213> ORGANISM: Artificial Sequence
<220> FEATURE:
<223> OTHER INFORMATION: Sense primer

<400> SEQUENCE: 11
aagttgatgc gctaaccgc                                              19

<210> SEQ ID NO 12
<211> LENGTH: 19
<212> TYPE: DNA
<213> ORGANISM: Artificial Sequence

```
<220> FEATURE:
<223> OTHER INFORMATION: Sense primer

<400> SEQUENCE: 12
aaagtcgcct aaggaggag                                               19

<210> SEQ ID NO 13
<211> LENGTH: 19
<212> TYPE: DNA
<213> ORGANISM: Artificial Sequence
<220> FEATURE:
<223> OTHER INFORMATION: Sense primer

<400> SEQUENCE: 13
gtcgcctaag gaggagcct                                               19

<210> SEQ ID NO 14
<211> LENGTH: 19
<212> TYPE: DNA
<213> ORGANISM: Artificial Sequence
<220> FEATURE:
<223> OTHER INFORMATION: Sense primer

<400> SEQUENCE: 14
aaggaggagc ctgcgtctg                                               19

<210> SEQ ID NO 15
<211> LENGTH: 19
<212> TYPE: DNA
<213> ORGANISM: Artificial Sequence
<220> FEATURE:
<223> OTHER INFORMATION: Sense primer

<400> SEQUENCE: 15
aggagcctgc gtctgatta                                               19

<210> SEQ ID NO 16
<211> LENGTH: 20
<212> TYPE: DNA
<213> ORGANISM: Artificial Sequence
<220> FEATURE:
<223> OTHER INFORMATION: Sense primer

<400> SEQUENCE: 16
aggaggcagt caaccacggt                                              20

<210> SEQ ID NO 17
<211> LENGTH: 19
<212> TYPE: DNA
<213> ORGANISM: Artificial Sequence
<220> FEATURE:
<223> OTHER INFORMATION: Sense primer

<400> SEQUENCE: 17
gcgaaagtcg cctaaggag                                               19

<210> SEQ ID NO 18
<211> LENGTH: 20
<212> TYPE: DNA
<213> ORGANISM: Artificial Sequence
<220> FEATURE:
<223> OTHER INFORMATION: Sense primer

<400> SEQUENCE: 18
gcctaaggag gagcctgcgt                                              20
```

```
<210> SEQ ID NO 19
<211> LENGTH: 19
<212> TYPE: DNA
<213> ORGANISM: Artificial Sequence
<220> FEATURE:
<223> OTHER INFORMATION: Sense primer

<400> SEQUENCE: 19
gcaaggaggc agtcaacca                                                   19

<210> SEQ ID NO 20
<211> LENGTH: 19
<212> TYPE: DNA
<213> ORGANISM: Artificial Sequence
<220> FEATURE:
<223> OTHER INFORMATION: Sense primer

<400> SEQUENCE: 20
gcaagtcgct cgggcagta                                                   19

<210> SEQ ID NO 21
<211> LENGTH: 19
<212> TYPE: DNA
<213> ORGANISM: Artificial Sequence
<220> FEATURE:
<223> OTHER INFORMATION: Sense primer

<400> SEQUENCE: 21
acccgtagga atctatcct                                                   19

<210> SEQ ID NO 22
<211> LENGTH: 20
<212> TYPE: DNA
<213> ORGANISM: Artificial Sequence
<220> FEATURE:
<223> OTHER INFORMATION: Sense primer

<400> SEQUENCE: 22
gcacagtcag gcgtgaaata                                                  20

<210> SEQ ID NO 23
<211> LENGTH: 20
<212> TYPE: DNA
<213> ORGANISM: Artificial Sequence
<220> FEATURE:
<223> OTHER INFORMATION: Sense primer

<400> SEQUENCE: 23
acacatgcaa gtcgctcggg                                                  20

<210> SEQ ID NO 24
<211> LENGTH: 20
<212> TYPE: DNA
<213> ORGANISM: Artificial Sequence
<220> FEATURE:
<223> OTHER INFORMATION: Antisense primer

<400> SEQUENCE: 24
tctctgaccc gaccgtggtt                                                  20

<210> SEQ ID NO 25
<211> LENGTH: 20
<212> TYPE: DNA
<213> ORGANISM: Artificial Sequence
<220> FEATURE:
<223> OTHER INFORMATION: Antisense primer

<400> SEQUENCE: 25
```
tcaacttaag gtcaaaccaa             20

<210> SEQ ID NO 26
<211> LENGTH: 19
<212> TYPE: DNA
<213> ORGANISM: Artificial Sequence
<220> FEATURE:
<223> OTHER INFORMATION: Antisense primer

<400> SEQUENCE: 26
ggagcttatt ctgcgggta              19

<210> SEQ ID NO 27
<211> LENGTH: 20
<212> TYPE: DNA
<213> ORGANISM: Artificial Sequence
<220> FEATURE:
<223> OTHER INFORMATION: Antisense primer

<400> SEQUENCE: 27
gcatcaactt aaggtcaaac             20

<210> SEQ ID NO 28
<211> LENGTH: 20
<212> TYPE: DNA
<213> ORGANISM: Artificial Sequence
<220> FEATURE:
<223> OTHER INFORMATION: Antisense primer

<400> SEQUENCE: 28
agcgcatcaa cttaaggtca             20

<210> SEQ ID NO 29
<211> LENGTH: 20
<212> TYPE: DNA
<213> ORGANISM: Artificial Sequence
<220> FEATURE:
<223> OTHER INFORMATION: Antisense primer

<400> SEQUENCE: 29
gttagcgcat caacttaagg             20

<210> SEQ ID NO 30
<211> LENGTH: 19
<212> TYPE: DNA
<213> ORGANISM: Artificial Sequence
<220> FEATURE:
<223> OTHER INFORMATION: Antisense primer

<400> SEQUENCE: 30
ccgaccgtgg ttgactgcc              19

<210> SEQ ID NO 31
<211> LENGTH: 20
<212> TYPE: DNA
<213> ORGANISM: Artificial Sequence
<220> FEATURE:
<223> OTHER INFORMATION: Antisense primer

<400> SEQUENCE: 31
ggatcagctc agcatcgctg             20

<210> SEQ ID NO 32
<211> LENGTH: 20
<212> TYPE: DNA
<213> ORGANISM: Artificial Sequence

```
<220> FEATURE:
<223> OTHER INFORMATION: Antisense primer

<400> SEQUENCE: 32
tcaggatcag ctcagcatcg                                               20

<210> SEQ ID NO 33
<211> LENGTH: 19
<212> TYPE: DNA
<213> ORGANISM: Artificial Sequence
<220> FEATURE:
<223> OTHER INFORMATION: Antisense primer

<400> SEQUENCE: 33
cggttagcgc atcaactta                                                19

<210> SEQ ID NO 34
<211> LENGTH: 20
<212> TYPE: DNA
<213> ORGANISM: Artificial Sequence
<220> FEATURE:
<223> OTHER INFORMATION: Antisense primer

<400> SEQUENCE: 34
ggctcctcct taggcgactt                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense primer

<400> SEQUENCE: 35
gttgactgcc tccttgcggt                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense primer

<400> SEQUENCE: 36
tcctccttag gcgactttcg                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense primer

<400> SEQUENCE: 37
gtggttgact gcctccttgc                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense primer

<400> SEQUENCE: 38
accgtggttg actgcctcct                                               20
```

<210> SEQ ID NO 39
<211> LENGTH: 20
<212> TYPE: DNA
<213> ORGANISM: Artificial Sequence
<220> FEATURE:
<223> OTHER INFORMATION: Antisense primer

<400> SEQUENCE: 39
gcaggctcct ccttaggcga                                          20

<210> SEQ ID NO 40
<211> LENGTH: 20
<212> TYPE: DNA
<213> ORGANISM: Artificial Sequence
<220> FEATURE:
<223> OTHER INFORMATION: Antisense primer

<400> SEQUENCE: 40
gacgcaggct cctccttagg                                          20

<210> SEQ ID NO 41
<211> LENGTH: 20
<212> TYPE: DNA
<213> ORGANISM: Artificial Sequence
<220> FEATURE:
<223> OTHER INFORMATION: Antisense primer

<400> SEQUENCE: 41
tcagacgcag gctcctcctt                                          20

<210> SEQ ID NO 42
<211> LENGTH: 20
<212> TYPE: DNA
<213> ORGANISM: Artificial Sequence
<220> FEATURE:
<223> OTHER INFORMATION: Antisense primer

<400> SEQUENCE: 42
tgctactgcc cgagcgactt                                          20

<210> SEQ ID NO 43
<211> LENGTH: 19
<212> TYPE: DNA
<213> ORGANISM: Artificial Sequence
<220> FEATURE:
<223> OTHER INFORMATION: Antisense primer

<400> SEQUENCE: 43
tgacccgacc gtggttgac                                           19

<210> SEQ ID NO 44
<211> LENGTH: 19
<212> TYPE: DNA
<213> ORGANISM: Artificial Sequence
<220> FEATURE:
<223> OTHER INFORMATION: Sense primer

<400> SEQUENCE: 44
tgaggggact gccagcgac                                           19

<210> SEQ ID NO 45
<211> LENGTH: 19
<212> TYPE: DNA
<213> ORGANISM: Artificial Sequence
<220> FEATURE:
<223> OTHER INFORMATION: Sense primer

<400> SEQUENCE: 45

-continued taaatatccc cgatgacgg 19

<210> SEQ ID NO 46
<211> LENGTH: 20
<212> TYPE: DNA
<213> ORGANISM: Artificial Sequence
<220> FEATURE:
<223> OTHER INFORMATION: Sense primer

<400> SEQUENCE: 46
ttgtccggaa ccgtgaaggg 20

<210> SEQ ID NO 47
<211> LENGTH: 19
<212> TYPE: DNA
<213> ORGANISM: Artificial Sequence
<220> FEATURE:
<223> OTHER INFORMATION: Sense primer

<400> SEQUENCE: 47
ggaaccgtga agggtttcg 19

<210> SEQ ID NO 48
<211> LENGTH: 19
<212> TYPE: DNA
<213> ORGANISM: Artificial Sequence
<220> FEATURE:
<223> OTHER INFORMATION: Sense primer

<400> SEQUENCE: 48
ccgaatattg tccggaacc 19

<210> SEQ ID NO 49
<211> LENGTH: 19
<212> TYPE: DNA
<213> ORGANISM: Artificial Sequence
<220> FEATURE:
<223> OTHER INFORMATION: Sense primer

<400> SEQUENCE: 49
cgacagagtt tgatcgtgg 19

<210> SEQ ID NO 50
<211> LENGTH: 19
<212> TYPE: DNA
<213> ORGANISM: Artificial Sequence
<220> FEATURE:
<223> OTHER INFORMATION: Sense primer

<400> SEQUENCE: 50
aatattgtcc ggaaccgtg 19

<210> SEQ ID NO 51
<211> LENGTH: 19
<212> TYPE: DNA
<213> ORGANISM: Artificial Sequence
<220> FEATURE:
<223> OTHER INFORMATION: Sense primer

<400> SEQUENCE: 51
tccggaaccg tgaagggtt 19

<210> SEQ ID NO 52
<211> LENGTH: 19
<212> TYPE: DNA
<213> ORGANISM: Artificial Sequence

```
<220> FEATURE:
<223> OTHER INFORMATION: Sense primer

<400> SEQUENCE: 52
aaatcgggcc atcacacag                                                    19

<210> SEQ ID NO 53
<211> LENGTH: 21
<212> TYPE: DNA
<213> ORGANISM: Artificial Sequence
<220> FEATURE:
<223> OTHER INFORMATION: Sense primer

<400> SEQUENCE: 53
caaagagact ggcagactag a                                                 21

<210> SEQ ID NO 54
<211> LENGTH: 19
<212> TYPE: DNA
<213> ORGANISM: Artificial Sequence
<220> FEATURE:
<223> OTHER INFORMATION: Sense primer

<400> SEQUENCE: 54
tcgggccatc acacaggtg                                                    19

<210> SEQ ID NO 55
<211> LENGTH: 19
<212> TYPE: DNA
<213> ORGANISM: Artificial Sequence
<220> FEATURE:
<223> OTHER INFORMATION: Sense primer

<400> SEQUENCE: 55
agagactggc agactagag                                                    19

<210> SEQ ID NO 56
<211> LENGTH: 21
<212> TYPE: DNA
<213> ORGANISM: Artificial Sequence
<220> FEATURE:
<223> OTHER INFORMATION: Sense primer

<400> SEQUENCE: 56
gggggggcaa taccgaatag a                                                 21

<210> SEQ ID NO 57
<211> LENGTH: 20
<212> TYPE: DNA
<213> ORGANISM: Artificial Sequence
<220> FEATURE:
<223> OTHER INFORMATION: Sense primer

<400> SEQUENCE: 57
atatcaaata aatatccccg                                                   20

<210> SEQ ID NO 58
<211> LENGTH: 20
<212> TYPE: DNA
<213> ORGANISM: Artificial Sequence
<220> FEATURE:
<223> OTHER INFORMATION: Sense primer

<400> SEQUENCE: 58
aagggatatc gaataaatat                                                   20
```

-continued

<210> SEQ ID NO 59
<211> LENGTH: 21
<212> TYPE: DNA
<213> ORGANISM: Artificial Sequence
<220> FEATURE:
<223> OTHER INFORMATION: Sense primer

<400> SEQUENCE: 59
ctagaggctg ggagagggaa g                                              21

<210> SEQ ID NO 60
<211> LENGTH: 21
<212> TYPE: DNA
<213> ORGANISM: Artificial Sequence
<220> FEATURE:
<223> OTHER INFORMATION: Sense primer

<400> SEQUENCE: 60
gacgcagcaa cgccagcagt g                                              21

<210> SEQ ID NO 61
<211> LENGTH: 19
<212> TYPE: DNA
<213> ORGANISM: Artificial Sequence
<220> FEATURE:
<223> OTHER INFORMATION: Sense primer

<400> SEQUENCE: 61
aaataaatat ccccgatga                                                 19

<210> SEQ ID NO 62
<211> LENGTH: 21
<212> TYPE: DNA
<213> ORGANISM: Artificial Sequence
<220> FEATURE:
<223> OTHER INFORMATION: Sense primer

<400> SEQUENCE: 62
cagtgtggga agaaggcttt c                                              21

<210> SEQ ID NO 63
<211> LENGTH: 19
<212> TYPE: DNA
<213> ORGANISM: Artificial Sequence
<220> FEATURE:
<223> OTHER INFORMATION: Sense primer

<400> SEQUENCE: 63
aacaaggtac ccgtctaga                                                 19

<210> SEQ ID NO 64
<211> LENGTH: 20
<212> TYPE: DNA
<213> ORGANISM: Artificial Sequence
<220> FEATURE:
<223> OTHER INFORMATION: Antisense primer

<400> SEQUENCE: 64
ctagacgggt accttgttac                                                20

<210> SEQ ID NO 65
<211> LENGTH: 19
<212> TYPE: DNA
<213> ORGANISM: Artificial Sequence
<220> FEATURE:
<223> OTHER INFORMATION: Antisense primer

<400> SEQUENCE: 65

```
ccgtcatcgg ggatattta                                            19

<210> SEQ ID NO 66
<211> LENGTH: 20
<212> TYPE: DNA
<213> ORGANISM: Artificial Sequence
<220> FEATURE:
<223> OTHER INFORMATION: Antisense primer

<400> SEQUENCE: 66
ttcacggttc cggacaatat                                           20

<210> SEQ ID NO 67
<211> LENGTH: 19
<212> TYPE: DNA
<213> ORGANISM: Artificial Sequence
<220> FEATURE:
<223> OTHER INFORMATION: Antisense primer

<400> SEQUENCE: 67
cggttccgga caatattcg                                            19

<210> SEQ ID NO 68
<211> LENGTH: 20
<212> TYPE: DNA
<213> ORGANISM: Artificial Sequence
<220> FEATURE:
<223> OTHER INFORMATION: Antisense primer

<400> SEQUENCE: 68
cccttcacgg ttccggacaa                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense primer

<400> SEQUENCE: 69
ccacgatcaa actctgtcga                                           20

<210> SEQ ID NO 70
<211> LENGTH: 20
<212> TYPE: DNA
<213> ORGANISM: Artificial Sequence
<220> FEATURE:
<223> OTHER INFORMATION: Antisense primer

<400> SEQUENCE: 70
aaacccttca cggttccgga                                           20

<210> SEQ ID NO 71
<211> LENGTH: 20
<212> TYPE: DNA
<213> ORGANISM: Artificial Sequence
<220> FEATURE:
<223> OTHER INFORMATION: Antisense primer

<400> SEQUENCE: 71
ttccggacaa tattcggtat                                           20

<210> SEQ ID NO 72
<211> LENGTH: 20
<212> TYPE: DNA
<213> ORGANISM: Artificial Sequence
```

```
<220> FEATURE:
<223> OTHER INFORMATION: Antisense primer

<400> SEQUENCE: 72
ccgaaaccct tcacggttcc                                              20

<210> SEQ ID NO 73
<211> LENGTH: 21
<212> TYPE: DNA
<213> ORGANISM: Artificial Sequence
<220> FEATURE:
<223> OTHER INFORMATION: Antisense primer

<400> SEQUENCE: 73
tagtctgcca gtctctttgg c                                            21

<210> SEQ ID NO 74
<211> LENGTH: 21
<212> TYPE: DNA
<213> ORGANISM: Artificial Sequence
<220> FEATURE:
<223> OTHER INFORMATION: Antisense primer

<400> SEQUENCE: 74
gcacctgtgt gatggcccga t                                            21

<210> SEQ ID NO 75
<211> LENGTH: 21
<212> TYPE: DNA
<213> ORGANISM: Artificial Sequence
<220> FEATURE:
<223> OTHER INFORMATION: Antisense primer

<400> SEQUENCE: 75
ctctagtctg ccagtctctt t                                            21

<210> SEQ ID NO 76
<211> LENGTH: 21
<212> TYPE: DNA
<213> ORGANISM: Artificial Sequence
<220> FEATURE:
<223> OTHER INFORMATION: Antisense primer

<400> SEQUENCE: 76
gcagcacctg tgtgatggcc c                                            21

<210> SEQ ID NO 77
<211> LENGTH: 20
<212> TYPE: DNA
<213> ORGANISM: Artificial Sequence
<220> FEATURE:
<223> OTHER INFORMATION: Antisense primer

<400> SEQUENCE: 77
cctgtgtgat ggcccgattt                                              20

<210> SEQ ID NO 78
<211> LENGTH: 21
<212> TYPE: DNA
<213> ORGANISM: Artificial Sequence
<220> FEATURE:
<223> OTHER INFORMATION: Antisense primer

<400> SEQUENCE: 78
tctattcggt attgcccccc c                                            21
```

```
<210> SEQ ID NO 79
<211> LENGTH: 21
<212> TYPE: DNA
<213> ORGANISM: Artificial Sequence
<220> FEATURE:
<223> OTHER INFORMATION: Antisense primer

<400> SEQUENCE: 79
cccctttcgg ttccctactc g                                          21

<210> SEQ ID NO 80
<211> LENGTH: 21
<212> TYPE: DNA
<213> ORGANISM: Artificial Sequence
<220> FEATURE:
<223> OTHER INFORMATION: Antisense primer

<400> SEQUENCE: 80
tccctctccc agcctctagt c                                          21

<210> SEQ ID NO 81
<211> LENGTH: 19
<212> TYPE: DNA
<213> ORGANISM: Artificial Sequence
<220> FEATURE:
<223> OTHER INFORMATION: Antisense primer

<400> SEQUENCE: 81
tcggggatat ttatttgat                                             19

<210> SEQ ID NO 82
<211> LENGTH: 20
<212> TYPE: DNA
<213> ORGANISM: Artificial Sequence
<220> FEATURE:
<223> OTHER INFORMATION: Antisense primer

<400> SEQUENCE: 82
cataccttgg gcggctccct                                            20

<210> SEQ ID NO 83
<211> LENGTH: 19
<212> TYPE: DNA
<213> ORGANISM: Artificial Sequence
<220> FEATURE:
<223> OTHER INFORMATION: Antisense primer

<400> SEQUENCE: 83
cagcctctag tctgccagt                                             19

<210> SEQ ID NO 84
<211> LENGTH: 19
<212> TYPE: DNA
<213> ORGANISM: Artificial Sequence
<220> FEATURE:
<223> OTHER INFORMATION: Sense primer

<400> SEQUENCE: 84
cgaaggcggt gcactggcc                                             19

<210> SEQ ID NO 85
<211> LENGTH: 19
<212> TYPE: DNA
<213> ORGANISM: Artificial Sequence
<220> FEATURE:
<223> OTHER INFORMATION: Sense primer

<400> SEQUENCE: 85
```
gtggcgaagg cggtgcact                          19

<210> SEQ ID NO 86
<211> LENGTH: 20
<212> TYPE: DNA
<213> ORGANISM: Artificial Sequence
<220> FEATURE:
<223> OTHER INFORMATION: Sense primer

<400> SEQUENCE: 86
aggtgtcgcg ggggtccacc                         20

<210> SEQ ID NO 87
<211> LENGTH: 19
<212> TYPE: DNA
<213> ORGANISM: Artificial Sequence
<220> FEATURE:
<223> OTHER INFORMATION: Sense primer

<400> SEQUENCE: 87
tgtctgtcgg gacgaggac                          19

<210> SEQ ID NO 88
<211> LENGTH: 19
<212> TYPE: DNA
<213> ORGANISM: Artificial Sequence
<220> FEATURE:
<223> OTHER INFORMATION: Sense primer

<400> SEQUENCE: 88
gagggcagga gaggtgcat                          19

<210> SEQ ID NO 89
<211> LENGTH: 19
<212> TYPE: DNA
<213> ORGANISM: Artificial Sequence
<220> FEATURE:
<223> OTHER INFORMATION: Sense primer

<400> SEQUENCE: 89
gtccacctcg cggtgccgg                          19

<210> SEQ ID NO 90
<211> LENGTH: 19
<212> TYPE: DNA
<213> ORGANISM: Artificial Sequence
<220> FEATURE:
<223> OTHER INFORMATION: Sense primer

<400> SEQUENCE: 90
cacctcgcgg tgccggagc                          19

<210> SEQ ID NO 91
<211> LENGTH: 20
<212> TYPE: DNA
<213> ORGANISM: Artificial Sequence
<220> FEATURE:
<223> OTHER INFORMATION: Sense primer

<400> SEQUENCE: 91
gggggtccac ctcgcggtgc                         20

<210> SEQ ID NO 92
<211> LENGTH: 19
<212> TYPE: DNA
<213> ORGANISM: Artificial Sequence

```
<220> FEATURE:
<223> OTHER INFORMATION: Sense primer

<400> SEQUENCE: 92
ctcgcggtgc cggagctaa                                                19

<210> SEQ ID NO 93
<211> LENGTH: 19
<212> TYPE: DNA
<213> ORGANISM: Artificial Sequence
<220> FEATURE:
<223> OTHER INFORMATION: Sense primer

<400> SEQUENCE: 93
tgtcgcgggg gtccacctc                                                19

<210> SEQ ID NO 94
<211> LENGTH: 19
<212> TYPE: DNA
<213> ORGANISM: Artificial Sequence
<220> FEATURE:
<223> OTHER INFORMATION: Sense primer

<400> SEQUENCE: 94
ggatacgagg tgtcgcggg                                                19

<210> SEQ ID NO 95
<211> LENGTH: 19
<212> TYPE: DNA
<213> ORGANISM: Artificial Sequence
<220> FEATURE:
<223> OTHER INFORMATION: Sense primer

<400> SEQUENCE: 95
cggagctaac gcactcagt                                                19

<210> SEQ ID NO 96
<211> LENGTH: 20
<212> TYPE: DNA
<213> ORGANISM: Artificial Sequence
<220> FEATURE:
<223> OTHER INFORMATION: Sense primer

<400> SEQUENCE: 96
gtaaacgatg gatacgaggt                                               20

<210> SEQ ID NO 97
<211> LENGTH: 19
<212> TYPE: DNA
<213> ORGANISM: Artificial Sequence
<220> FEATURE:
<223> OTHER INFORMATION: Sense primer

<400> SEQUENCE: 97
tgagtggggg atatcgggc                                                19

<210> SEQ ID NO 98
<211> LENGTH: 19
<212> TYPE: DNA
<213> ORGANISM: Artificial Sequence
<220> FEATURE:
<223> OTHER INFORMATION: Sense primer

<400> SEQUENCE: 98
tacgaggtgt cgcgggggt                                                19
```

```
<210> SEQ ID NO 99
<211> LENGTH: 19
<212> TYPE: DNA
<213> ORGANISM: Artificial Sequence
<220> FEATURE:
<223> OTHER INFORMATION: Sense primer

<400> SEQUENCE: 99
agctaacgca ctcagtatc                                              19

<210> SEQ ID NO 100
<211> LENGTH: 20
<212> TYPE: DNA
<213> ORGANISM: Artificial Sequence
<220> FEATURE:
<223> OTHER INFORMATION: Sense primer

<400> SEQUENCE: 100
acgatggata cgaggtgtcg                                             20

<210> SEQ ID NO 101
<211> LENGTH: 20
<212> TYPE: DNA
<213> ORGANISM: Artificial Sequence
<220> FEATURE:
<223> OTHER INFORMATION: Sense primer

<400> SEQUENCE: 101
gtgccggagc taacgcactc                                             20

<210> SEQ ID NO 102
<211> LENGTH: 20
<212> TYPE: DNA
<213> ORGANISM: Artificial Sequence
<220> FEATURE:
<223> OTHER INFORMATION: Sense primer

<400> SEQUENCE: 102
aggtgcatgg aattcctggt                                             20

<210> SEQ ID NO 103
<211> LENGTH: 20
<212> TYPE: DNA
<213> ORGANISM: Artificial Sequence
<220> FEATURE:
<223> OTHER INFORMATION: Sense primer

<400> SEQUENCE: 103
tgcatggaat tcctggtgga                                             20

<210> SEQ ID NO 104
<211> LENGTH: 19
<212> TYPE: DNA
<213> ORGANISM: Artificial Sequence
<220> FEATURE:
<223> OTHER INFORMATION: Antisense primer

<400> SEQUENCE: 104
cagtgcaccg ccttcgcca                                              19

<210> SEQ ID NO 105
<211> LENGTH: 19
<212> TYPE: DNA
<213> ORGANISM: Artificial Sequence
<220> FEATURE:
<223> OTHER INFORMATION: Antisense primer

<400> SEQUENCE: 105
```
ggccagtgca ccgccttcg                                                19

<210> SEQ ID NO 106
<211> LENGTH: 19
<212> TYPE: DNA
<213> ORGANISM: Artificial Sequence
<220> FEATURE:
<223> OTHER INFORMATION: Antisense primer

<400> SEQUENCE: 106
ggtggacccc cgcgacacc                                                19

<210> SEQ ID NO 107
<211> LENGTH: 19
<212> TYPE: DNA
<213> ORGANISM: Artificial Sequence
<220> FEATURE:
<223> OTHER INFORMATION: Antisense primer

<400> SEQUENCE: 107
ggtcctcgtc ccgacagac                                                19

<210> SEQ ID NO 108
<211> LENGTH: 20
<212> TYPE: DNA
<213> ORGANISM: Artificial Sequence
<220> FEATURE:
<223> OTHER INFORMATION: Antisense primer

<400> SEQUENCE: 108
catgcacctc tcctgccctc                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense primer

<400> SEQUENCE: 109
ttagctccgg caccgcgagg                                               20

<210> SEQ ID NO 110
<211> LENGTH: 19
<212> TYPE: DNA
<213> ORGANISM: Artificial Sequence
<220> FEATURE:
<223> OTHER INFORMATION: Antisense primer

<400> SEQUENCE: 110
gcgaggtgga ccccgcga                                                 19

<210> SEQ ID NO 111
<211> LENGTH: 19
<212> TYPE: DNA
<213> ORGANISM: Artificial Sequence
<220> FEATURE:
<223> OTHER INFORMATION: Antisense primer

<400> SEQUENCE: 111
tgcaccgcct tcgccaccg                                                19

<210> SEQ ID NO 112
<211> LENGTH: 20
<212> TYPE: DNA
<213> ORGANISM: Artificial Sequence

```
<220> FEATURE:
<223> OTHER INFORMATION: Antisense primer

<400> SEQUENCE: 112
cgtatccatc gtttacggcg                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense primer

<400> SEQUENCE: 113 gaccccccgcg acacctcgta                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense primer

<400> SEQUENCE: 114
gagtgcgtta gctccggcac                                               20

<210> SEQ ID NO 115
<211> LENGTH: 19
<212> TYPE: DNA
<213> ORGANISM: Artificial Sequence
<220> FEATURE:
<223> OTHER INFORMATION: Antisense primer

<400> SEQUENCE: 115
tccaccagga attccatgc                                                19

<210> SEQ ID NO 116
<211> LENGTH: 19
<212> TYPE: DNA
<213> ORGANISM: Artificial Sequence
<220> FEATURE:
<223> OTHER INFORMATION: Antisense primer

<400> SEQUENCE: 116
gccaggccag tgcaccgcc                                                19

<210> SEQ ID NO 117
<211> LENGTH: 20
<212> TYPE: DNA
<213> ORGANISM: Artificial Sequence
<220> FEATURE:
<223> OTHER INFORMATION: Antisense primer

<400> SEQUENCE: 117
ccaggaattc catgcacctc                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense primer

<400> SEQUENCE: 118
cctcgtatcc atcgtttacg                                               20
```

```
<210> SEQ ID NO 119
<211> LENGTH: 20
<212> TYPE: DNA
<213> ORGANISM: Artificial Sequence
<220> FEATURE:
<223> OTHER INFORMATION: Antisense primer

<400> SEQUENCE: 119
actgagtgcg ttagctccgg                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense primer

<400> SEQUENCE: 120
gatactgagt gcgttagctc                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense primer

<400> SEQUENCE: 121
gcgacacctc gtatccatcg                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense primer

<400> SEQUENCE: 122
cgggatactg agtgcgttag                                              20

<210> SEQ ID NO 123
<211> LENGTH: 19
<212> TYPE: DNA
<213> ORGANISM: Artificial Sequence
<220> FEATURE:
<223> OTHER INFORMATION: Antisense primer

<400> SEQUENCE: 123
gcccgatatc ccccactca                                               19

<210> SEQ ID NO 124
<211> LENGTH: 19
<212> TYPE: DNA
<213> ORGANISM: Artificial Sequence
<220> FEATURE:
<223> OTHER INFORMATION: Sense primer

<400> SEQUENCE: 124
cagtgcaccg ccttcgcca                                               19

<210> SEQ ID NO 125
<211> LENGTH: 19
<212> TYPE: DNA
<213> ORGANISM: Artificial Sequence
<220> FEATURE:
<223> OTHER INFORMATION: Sense primer

<400> SEQUENCE: 125
```
ggccagtgca ccgccttcg                                                    19

<210> SEQ ID NO 126
<211> LENGTH: 19
<212> TYPE: DNA
<213> ORGANISM: Artificial Sequence
<220> FEATURE:
<223> OTHER INFORMATION: Sense primer

<400> SEQUENCE: 126
ggtggacccc cgcgacacc                                                    19

<210> SEQ ID NO 127
<211> LENGTH: 19
<212> TYPE: DNA
<213> ORGANISM: Artificial Sequence
<220> FEATURE:
<223> OTHER INFORMATION: Sense primer

<400> SEQUENCE: 127
ggtcctcgtc ccgacagac                                                    19

<210> SEQ ID NO 128
<211> LENGTH: 20
<212> TYPE: DNA
<213> ORGANISM: Artificial Sequence
<220> FEATURE:
<223> OTHER INFORMATION: Sense primer

<400> SEQUENCE: 128
catgcacctc tcctgccctc                                                   20

<210> SEQ ID NO 129
<211> LENGTH: 20
<212> TYPE: DNA
<213> ORGANISM: Artificial Sequence
<220> FEATURE:
<223> OTHER INFORMATION: Sense primer

<400> SEQUENCE: 129
ttagctccgg caccgcgagg                                                   20

<210> SEQ ID NO 130
<211> LENGTH: 19
<212> TYPE: DNA
<213> ORGANISM: Artificial Sequence
<220> FEATURE:
<223> OTHER INFORMATION: Sense primer

<400> SEQUENCE: 130
gcgaggtgga cccccgcga                                                    19

<210> SEQ ID NO 131
<211> LENGTH: 19
<212> TYPE: DNA
<213> ORGANISM: Artificial Sequence
<220> FEATURE:
<223> OTHER INFORMATION: Sense primer

<400> SEQUENCE: 131
tgcaccgcct tcgccaccg                                                    19

<210> SEQ ID NO 132
<211> LENGTH: 20
<212> TYPE: DNA
<213> ORGANISM: Artificial Sequence

```
<220> FEATURE:
<223> OTHER INFORMATION: Sense primer

<400> SEQUENCE: 132
cgtatccatc gtttacggcg                                                    20

<210> SEQ ID NO 133
<211> LENGTH: 20
<212> TYPE: DNA
<213> ORGANISM: Artificial Sequence
<220> FEATURE:
<223> OTHER INFORMATION: Sense primer

<400> SEQUENCE: 133 gaccccccgcg acacctcgta                                                   20

<210> SEQ ID NO 134
<211> LENGTH: 20
<212> TYPE: DNA
<213> ORGANISM: Artificial Sequence
<220> FEATURE:
<223> OTHER INFORMATION: Sense primer

<400> SEQUENCE: 134
gagtgcgtta gctccggcac                                                    20

<210> SEQ ID NO 135
<211> LENGTH: 19
<212> TYPE: DNA
<213> ORGANISM: Artificial Sequence
<220> FEATURE:
<223> OTHER INFORMATION: Sense primer

<400> SEQUENCE: 135
tccaccagga attccatgc                                                     19

<210> SEQ ID NO 136
<211> LENGTH: 19
<212> TYPE: DNA
<213> ORGANISM: Artificial Sequence
<220> FEATURE:
<223> OTHER INFORMATION: Sense primer

<400> SEQUENCE: 136
gccaggccag tgcaccgcc                                                     19

<210> SEQ ID NO 137
<211> LENGTH: 20
<212> TYPE: DNA
<213> ORGANISM: Artificial Sequence
<220> FEATURE:
<223> OTHER INFORMATION: Sense primer

<400> SEQUENCE: 137
ccaggaattc catgcacctc                                                    20

<210> SEQ ID NO 138
<211> LENGTH: 20
<212> TYPE: DNA
<213> ORGANISM: Artificial Sequence
<220> FEATURE:
<223> OTHER INFORMATION: Sense primer

<400> SEQUENCE: 138
cctcgtatcc atcgtttacg                                                    20
```

```
<210> SEQ ID NO 139
<211> LENGTH: 20
<212> TYPE: DNA
<213> ORGANISM: Artificial Sequence
<220> FEATURE:
<223> OTHER INFORMATION: Sense primer

<400> SEQUENCE: 139
actgagtgcg ttagctccgg                                               20

<210> SEQ ID NO 140
<211> LENGTH: 20
<212> TYPE: DNA
<213> ORGANISM: Artificial Sequence
<220> FEATURE:
<223> OTHER INFORMATION: Sense primer

<400> SEQUENCE: 140
gatactgagt gcgttagctc                                               20

<210> SEQ ID NO 141
<211> LENGTH: 20
<212> TYPE: DNA
<213> ORGANISM: Artificial Sequence
<220> FEATURE:
<223> OTHER INFORMATION: Sense primer

<400> SEQUENCE: 141
gcgacacctc gtatccatcg                                               20

<210> SEQ ID NO 142
<211> LENGTH: 20
<212> TYPE: DNA
<213> ORGANISM: Artificial Sequence
<220> FEATURE:
<223> OTHER INFORMATION: Sense primer

<400> SEQUENCE: 142
cgggatactg agtgcgttag                                               20

<210> SEQ ID NO 143
<211> LENGTH: 19
<212> TYPE: DNA
<213> ORGANISM: Artificial Sequence
<220> FEATURE:
<223> OTHER INFORMATION: Sense primer

<400> SEQUENCE: 143
gcccgatatc ccccactca                                                19

<210> SEQ ID NO 144
<211> LENGTH: 19
<212> TYPE: DNA
<213> ORGANISM: Artificial Sequence
<220> FEATURE:
<223> OTHER INFORMATION: Antisense primer

<400> SEQUENCE: 144
cagtgcaccg ccttcgcca                                                19

<210> SEQ ID NO 145
<211> LENGTH: 19
<212> TYPE: DNA
<213> ORGANISM: Artificial Sequence
<220> FEATURE:
<223> OTHER INFORMATION: Antisense primer

<400> SEQUENCE: 145
```

```
ggccagtgca ccgccttcg                                                    19

<210> SEQ ID NO 146
<211> LENGTH: 19
<212> TYPE: DNA
<213> ORGANISM: Artificial Sequence
<220> FEATURE:
<223> OTHER INFORMATION: Antisense primer

<400> SEQUENCE: 146
ggtggacccc cgcgacacc                                                    19

<210> SEQ ID NO 147
<211> LENGTH: 19
<212> TYPE: DNA
<213> ORGANISM: Artificial Sequence
<220> FEATURE:
<223> OTHER INFORMATION: Antisense primer

<400> SEQUENCE: 147
ggtcctcgtc ccgacagac                                                    19

<210> SEQ ID NO 148
<211> LENGTH: 20
<212> TYPE: DNA
<213> ORGANISM: Artificial Sequence
<220> FEATURE:
<223> OTHER INFORMATION: Antisense primer

<400> SEQUENCE: 148
catgcacctc tcctgccctc                                                   20

<210> SEQ ID NO 149
<211> LENGTH: 20
<212> TYPE: DNA
<213> ORGANISM: Artificial Sequence
<220> FEATURE:
<223> OTHER INFORMATION: Antisense primer

<400> SEQUENCE: 149
ttagctccgg caccgcgagg                                                   20

<210> SEQ ID NO 150
<211> LENGTH: 19
<212> TYPE: DNA
<213> ORGANISM: Artificial Sequence
<220> FEATURE:
<223> OTHER INFORMATION: Antisense primer

<400> SEQUENCE: 150
gcgaggtgga cccccgcga                                                    19

<210> SEQ ID NO 151
<211> LENGTH: 19
<212> TYPE: DNA
<213> ORGANISM: Artificial Sequence
<220> FEATURE:
<223> OTHER INFORMATION: Antisense primer

<400> SEQUENCE: 151
tgcaccgcct tcgccaccg                                                    19

<210> SEQ ID NO 152
<211> LENGTH: 20
<212> TYPE: DNA
<213> ORGANISM: Artificial Sequence
```

```
<220> FEATURE:
<223> OTHER INFORMATION: Antisense primer

<400> SEQUENCE: 152
cgtatccatc gtttacggcg                                        20

<210> SEQ ID NO 153
<211> LENGTH: 20
<212> TYPE: DNA
<213> ORGANISM: Artificial Sequence
<220> FEATURE:
<223> OTHER INFORMATION: Antisense primer

<400> SEQUENCE: 153 gaccccccgcg acacctcgta                                       20

<210> SEQ ID NO 154
<211> LENGTH: 20
<212> TYPE: DNA
<213> ORGANISM: Artificial Sequence
<220> FEATURE:
<223> OTHER INFORMATION: Antisense primer

<400> SEQUENCE: 154
gagtgcgtta gctccggcac                                        20

<210> SEQ ID NO 155
<211> LENGTH: 19
<212> TYPE: DNA
<213> ORGANISM: Artificial Sequence
<220> FEATURE:
<223> OTHER INFORMATION: Antisense primer

<400> SEQUENCE: 155
tccaccagga attccatgc                                         19

<210> SEQ ID NO 156
<211> LENGTH: 19
<212> TYPE: DNA
<213> ORGANISM: Artificial Sequence
<220> FEATURE:
<223> OTHER INFORMATION: Antisense primer

<400> SEQUENCE: 156
gccaggccag tgcaccgcc                                         19

<210> SEQ ID NO 157
<211> LENGTH: 20
<212> TYPE: DNA
<213> ORGANISM: Artificial Sequence
<220> FEATURE:
<223> OTHER INFORMATION: Antisense primer

<400> SEQUENCE: 157
ccaggaattc catgcacctc                                        20

<210> SEQ ID NO 158
<211> LENGTH: 20
<212> TYPE: DNA
<213> ORGANISM: Artificial Sequence
<220> FEATURE:
<223> OTHER INFORMATION: Antisense primer

<400> SEQUENCE: 158
cctcgtatcc atcgtttacg                                        20
```

```
<210> SEQ ID NO 159
<211> LENGTH: 20
<212> TYPE: DNA
<213> ORGANISM: Artificial Sequence
<220> FEATURE:
<223> OTHER INFORMATION: Antisense primer

<400> SEQUENCE: 159
actgagtgcg ttagctccgg                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense primer

<400> SEQUENCE: 160
gatactgagt gcgttagctc                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense primer

<400> SEQUENCE: 161
gcgacacctc gtatccatcg                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense primer

<400> SEQUENCE: 162
cgggatactg agtgcgttag                                              20

<210> SEQ ID NO 163
<211> LENGTH: 19
<212> TYPE: DNA
<213> ORGANISM: Artificial Sequence
<220> FEATURE:
<223> OTHER INFORMATION: Antisense primer

<400> SEQUENCE: 163
gcccgatatc ccccactca                                               19

<210> SEQ ID NO 164
<211> LENGTH: 20
<212> TYPE: DNA
<213> ORGANISM: Artificial Sequence
<220> FEATURE:
<223> OTHER INFORMATION: Sense primer

<400> SEQUENCE: 164
gggagacgaa aaggtaatcg                                              20

<210> SEQ ID NO 165
<211> LENGTH: 20
<212> TYPE: DNA
<213> ORGANISM: Artificial Sequence
<220> FEATURE:
<223> OTHER INFORMATION: Sense primer

<400> SEQUENCE: 165
``` aaagttctttt cggtgacggg                                                    20

<210> SEQ ID NO 166
<211> LENGTH: 20
<212> TYPE: DNA
<213> ORGANISM: Artificial Sequence
<220> FEATURE:
<223> OTHER INFORMATION: Sense primer

<400> SEQUENCE: 166
cggggaaggt tgatatgtta                                                     20

<210> SEQ ID NO 167
<211> LENGTH: 19
<212> TYPE: DNA
<213> ORGANISM: Artificial Sequence
<220> FEATURE:
<223> OTHER INFORMATION: Sense primer

<400> SEQUENCE: 167
gagggagaaa ccgggggat                                                      19

<210> SEQ ID NO 168
<211> LENGTH: 19
<212> TYPE: DNA
<213> ORGANISM: Artificial Sequence
<220> FEATURE:
<223> OTHER INFORMATION: Sense primer

<400> SEQUENCE: 168
aatcgctaat atcggttac                                                      19

<210> SEQ ID NO 169
<211> LENGTH: 20
<212> TYPE: DNA
<213> ORGANISM: Artificial Sequence
<220> FEATURE:
<223> OTHER INFORMATION: Sense primer

<400> SEQUENCE: 169
ccgggggatc ttcggacctc                                                     20

<210> SEQ ID NO 170
<211> LENGTH: 20
<212> TYPE: DNA
<213> ORGANISM: Artificial Sequence
<220> FEATURE:
<223> OTHER INFORMATION: Sense primer

<400> SEQUENCE: 170
taatatcgcc tgctgttgac                                                     20

<210> SEQ ID NO 171
<211> LENGTH: 19
<212> TYPE: DNA
<213> ORGANISM: Artificial Sequence
<220> FEATURE:
<223> OTHER INFORMATION: Sense primer

<400> SEQUENCE: 171
tcggtgacgg ggaaggttg                                                      19

<210> SEQ ID NO 172
<211> LENGTH: 19
<212> TYPE: DNA
<213> ORGANISM: Artificial Sequence

```
<220> FEATURE:
<223> OTHER INFORMATION: Sense primer

<400> SEQUENCE: 172
ggagaaaccg ggggatctt                                                19

<210> SEQ ID NO 173
<211> LENGTH: 20
<212> TYPE: DNA
<213> ORGANISM: Artificial Sequence
<220> FEATURE:
<223> OTHER INFORMATION: Sense primer

<400> SEQUENCE: 173
acgtcctgag ggagaaaccg                                               20

<210> SEQ ID NO 174
<211> LENGTH: 20
<212> TYPE: DNA
<213> ORGANISM: Artificial Sequence
<220> FEATURE:
<223> OTHER INFORMATION: Sense primer

<400> SEQUENCE: 174
agacgaaaag gtaatcgcta                                               20

<210> SEQ ID NO 175
<211> LENGTH: 19
<212> TYPE: DNA
<213> ORGANISM: Artificial Sequence
<220> FEATURE:
<223> OTHER INFORMATION: Sense primer

<400> SEQUENCE: 175
gtgacgggga aggttgata                                                19

<210> SEQ ID NO 176
<211> LENGTH: 19
<212> TYPE: DNA
<213> ORGANISM: Artificial Sequence
<220> FEATURE:
<223> OTHER INFORMATION: Sense primer

<400> SEQUENCE: 176
gaaaccgggg gatcttcgg                                                19

<210> SEQ ID NO 177
<211> LENGTH: 20
<212> TYPE: DNA
<213> ORGANISM: Artificial Sequence
<220> FEATURE:
<223> OTHER INFORMATION: Sense primer

<400> SEQUENCE: 177
tcctgaggga gaaaccgggg                                               20

<210> SEQ ID NO 178
<211> LENGTH: 20
<212> TYPE: DNA
<213> ORGANISM: Artificial Sequence
<220> FEATURE:
<223> OTHER INFORMATION: Sense primer

<400> SEQUENCE: 178
cgaaaaggta atcgctaata                                               20
```

<210> SEQ ID NO 179
<211> LENGTH: 20
<212> TYPE: DNA
<213> ORGANISM: Artificial Sequence
<220> FEATURE:
<223> OTHER INFORMATION: Sense primer

<400> SEQUENCE: 179
aaaggtaatc gctaatatcg                                               20

<210> SEQ ID NO 180
<211> LENGTH: 20
<212> TYPE: DNA
<213> ORGANISM: Artificial Sequence
<220> FEATURE:
<223> OTHER INFORMATION: Sense primer

<400> SEQUENCE: 180
tcgtgggaga cgaaaaggta                                               20

<210> SEQ ID NO 181
<211> LENGTH: 20
<212> TYPE: DNA
<213> ORGANISM: Artificial Sequence
<220> FEATURE:
<223> OTHER INFORMATION: Sense primer

<400> SEQUENCE: 181
cggacctcgt gctattggag                                               20

<210> SEQ ID NO 182
<211> LENGTH: 19
<212> TYPE: DNA
<213> ORGANISM: Artificial Sequence
<220> FEATURE:
<223> OTHER INFORMATION: Sense primer

<400> SEQUENCE: 182
gttctttcgg tgacgggga                                                19

<210> SEQ ID NO 183
<211> LENGTH: 19
<212> TYPE: DNA
<213> ORGANISM: Artificial Sequence
<220> FEATURE:
<223> OTHER INFORMATION: Sense primer

<400> SEQUENCE: 183
ctttcggtga cggggaagg                                                19

<210> SEQ ID NO 184
<211> LENGTH: 19
<212> TYPE: DNA
<213> ORGANISM: Artificial Sequence
<220> FEATURE:
<223> OTHER INFORMATION: Antisense primer

<400> SEQUENCE: 184
atcccccggt ttctccctc                                                19

<210> SEQ ID NO 185
<211> LENGTH: 19
<212> TYPE: DNA
<213> ORGANISM: Artificial Sequence
<220> FEATURE:
<223> OTHER INFORMATION: Antisense primer

<400> SEQUENCE: 185

```
atattagcga ttaccttt                                                  19

<210> SEQ ID NO 186
<211> LENGTH: 20
<212> TYPE: DNA
<213> ORGANISM: Artificial Sequence
<220> FEATURE:
<223> OTHER INFORMATION: Antisense primer

<400> SEQUENCE: 186
caaccttccc cgtcaccgaa                                                20

<210> SEQ ID NO 187
<211> LENGTH: 20
<212> TYPE: DNA
<213> ORGANISM: Artificial Sequence
<220> FEATURE:
<223> OTHER INFORMATION: Antisense primer

<400> SEQUENCE: 187
ccgaagatcc cccggtttct                                                20

<210> SEQ ID NO 188
<211> LENGTH: 20
<212> TYPE: DNA
<213> ORGANISM: Artificial Sequence
<220> FEATURE:
<223> OTHER INFORMATION: Antisense primer

<400> SEQUENCE: 188
ctccaatagc acgaggtccg                                                20

<210> SEQ ID NO 189
<211> LENGTH: 20
<212> TYPE: DNA
<213> ORGANISM: Artificial Sequence
<220> FEATURE:
<223> OTHER INFORMATION: Antisense primer

<400> SEQUENCE: 189
accgatatta gcgattacct                                                20

<210> SEQ ID NO 190
<211> LENGTH: 19
<212> TYPE: DNA
<213> ORGANISM: Artificial Sequence
<220> FEATURE:
<223> OTHER INFORMATION: Antisense primer

<400> SEQUENCE: 190
aagatccccc ggtttctcc                                                 19

<210> SEQ ID NO 191
<211> LENGTH: 20
<212> TYPE: DNA
<213> ORGANISM: Artificial Sequence
<220> FEATURE:
<223> OTHER INFORMATION: Antisense primer

<400> SEQUENCE: 191
tatcaacctt ccccgtcacc                                                20

<210> SEQ ID NO 192
<211> LENGTH: 20
<212> TYPE: DNA
<213> ORGANISM: Artificial Sequence
```

```
<220> FEATURE:
<223> OTHER INFORMATION: Antisense primer

<400> SEQUENCE: 192
ggtttctccc tcaggacgta                                                    20

<210> SEQ ID NO 193
<211> LENGTH: 20
<212> TYPE: DNA
<213> ORGANISM: Artificial Sequence
<220> FEATURE:
<223> OTHER INFORMATION: Antisense primer

<400> SEQUENCE: 193
ggtccgaaga tcccccggtt                                                    20

<210> SEQ ID NO 194
<211> LENGTH: 19
<212> TYPE: DNA
<213> ORGANISM: Artificial Sequence
<220> FEATURE:
<223> OTHER INFORMATION: Antisense primer

<400> SEQUENCE: 194
tttcacgaca gacctaatg                                                     19

<210> SEQ ID NO 195
<211> LENGTH: 20
<212> TYPE: DNA
<213> ORGANISM: Artificial Sequence
<220> FEATURE:
<223> OTHER INFORMATION: Antisense primer

<400> SEQUENCE: 195
gtaaccgata ttagcgatta                                                    20

<210> SEQ ID NO 196
<211> LENGTH: 20
<212> TYPE: DNA
<213> ORGANISM: Artificial Sequence
<220> FEATURE:
<223> OTHER INFORMATION: Antisense primer

<400> SEQUENCE: 196
acatatcaac cttccccgtc                                                    20

<210> SEQ ID NO 197
<211> LENGTH: 20
<212> TYPE: DNA
<213> ORGANISM: Artificial Sequence
<220> FEATURE:
<223> OTHER INFORMATION: Antisense primer

<400> SEQUENCE: 197
cccggtttct ccctcaggac                                                    20

<210> SEQ ID NO 198
<211> LENGTH: 20
<212> TYPE: DNA
<213> ORGANISM: Artificial Sequence
<220> FEATURE:
<223> OTHER INFORMATION: Antisense primer

<400> SEQUENCE: 198
gcgattacct tttcgtctcc                                                    20
```

<210> SEQ ID NO 199
<211> LENGTH: 20
<212> TYPE: DNA
<213> ORGANISM: Artificial Sequence
<220> FEATURE:
<223> OTHER INFORMATION: Antisense primer

<400> SEQUENCE: 199
ccccgtcacc gaaagaactt					20

<210> SEQ ID NO 200
<211> LENGTH: 20
<212> TYPE: DNA
<213> ORGANISM: Artificial Sequence
<220> FEATURE:
<223> OTHER INFORMATION: Antisense primer

<400> SEQUENCE: 200
ttaacatatc aaccttcccc					20

<210> SEQ ID NO 201
<211> LENGTH: 20
<212> TYPE: DNA
<213> ORGANISM: Artificial Sequence
<220> FEATURE:
<223> OTHER INFORMATION: Antisense primer

<400> SEQUENCE: 201
ttagcgatta cctttcgtc					20

<210> SEQ ID NO 202
<211> LENGTH: 20
<212> TYPE: DNA
<213> ORGANISM: Artificial Sequence
<220> FEATURE:
<223> OTHER INFORMATION: Antisense primer

<400> SEQUENCE: 202
cttccccgtc accgaaagaa					20

<210> SEQ ID NO 203
<211> LENGTH: 20
<212> TYPE: DNA
<213> ORGANISM: Artificial Sequence
<220> FEATURE:
<223> OTHER INFORMATION: Antisense primer

<400> SEQUENCE: 203 attaccttttt cgtctcccac					20

<210> SEQ ID NO 204
<211> LENGTH: 19
<212> TYPE: DNA
<213> ORGANISM: Artificial Sequence
<220> FEATURE:
<223> OTHER INFORMATION: Sense primer

<400> SEQUENCE: 204
gggaaaccgt gagggcgct					19

<210> SEQ ID NO 205
<211> LENGTH: 20
<212> TYPE: DNA
<213> ORGANISM: Artificial Sequence
<220> FEATURE:
<223> OTHER INFORMATION: Sense primer

<400> SEQUENCE: 205
gcgaaacgtc cccaatgcgg          20

<210> SEQ ID NO 206
<211> LENGTH: 21
<212> TYPE: DNA
<213> ORGANISM: Artificial Sequence
<220> FEATURE:
<223> OTHER INFORMATION: Sense primer

<400> SEQUENCE: 206
ccgcagggaa accggtaagc c        21

<210> SEQ ID NO 207
<211> LENGTH: 20
<212> TYPE: DNA
<213> ORGANISM: Artificial Sequence
<220> FEATURE:
<223> OTHER INFORMATION: Sense primer

<400> SEQUENCE: 207
cccgggaaag ggcagtgata          20

<210> SEQ ID NO 208
<211> LENGTH: 19
<212> TYPE: DNA
<213> ORGANISM: Artificial Sequence
<220> FEATURE:
<223> OTHER INFORMATION: Sense primer

<400> SEQUENCE: 208
gggaaagggc agtgatact           19

<210> SEQ ID NO 209
<211> LENGTH: 20
<212> TYPE: DNA
<213> ORGANISM: Artificial Sequence
<220> FEATURE:
<223> OTHER INFORMATION: Sense primer

<400> SEQUENCE: 209
aatccggggc aggcgaaggg          20

<210> SEQ ID NO 210
<211> LENGTH: 20
<212> TYPE: DNA
<213> ORGANISM: Artificial Sequence
<220> FEATURE:
<223> OTHER INFORMATION: Sense primer

<400> SEQUENCE: 210
agggtactgg aacgtccctt          20

<210> SEQ ID NO 211
<211> LENGTH: 21
<212> TYPE: DNA
<213> ORGANISM: Artificial Sequence
<220> FEATURE:
<223> OTHER INFORMATION: Sense primer

<400> SEQUENCE: 211
aagcgtccgg ccagaacgcg c        21

<210> SEQ ID NO 212
<211> LENGTH: 20
<212> TYPE: DNA
<213> ORGANISM: Artificial Sequence

```
<220> FEATURE:
<223> OTHER INFORMATION: Sense primer

<400> SEQUENCE: 212
cgcctaaagg ggcatgggct                                          20

<210> SEQ ID NO 213
<211> LENGTH: 20
<212> TYPE: DNA
<213> ORGANISM: Artificial Sequence
<220> FEATURE:
<223> OTHER INFORMATION: Sense primer

<400> SEQUENCE: 213
ggctatttcc cgctcatgcc                                          20

<210> SEQ ID NO 214
<211> LENGTH: 21
<212> TYPE: DNA
<213> ORGANISM: Artificial Sequence
<220> FEATURE:
<223> OTHER INFORMATION: Sense primer

<400> SEQUENCE: 214
cgtacgccct cgggtaagag g                                        21

<210> SEQ ID NO 215
<211> LENGTH: 20
<212> TYPE: DNA
<213> ORGANISM: Artificial Sequence
<220> FEATURE:
<223> OTHER INFORMATION: Sense primer

<400> SEQUENCE: 215
aacggcccgc caaaccgata                                          20

<210> SEQ ID NO 216
<211> LENGTH: 19
<212> TYPE: DNA
<213> ORGANISM: Artificial Sequence
<220> FEATURE:
<223> OTHER INFORMATION: Sense primer

<400> SEQUENCE: 216
agccggccct gcaagtcac                                           19

<210> SEQ ID NO 217
<211> LENGTH: 19
<212> TYPE: DNA
<213> ORGANISM: Artificial Sequence
<220> FEATURE:
<223> OTHER INFORMATION: Sense primer

<400> SEQUENCE: 217
cactgcttaa agacccggg                                           19

<210> SEQ ID NO 218
<211> LENGTH: 21
<212> TYPE: DNA
<213> ORGANISM: Artificial Sequence
<220> FEATURE:
<223> OTHER INFORMATION: Sense primer

<400> SEQUENCE: 218
ggagctaatc cggggcaggc g                                        21
```

```
<210> SEQ ID NO 219
<211> LENGTH: 20
<212> TYPE: DNA
<213> ORGANISM: Artificial Sequence
<220> FEATURE:
<223> OTHER INFORMATION: Sense primer

<400> SEQUENCE: 219
aaaccgtgag ggcgctaccc                                              20

<210> SEQ ID NO 220
<211> LENGTH: 21
<212> TYPE: DNA
<213> ORGANISM: Artificial Sequence
<220> FEATURE:
<223> OTHER INFORMATION: Sense primer

<400> SEQUENCE: 220
aggcgaaggg tactggaacg t                                            21

<210> SEQ ID NO 221
<211> LENGTH: 20
<212> TYPE: DNA
<213> ORGANISM: Artificial Sequence
<220> FEATURE:
<223> OTHER INFORMATION: Sense primer

<400> SEQUENCE: 221
acccccagtg ctcccgaaag                                              20

<210> SEQ ID NO 222
<211> LENGTH: 21
<212> TYPE: DNA
<213> ORGANISM: Artificial Sequence
<220> FEATURE:
<223> OTHER INFORMATION: Sense primer

<400> SEQUENCE: 222
cccttcgcct aaaggggcat g                                            21

<210> SEQ ID NO 223
<211> LENGTH: 21
<212> TYPE: DNA
<213> ORGANISM: Artificial Sequence
<220> FEATURE:
<223> OTHER INFORMATION: Sense primer

<400> SEQUENCE: 223
gcatgggcta tttcccgctc a                                            21

<210> SEQ ID NO 224
<211> LENGTH: 19
<212> TYPE: DNA
<213> ORGANISM: Artificial Sequence
<220> FEATURE:
<223> OTHER INFORMATION: Sense primer

<400> SEQUENCE: 224
gggaaaccgt gagggcgct                                               19

<210> SEQ ID NO 225
<211> LENGTH: 20
<212> TYPE: DNA
<213> ORGANISM: Artificial Sequence
<220> FEATURE:
<223> OTHER INFORMATION: Sense primer

<400> SEQUENCE: 225
```
gcgaaacgtc cccaatgcgg                                              20

<210> SEQ ID NO 226
<211> LENGTH: 21
<212> TYPE: DNA
<213> ORGANISM: Artificial Sequence
<220> FEATURE:
<223> OTHER INFORMATION: Antisense primer

<400> SEQUENCE: 226
ccgcattggg gacgtttcgc g                                            21

<210> SEQ ID NO 227
<211> LENGTH: 21
<212> TYPE: DNA
<213> ORGANISM: Artificial Sequence
<220> FEATURE:
<223> OTHER INFORMATION: Antisense primer

<400> SEQUENCE: 227
gcgccctcac ggtttcccgc a                                            21

<210> SEQ ID NO 228
<211> LENGTH: 21
<212> TYPE: DNA
<213> ORGANISM: Artificial Sequence
<220> FEATURE:
<223> OTHER INFORMATION: Antisense primer

<400> SEQUENCE: 228
ccgcattggg gacgtttcgc g                                            21

<210> SEQ ID NO 229
<211> LENGTH: 21
<212> TYPE: DNA
<213> ORGANISM: Artificial Sequence
<220> FEATURE:
<223> OTHER INFORMATION: Antisense primer

<400> SEQUENCE: 229
gcgccctcac ggtttcccgc a                                            21

<210> SEQ ID NO 230
<211> LENGTH: 21
<212> TYPE: DNA
<213> ORGANISM: Artificial Sequence
<220> FEATURE:
<223> OTHER INFORMATION: Antisense primer

<400> SEQUENCE: 230
ttcccgcatt ggggacgttt c                                            21

<210> SEQ ID NO 231
<211> LENGTH: 20
<212> TYPE: DNA
<213> ORGANISM: Artificial Sequence
<220> FEATURE:
<223> OTHER INFORMATION: Antisense primer

<400> SEQUENCE: 231
tagcgccctc acggtttccc                                              20

<210> SEQ ID NO 232
<211> LENGTH: 20
<212> TYPE: DNA
<213> ORGANISM: Artificial Sequence

```
<220> FEATURE:
<223> OTHER INFORMATION: Antisense primer

<400> SEQUENCE: 232
ggcttaccgg tttccctgcg                                           20

<210> SEQ ID NO 233
<211> LENGTH: 19
<212> TYPE: DNA
<213> ORGANISM: Artificial Sequence
<220> FEATURE:
<223> OTHER INFORMATION: Antisense primer

<400> SEQUENCE: 233
ctgcccttct ccgggttga                                            19

<210> SEQ ID NO 234
<211> LENGTH: 19
<212> TYPE: DNA
<213> ORGANISM: Artificial Sequence
<220> FEATURE:
<223> OTHER INFORMATION: Antisense primer

<400> SEQUENCE: 234
tcactgccct ttcccgggt                                            19

<210> SEQ ID NO 235
<211> LENGTH: 19
<212> TYPE: DNA
<213> ORGANISM: Artificial Sequence
<220> FEATURE:
<223> OTHER INFORMATION: Antisense primer

<400> SEQUENCE: 235
gtatcactgc cctttcccg                                            19

<210> SEQ ID NO 236
<211> LENGTH: 20
<212> TYPE: DNA
<213> ORGANISM: Artificial Sequence
<220> FEATURE:
<223> OTHER INFORMATION: Antisense primer

<400> SEQUENCE: 236
gcccgggtct ttaagcagtg                                           20

<210> SEQ ID NO 237
<211> LENGTH: 21
<212> TYPE: DNA
<213> ORGANISM: Artificial Sequence
<220> FEATURE:
<223> OTHER INFORMATION: Antisense primer

<400> SEQUENCE: 237
ctcccgcccc ctagccctgc a                                         21

<210> SEQ ID NO 238
<211> LENGTH: 21
<212> TYPE: DNA
<213> ORGANISM: Artificial Sequence
<220> FEATURE:
<223> OTHER INFORMATION: Antisense primer

<400> SEQUENCE: 238
cccgggatct gtggatttcg c                                         21
```

```
<210> SEQ ID NO 239
<211> LENGTH: 19
<212> TYPE: DNA
<213> ORGANISM: Artificial Sequence
<220> FEATURE:
<223> OTHER INFORMATION: Antisense primer

<400> SEQUENCE: 239
tacccgaggg cgtacgact                                             19

<210> SEQ ID NO 240
<211> LENGTH: 21
<212> TYPE: DNA
<213> ORGANISM: Artificial Sequence
<220> FEATURE:
<223> OTHER INFORMATION: Antisense primer

<400> SEQUENCE: 240
cctcttaccc gagggcgtac g                                          21

<210> SEQ ID NO 241
<211> LENGTH: 19
<212> TYPE: DNA
<213> ORGANISM: Artificial Sequence
<220> FEATURE:
<223> OTHER INFORMATION: Antisense primer

<400> SEQUENCE: 241
ttcgcctgcc ccggattag                                             19

<210> SEQ ID NO 242
<211> LENGTH: 21
<212> TYPE: DNA
<213> ORGANISM: Artificial Sequence
<220> FEATURE:
<223> OTHER INFORMATION: Antisense primer

<400> SEQUENCE: 242
ggcggcaggc ttaccggttt c                                          21

<210> SEQ ID NO 243
<211> LENGTH: 21
<212> TYPE: DNA
<213> ORGANISM: Artificial Sequence
<220> FEATURE:
<223> OTHER INFORMATION: Antisense primer

<400> SEQUENCE: 243
cggattagct ccagtttccc g                                          21

<210> SEQ ID NO 244
<211> LENGTH: 19
<212> TYPE: DNA
<213> ORGANISM: Artificial Sequence
<220> FEATURE:
<223> OTHER INFORMATION: Antisense primer

<400> SEQUENCE: 244
ggacgttcca gtaccctttc                                            19

<210> SEQ ID NO 245
<211> LENGTH: 20
<212> TYPE: DNA
<213> ORGANISM: Artificial Sequence
<220> FEATURE:
<223> OTHER INFORMATION: Antisense primer

<400> SEQUENCE: 245
```
ccccggatta gctccagttt                               20

<210> SEQ ID NO 246
<211> LENGTH: 21
<212> TYPE: DNA
<213> ORGANISM: Artificial Sequence
<220> FEATURE:
<223> OTHER INFORMATION: Antisense primer

<400> SEQUENCE: 246 taccctttcgc ctgccccgga t                             21

<210> SEQ ID NO 247
<211> LENGTH: 19
<212> TYPE: DNA
<213> ORGANISM: Artificial Sequence
<220> FEATURE:
<223> OTHER INFORMATION: Antisense primer

<400> SEQUENCE: 247
ccatgcccct ttaggcgaa                                 19

<210> SEQ ID NO 248
<211> LENGTH: 21
<212> TYPE: DNA
<213> ORGANISM: Artificial Sequence
<220> FEATURE:
<223> OTHER INFORMATION: Sense primer

<400> SEQUENCE: 248
agagtcaacc tgacgagctt a                              21

<210> SEQ ID NO 249
<211> LENGTH: 21
<212> TYPE: DNA
<213> ORGANISM: Artificial Sequence
<220> FEATURE:
<223> OTHER INFORMATION: Sense primer

<400> SEQUENCE: 249
gtcaacctga cgagcttact c                              21

<210> SEQ ID NO 250
<211> LENGTH: 20
<212> TYPE: DNA
<213> ORGANISM: Artificial Sequence
<220> FEATURE:
<223> OTHER INFORMATION: Sense primer

<400> SEQUENCE: 250
tgagagtcaa cctgacgagc                                20

<210> SEQ ID NO 251
<211> LENGTH: 21
<212> TYPE: DNA
<213> ORGANISM: Artificial Sequence
<220> FEATURE:
<223> OTHER INFORMATION: Sense primer

<400> SEQUENCE: 251
gagcttactc gatagcagga g                              21

<210> SEQ ID NO 252
<211> LENGTH: 19
<212> TYPE: DNA
<213> ORGANISM: Artificial Sequence

```
<220> FEATURE:
<223> OTHER INFORMATION: Sense primer

<400> SEQUENCE: 252
tttaattcga gagggttaa                                                 19

<210> SEQ ID NO 253
<211> LENGTH: 21
<212> TYPE: DNA
<213> ORGANISM: Artificial Sequence
<220> FEATURE:
<223> OTHER INFORMATION: Sense primer

<400> SEQUENCE: 253
cttactcgat agcaggagag g                                              21

<210> SEQ ID NO 254
<211> LENGTH: 21
<212> TYPE: DNA
<213> ORGANISM: Artificial Sequence
<220> FEATURE:
<223> OTHER INFORMATION: Sense primer

<400> SEQUENCE: 254
aatcaaatct gatgtcggtg a                                              21

<210> SEQ ID NO 255
<211> LENGTH: 19
<212> TYPE: DNA
<213> ORGANISM: Artificial Sequence
<220> FEATURE:
<223> OTHER INFORMATION: Sense primer

<400> SEQUENCE: 255
ggttaaatca aatctgatg                                                 19

<210> SEQ ID NO 256
<211> LENGTH: 21
<212> TYPE: DNA
<213> ORGANISM: Artificial Sequence
<220> FEATURE:
<223> OTHER INFORMATION: Sense primer

<400> SEQUENCE: 256
ttcgagaggg ttaaatcaaa t                                              21

<210> SEQ ID NO 257
<211> LENGTH: 21
<212> TYPE: DNA
<213> ORGANISM: Artificial Sequence
<220> FEATURE:
<223> OTHER INFORMATION: Sense primer

<400> SEQUENCE: 257
caaatctgat gtcggtgagg a                                              21

<210> SEQ ID NO 258
<211> LENGTH: 19
<212> TYPE: DNA
<213> ORGANISM: Artificial Sequence
<220> FEATURE:
<223> OTHER INFORMATION: Sense primer

<400> SEQUENCE: 258
taaatcaaat ctgatgtcg                                                 19
```

```
<210> SEQ ID NO 259
<211> LENGTH: 21
<212> TYPE: DNA
<213> ORGANISM: Artificial Sequence
<220> FEATURE:
<223> OTHER INFORMATION: Sense primer

<400> SEQUENCE: 259
gagagggtta aatcaaatct g                                              21

<210> SEQ ID NO 260
<211> LENGTH: 21
<212> TYPE: DNA
<213> ORGANISM: Artificial Sequence
<220> FEATURE:
<223> OTHER INFORMATION: Sense primer

<400> SEQUENCE: 260
atctgatgtc ggtgaggagg g                                              21

<210> SEQ ID NO 261
<211> LENGTH: 19
<212> TYPE: DNA
<213> ORGANISM: Artificial Sequence
<220> FEATURE:
<223> OTHER INFORMATION: Sense primer

<400> SEQUENCE: 261
aattcgagag ggttaaatc                                                 19

<210> SEQ ID NO 262
<211> LENGTH: 19
<212> TYPE: DNA
<213> ORGANISM: Artificial Sequence
<220> FEATURE:
<223> OTHER INFORMATION: Sense primer

<400> SEQUENCE: 262
gatgtcggtg aggagggtt                                                 19

<210> SEQ ID NO 263
<211> LENGTH: 19
<212> TYPE: DNA
<213> ORGANISM: Artificial Sequence
<220> FEATURE:
<223> OTHER INFORMATION: Sense primer

<400> SEQUENCE: 263
gagggatggc agtgtcgga                                                 19

<210> SEQ ID NO 264
<211> LENGTH: 19
<212> TYPE: DNA
<213> ORGANISM: Artificial Sequence
<220> FEATURE:
<223> OTHER INFORMATION: Sense primer

<400> SEQUENCE: 264
tggccaagac ttttctcat                                                 19

<210> SEQ ID NO 265
<211> LENGTH: 20
<212> TYPE: DNA
<213> ORGANISM: Artificial Sequence
<220> FEATURE:
<223> OTHER INFORMATION: Sense primer

<400> SEQUENCE: 265
```
gatgagtctg caacctatca                                                    20

<210> SEQ ID NO 266
<211> LENGTH: 21
<212> TYPE: DNA
<213> ORGANISM: Artificial Sequence
<220> FEATURE:
<223> OTHER INFORMATION: Sense primer

<400> SEQUENCE: 266
tagcagagag gtggtgcatg g                                                  21

<210> SEQ ID NO 267
<211> LENGTH: 21
<212> TYPE: DNA
<213> ORGANISM: Artificial Sequence
<220> FEATURE:
<223> OTHER INFORMATION: Sense primer

<400> SEQUENCE: 267
acggccactg ctatcaagtt c                                                  21

<210> SEQ ID NO 268
<211> LENGTH: 20
<212> TYPE: DNA
<213> ORGANISM: Artificial Sequence
<220> FEATURE:
<223> OTHER INFORMATION: Antisense primer

<400> SEQUENCE: 268
aagctcgtca ggttgactct                                                    20

<210> SEQ ID NO 269
<211> LENGTH: 19
<212> TYPE: DNA
<213> ORGANISM: Artificial Sequence
<220> FEATURE:
<223> OTHER INFORMATION: Antisense primer

<400> SEQUENCE: 269
gtaagctcgt caggttgac                                                     19

<210> SEQ ID NO 270
<211> LENGTH: 19
<212> TYPE: DNA
<213> ORGANISM: Artificial Sequence
<220> FEATURE:
<223> OTHER INFORMATION: Antisense primer

<400> SEQUENCE: 270
cgagtaagct cgtcaggtt                                                     19

<210> SEQ ID NO 271
<211> LENGTH: 19
<212> TYPE: DNA
<213> ORGANISM: Artificial Sequence
<220> FEATURE:
<223> OTHER INFORMATION: Antisense primer

<400> SEQUENCE: 271
ctgctatcga gtaagctcg                                                     19

<210> SEQ ID NO 272
<211> LENGTH: 19
<212> TYPE: DNA
<213> ORGANISM: Artificial Sequence

```
<220> FEATURE:
<223> OTHER INFORMATION: Antisense primer

<400> SEQUENCE: 272 tttaccctc tcgaattaa                                                    19

<210> SEQ ID NO 273
<211> LENGTH: 19
<212> TYPE: DNA
<213> ORGANISM: Artificial Sequence
<220> FEATURE:
<223> OTHER INFORMATION: Antisense primer

<400> SEQUENCE: 273
ctcctgctat cgagtaagc                                                   19

<210> SEQ ID NO 274
<211> LENGTH: 20
<212> TYPE: DNA
<213> ORGANISM: Artificial Sequence
<220> FEATURE:
<223> OTHER INFORMATION: Antisense primer

<400> SEQUENCE: 274
tcagatttga tttaccctc                                                   20

<210> SEQ ID NO 275
<211> LENGTH: 20
<212> TYPE: DNA
<213> ORGANISM: Artificial Sequence
<220> FEATURE:
<223> OTHER INFORMATION: Antisense primer

<400> SEQUENCE: 275
accctcctca ccgacatcag                                                  20

<210> SEQ ID NO 276
<211> LENGTH: 19
<212> TYPE: DNA
<213> ORGANISM: Artificial Sequence
<220> FEATURE:
<223> OTHER INFORMATION: Antisense primer

<400> SEQUENCE: 276
acatcagatt tgatttaac                                                   19

<210> SEQ ID NO 277
<211> LENGTH: 19
<212> TYPE: DNA
<213> ORGANISM: Artificial Sequence
<220> FEATURE:
<223> OTHER INFORMATION: Antisense primer

<400> SEQUENCE: 277
ccgacatcag atttgattt                                                   19

<210> SEQ ID NO 278
<211> LENGTH: 19
<212> TYPE: DNA
<213> ORGANISM: Artificial Sequence
<220> FEATURE:
<223> OTHER INFORMATION: Antisense primer

<400> SEQUENCE: 278
tgatttaacc ctctcgaat                                                   19
```

<210> SEQ ID NO 279
<211> LENGTH: 19
<212> TYPE: DNA
<213> ORGANISM: Artificial Sequence
<220> FEATURE:
<223> OTHER INFORMATION: Antisense primer

<400> SEQUENCE: 279
tcaccgacat cagatttga                                              19

<210> SEQ ID NO 280
<211> LENGTH: 19
<212> TYPE: DNA
<213> ORGANISM: Artificial Sequence
<220> FEATURE:
<223> OTHER INFORMATION: Antisense primer

<400> SEQUENCE: 280
atttgattta accctctcg                                              19

<210> SEQ ID NO 281
<211> LENGTH: 21
<212> TYPE: DNA
<213> ORGANISM: Artificial Sequence
<220> FEATURE:
<223> OTHER INFORMATION: Antisense primer

<400> SEQUENCE: 281
ctacctgata ggttgcagac t                                           21

<210> SEQ ID NO 282
<211> LENGTH: 20
<212> TYPE: DNA
<213> ORGANISM: Artificial Sequence
<220> FEATURE:
<223> OTHER INFORMATION: Antisense primer

<400> SEQUENCE: 282
gcaccacctc tctgctatcg                                             20

<210> SEQ ID NO 283
<211> LENGTH: 19
<212> TYPE: DNA
<213> ORGANISM: Artificial Sequence
<220> FEATURE:
<223> OTHER INFORMATION: Antisense primer

<400> SEQUENCE: 283
atccctcaac ggaaaagca                                              19

<210> SEQ ID NO 284
<211> LENGTH: 20
<212> TYPE: DNA
<213> ORGANISM: Artificial Sequence
<220> FEATURE:
<223> OTHER INFORMATION: Antisense primer

<400> SEQUENCE: 284
acacttaaag tgaacgccct                                             20

<210> SEQ ID NO 285
<211> LENGTH: 19
<212> TYPE: DNA
<213> ORGANISM: Artificial Sequence
<220> FEATURE:
<223> OTHER INFORMATION: Antisense primer

<400> SEQUENCE: 285
tcgctccgac actgccatc                                                19

<210> SEQ ID NO 286
<211> LENGTH: 20
<212> TYPE: DNA
<213> ORGANISM: Artificial Sequence
<220> FEATURE:
<223> OTHER INFORMATION: Antisense primer

<400> SEQUENCE: 286
ccgatctcat gtcttgcagt                                               20

<210> SEQ ID NO 287
<211> LENGTH: 19
<212> TYPE: DNA
<213> ORGANISM: Artificial Sequence
<220> FEATURE:
<223> OTHER INFORMATION: Antisense primer

<400> SEQUENCE: 287
atgagaaaag tcttggcca                                                19

<210> SEQ ID NO 288
<211> LENGTH: 19
<212> TYPE: DNA
<213> ORGANISM: Artificial Sequence
<220> FEATURE:
<223> OTHER INFORMATION: Sense primer

<400> SEQUENCE: 288
agggcgttac ccctagtgc                                                19

<210> SEQ ID NO 289
<211> LENGTH: 19
<212> TYPE: DNA
<213> ORGANISM: Artificial Sequence
<220> FEATURE:
<223> OTHER INFORMATION: Sense primer

<400> SEQUENCE: 289 taccctagt gccctcgca                                                 19

<210> SEQ ID NO 290
<211> LENGTH: 21
<212> TYPE: DNA
<213> ORGANISM: Artificial Sequence
<220> FEATURE:
<223> OTHER INFORMATION: Sense primer

<400> SEQUENCE: 290
gcgcccgtag ccggcctgta a                                             21

<210> SEQ ID NO 291
<211> LENGTH: 21
<212> TYPE: DNA
<213> ORGANISM: Artificial Sequence
<220> FEATURE:
<223> OTHER INFORMATION: Sense primer

<400> SEQUENCE: 291
gagcttctcc tccgcgaggg g                                             21

<210> SEQ ID NO 292
<211> LENGTH: 21
<212> TYPE: DNA
<213> ORGANISM: Artificial Sequence

```
<220> FEATURE:
<223> OTHER INFORMATION: Sense primer

<400> SEQUENCE: 292
gcaccaggcg cggaacgtcc c                                              21

<210> SEQ ID NO 293
<211> LENGTH: 20
<212> TYPE: DNA
<213> ORGANISM: Artificial Sequence
<220> FEATURE:
<223> OTHER INFORMATION: Sense primer

<400> SEQUENCE: 293
gaggtcgagc ttctcctccg                                                20

<210> SEQ ID NO 294
<211> LENGTH: 19
<212> TYPE: DNA
<213> ORGANISM: Artificial Sequence
<220> FEATURE:
<223> OTHER INFORMATION: Sense primer

<400> SEQUENCE: 294
ccctagtgcc ctcgcaaga                                                 19

<210> SEQ ID NO 295
<211> LENGTH: 21
<212> TYPE: DNA
<213> ORGANISM: Artificial Sequence
<220> FEATURE:
<223> OTHER INFORMATION: Sense primer

<400> SEQUENCE: 295
cccgtagccg gcctgtaaag t                                              21

<210> SEQ ID NO 296
<211> LENGTH: 21
<212> TYPE: DNA
<213> ORGANISM: Artificial Sequence
<220> FEATURE:
<223> OTHER INFORMATION: Sense primer

<400> SEQUENCE: 296
cggggtggga ggtcgagctt c                                              21

<210> SEQ ID NO 297
<211> LENGTH: 20
<212> TYPE: DNA
<213> ORGANISM: Artificial Sequence
<220> FEATURE:
<223> OTHER INFORMATION: Sense primer

<400> SEQUENCE: 297
gtcgagcttc tcctccgcga                                                20

<210> SEQ ID NO 298
<211> LENGTH: 21
<212> TYPE: DNA
<213> ORGANISM: Artificial Sequence
<220> FEATURE:
<223> OTHER INFORMATION: Sense primer

<400> SEQUENCE: 298
ggtgggaggt cgagcttctc c                                              21
```

```
<210> SEQ ID NO 299
<211> LENGTH: 19
<212> TYPE: DNA
<213> ORGANISM: Artificial Sequence
<220> FEATURE:
<223> OTHER INFORMATION: Sense primer

<400> SEQUENCE: 299
tcggggtggg aggtcgagc                                               19

<210> SEQ ID NO 300
<211> LENGTH: 19
<212> TYPE: DNA
<213> ORGANISM: Artificial Sequence
<220> FEATURE:
<223> OTHER INFORMATION: Sense primer

<400> SEQUENCE: 300
gcgttacccc tagtgccct                                               19

<210> SEQ ID NO 301
<211> LENGTH: 21
<212> TYPE: DNA
<213> ORGANISM: Artificial Sequence
<220> FEATURE:
<223> OTHER INFORMATION: Sense primer

<400> SEQUENCE: 301 tagggtagg gctaagccat g                                             21

<210> SEQ ID NO 302
<211> LENGTH: 19
<212> TYPE: DNA
<213> ORGANISM: Artificial Sequence
<220> FEATURE:
<223> OTHER INFORMATION: Sense primer

<400> SEQUENCE: 302
cgcaccaggc gcggaacgt                                               19

<210> SEQ ID NO 303
<211> LENGTH: 19
<212> TYPE: DNA
<213> ORGANISM: Artificial Sequence
<220> FEATURE:
<223> OTHER INFORMATION: Sense primer

<400> SEQUENCE: 303
gggaggtcga gcttctcct                                               19

<210> SEQ ID NO 304
<211> LENGTH: 20
<212> TYPE: DNA
<213> ORGANISM: Artificial Sequence
<220> FEATURE:
<223> OTHER INFORMATION: Sense primer

<400> SEQUENCE: 304
aggtggagga ataagcgggg                                              20

<210> SEQ ID NO 305
<211> LENGTH: 19
<212> TYPE: DNA
<213> ORGANISM: Artificial Sequence
<220> FEATURE:
<223> OTHER INFORMATION: Sense primer

<400> SEQUENCE: 305
```
gaaaggtgga ggaataagc                                            19

<210> SEQ ID NO 306
<211> LENGTH: 21
<212> TYPE: DNA
<213> ORGANISM: Artificial Sequence
<220> FEATURE:
<223> OTHER INFORMATION: Sense primer

<400> SEQUENCE: 306
gggagtcgta cgctctcggg a                                         21

<210> SEQ ID NO 307
<211> LENGTH: 21
<212> TYPE: DNA
<213> ORGANISM: Artificial Sequence
<220> FEATURE:
<223> OTHER INFORMATION: Sense primer

<400> SEQUENCE: 307
ctaacctgcc cttgggatct g                                         21

<210> SEQ ID NO 308
<211> LENGTH: 19
<212> TYPE: DNA
<213> ORGANISM: Artificial Sequence
<220> FEATURE:
<223> OTHER INFORMATION: Antisense primer

<400> SEQUENCE: 308
ggcactaggg gtaacgccc                                            19

<210> SEQ ID NO 309
<211> LENGTH: 20
<212> TYPE: DNA
<213> ORGANISM: Artificial Sequence
<220> FEATURE:
<223> OTHER INFORMATION: Antisense primer

<400> SEQUENCE: 309
agaagctcga cctcccaccc                                           20

<210> SEQ ID NO 310
<211> LENGTH: 20
<212> TYPE: DNA
<213> ORGANISM: Artificial Sequence
<220> FEATURE:
<223> OTHER INFORMATION: Antisense primer

<400> SEQUENCE: 310
tacaggccgg ctacgggcgc                                           20

<210> SEQ ID NO 311
<211> LENGTH: 19
<212> TYPE: DNA
<213> ORGANISM: Artificial Sequence
<220> FEATURE:
<223> OTHER INFORMATION: Antisense primer

<400> SEQUENCE: 311
agctcgacct cccaccccg                                            19

<210> SEQ ID NO 312
<211> LENGTH: 19
<212> TYPE: DNA
<213> ORGANISM: Artificial Sequence

```
<220> FEATURE:
<223> OTHER INFORMATION: Antisense primer

<400> SEQUENCE: 312
cccctcgcgg aggagaagc                                               19

<210> SEQ ID NO 313
<211> LENGTH: 19
<212> TYPE: DNA
<213> ORGANISM: Artificial Sequence
<220> FEATURE:
<223> OTHER INFORMATION: Antisense primer

<400> SEQUENCE: 313
tgcgagggca ctagggta                                                19

<210> SEQ ID NO 314
<211> LENGTH: 21
<212> TYPE: DNA
<213> ORGANISM: Artificial Sequence
<220> FEATURE:
<223> OTHER INFORMATION: Antisense primer

<400> SEQUENCE: 314
tgactttaca ggccggctac g                                            21

<210> SEQ ID NO 315
<211> LENGTH: 21
<212> TYPE: DNA
<213> ORGANISM: Artificial Sequence
<220> FEATURE:
<223> OTHER INFORMATION: Antisense primer

<400> SEQUENCE: 315
catggcttag ccctacccct a                                            21

<210> SEQ ID NO 316
<211> LENGTH: 20
<212> TYPE: DNA
<213> ORGANISM: Artificial Sequence
<220> FEATURE:
<223> OTHER INFORMATION: Antisense primer

<400> SEQUENCE: 316
aggagaagct cgacctccca                                              20

<210> SEQ ID NO 317
<211> LENGTH: 19
<212> TYPE: DNA
<213> ORGANISM: Artificial Sequence
<220> FEATURE:
<223> OTHER INFORMATION: Antisense primer

<400> SEQUENCE: 317
gacgttccgc gcctggtgc                                               19

<210> SEQ ID NO 318
<211> LENGTH: 20
<212> TYPE: DNA
<213> ORGANISM: Artificial Sequence
<220> FEATURE:
<223> OTHER INFORMATION: Antisense primer

<400> SEQUENCE: 318
ctttacaggc cggctacggg                                              20
```

```
<210> SEQ ID NO 319
<211> LENGTH: 19
<212> TYPE: DNA
<213> ORGANISM: Artificial Sequence
<220> FEATURE:
<223> OTHER INFORMATION: Antisense primer

<400> SEQUENCE: 319
tcttgcgagg gcactaggg                                                  19

<210> SEQ ID NO 320
<211> LENGTH: 20
<212> TYPE: DNA
<213> ORGANISM: Artificial Sequence
<220> FEATURE:
<223> OTHER INFORMATION: Antisense primer

<400> SEQUENCE: 320
cggaggagaa gctcgacctc                                                 20

<210> SEQ ID NO 321
<211> LENGTH: 20
<212> TYPE: DNA
<213> ORGANISM: Artificial Sequence
<220> FEATURE:
<223> OTHER INFORMATION: Antisense primer

<400> SEQUENCE: 321
tcgcggagga gaagctcgac                                                 20

<210> SEQ ID NO 322
<211> LENGTH: 19
<212> TYPE: DNA
<213> ORGANISM: Artificial Sequence
<220> FEATURE:
<223> OTHER INFORMATION: Antisense primer

<400> SEQUENCE: 322
gagggcacta ggggtaacg                                                  19

<210> SEQ ID NO 323
<211> LENGTH: 20
<212> TYPE: DNA
<213> ORGANISM: Artificial Sequence
<220> FEATURE:
<223> OTHER INFORMATION: Antisense primer

<400> SEQUENCE: 323
accccgaggg gcaagaggcc                                                 20

<210> SEQ ID NO 324
<211> LENGTH: 21
<212> TYPE: DNA
<213> ORGANISM: Artificial Sequence
<220> FEATURE:
<223> OTHER INFORMATION: Antisense primer

<400> SEQUENCE: 324
ggggttatcc agatcccaag g                                               21

<210> SEQ ID NO 325
<211> LENGTH: 20
<212> TYPE: DNA
<213> ORGANISM: Artificial Sequence
<220> FEATURE:
<223> OTHER INFORMATION: Antisense primer

<400> SEQUENCE: 325
```
gccacgccct cttcccgaga                                               20

<210> SEQ ID NO 326
<211> LENGTH: 20
<212> TYPE: DNA
<213> ORGANISM: Artificial Sequence
<220> FEATURE:
<223> OTHER INFORMATION: Antisense primer

<400> SEQUENCE: 326
gttatccaga tcccaagggc                                               20

<210> SEQ ID NO 327
<211> LENGTH: 21
<212> TYPE: DNA
<213> ORGANISM: Artificial Sequence
<220> FEATURE:
<223> OTHER INFORMATION: Antisense primer

<400> SEQUENCE: 327
cttattcctc cacctttctg g                                             21

<210> SEQ ID NO 328
<211> LENGTH: 19
<212> TYPE: DNA
<213> ORGANISM: Artificial Sequence
<220> FEATURE:
<223> OTHER INFORMATION: Sense primer

<400> SEQUENCE: 328
taaaccctgc cgcagttgg                                                19

<210> SEQ ID NO 329
<211> LENGTH: 19
<212> TYPE: DNA
<213> ORGANISM: Artificial Sequence
<220> FEATURE:
<223> OTHER INFORMATION: Sense primer

<400> SEQUENCE: 329
ccttaaaccc tgccgcagt                                                19

<210> SEQ ID NO 330
<211> LENGTH: 19
<212> TYPE: DNA
<213> ORGANISM: Artificial Sequence
<220> FEATURE:
<223> OTHER INFORMATION: Sense primer

<400> SEQUENCE: 330
gtcctggaac ggttcctcg                                                19

<210> SEQ ID NO 331
<211> LENGTH: 21
<212> TYPE: DNA
<213> ORGANISM: Artificial Sequence
<220> FEATURE:
<223> OTHER INFORMATION: Sense primer

<400> SEQUENCE: 331
ctctacaaag gcgggggaat a                                             21

<210> SEQ ID NO 332
<211> LENGTH: 20
<212> TYPE: DNA
<213> ORGANISM: Artificial Sequence
<220> FEATURE:
<223> OTHER INFORMATION: Sense primer

<400> SEQUENCE: 332
ctggaacggt tcctcgctga                                             20

<210> SEQ ID NO 333
<211> LENGTH: 21
<212> TYPE: DNA
<213> ORGANISM: Artificial Sequence
<220> FEATURE:
<223> OTHER INFORMATION: Sense primer

<400> SEQUENCE: 333
ggcgaggagt cctggaacgg t                                           21

<210> SEQ ID NO 334
<211> LENGTH: 19
<212> TYPE: DNA
<213> ORGANISM: Artificial Sequence
<220> FEATURE:
<223> OTHER INFORMATION: Sense primer

<400> SEQUENCE: 334
tttccccgct ctacaaagg                                              19

<210> SEQ ID NO 335
<211> LENGTH: 21
<212> TYPE: DNA
<213> ORGANISM: Artificial Sequence
<220> FEATURE:
<223> OTHER INFORMATION: Sense primer

<400> SEQUENCE: 335
tacaaaggcg ggggaataag c                                           21

<210> SEQ ID NO 336
<211> LENGTH: 19
<212> TYPE: DNA
<213> ORGANISM: Artificial Sequence
<220> FEATURE:
<223> OTHER INFORMATION: Sense primer

<400> SEQUENCE: 336
cgctctacaa aggcgggggg                                             19

<210> SEQ ID NO 337
<211> LENGTH: 20
<212> TYPE: DNA
<213> ORGANISM: Artificial Sequence
<220> FEATURE:
<223> OTHER INFORMATION: Sense primer

<400> SEQUENCE: 337
ataggcgagg agtcctggaa                                             20

<210> SEQ ID NO 338
<211> LENGTH: 19
<212> TYPE: DNA
<213> ORGANISM: Artificial Sequence
<220> FEATURE:
<223> OTHER INFORMATION: Sense primer

<400> SEQUENCE: 338
ccataggcga ggagtcctg                                              19

```
<210> SEQ ID NO 339
<211> LENGTH: 19
<212> TYPE: DNA
<213> ORGANISM: Artificial Sequence
<220> FEATURE:
<223> OTHER INFORMATION: Sense primer

<400> SEQUENCE: 339
gcttttcccc gctctacaa                                               19

<210> SEQ ID NO 340
<211> LENGTH: 20
<212> TYPE: DNA
<213> ORGANISM: Artificial Sequence
<220> FEATURE:
<223> OTHER INFORMATION: Sense primer

<400> SEQUENCE: 340
gctaacctac cctgaggagg                                              20

<210> SEQ ID NO 341
<211> LENGTH: 20
<212> TYPE: DNA
<213> ORGANISM: Artificial Sequence
<220> FEATURE:
<223> OTHER INFORMATION: Sense primer

<400> SEQUENCE: 341
tctcccatag gcgaggagtc                                              20

<210> SEQ ID NO 342
<211> LENGTH: 19
<212> TYPE: DNA
<213> ORGANISM: Artificial Sequence
<220> FEATURE:
<223> OTHER INFORMATION: Sense primer

<400> SEQUENCE: 342
tggctaacct accctgagg                                               19

<210> SEQ ID NO 343
<211> LENGTH: 19
<212> TYPE: DNA
<213> ORGANISM: Artificial Sequence
<220> FEATURE:
<223> OTHER INFORMATION: Sense primer

<400> SEQUENCE: 343
ataatctccc ataggcgag                                               19

<210> SEQ ID NO 344
<211> LENGTH: 20
<212> TYPE: DNA
<213> ORGANISM: Artificial Sequence
<220> FEATURE:
<223> OTHER INFORMATION: Sense primer

<400> SEQUENCE: 344
tgaggaggga gataacccccg                                             20

<210> SEQ ID NO 345
<211> LENGTH: 21
<212> TYPE: DNA
<213> ORGANISM: Artificial Sequence
<220> FEATURE:
<223> OTHER INFORMATION: Sense primer

<400> SEQUENCE: 345
```

```
acacgtggct aacctaccct g                                              21

<210> SEQ ID NO 346
<211> LENGTH: 19
<212> TYPE: DNA
<213> ORGANISM: Artificial Sequence
<220> FEATURE:
<223> OTHER INFORMATION: Sense primer

<400> SEQUENCE: 346
cctgaggagg gagataacc                                                 19

<210> SEQ ID NO 347
<211> LENGTH: 19
<212> TYPE: DNA
<213> ORGANISM: Artificial Sequence
<220> FEATURE:
<223> OTHER INFORMATION: Sense primer

<400> SEQUENCE: 347
aaactgggga taatctccc                                                 19

<210> SEQ ID NO 348
<211> LENGTH: 19
<212> TYPE: DNA
<213> ORGANISM: Artificial Sequence
<220> FEATURE:
<223> OTHER INFORMATION: Antisense primer

<400> SEQUENCE: 348
ccaactgcgg cagggttta                                                 19

<210> SEQ ID NO 349
<211> LENGTH: 19
<212> TYPE: DNA
<213> ORGANISM: Artificial Sequence
<220> FEATURE:
<223> OTHER INFORMATION: Antisense primer

<400> SEQUENCE: 349
actgcggcag ggtttaagg                                                 19

<210> SEQ ID NO 350
<211> LENGTH: 21
<212> TYPE: DNA
<213> ORGANISM: Artificial Sequence
<220> FEATURE:
<223> OTHER INFORMATION: Antisense primer

<400> SEQUENCE: 350
cgaggaaccg ttccaggact c                                              21

<210> SEQ ID NO 351
<211> LENGTH: 20
<212> TYPE: DNA
<213> ORGANISM: Artificial Sequence
<220> FEATURE:
<223> OTHER INFORMATION: Antisense primer

<400> SEQUENCE: 351
aaccgttcca ggactcctcg                                                20

<210> SEQ ID NO 352
<211> LENGTH: 21
<212> TYPE: DNA
<213> ORGANISM: Artificial Sequence
```

```
<220> FEATURE:
<223> OTHER INFORMATION: Antisense primer

<400> SEQUENCE: 352
tccaggactc ctcgcctatg g                                              21

<210> SEQ ID NO 353
<211> LENGTH: 19
<212> TYPE: DNA
<213> ORGANISM: Artificial Sequence
<220> FEATURE:
<223> OTHER INFORMATION: Antisense primer

<400> SEQUENCE: 353
cctttgtaga gcggggaaa                                                 19

<210> SEQ ID NO 354
<211> LENGTH: 20
<212> TYPE: DNA
<213> ORGANISM: Artificial Sequence
<220> FEATURE:
<223> OTHER INFORMATION: Antisense primer

<400> SEQUENCE: 354
agcgaggaac cgttccagga                                                20

<210> SEQ ID NO 355
<211> LENGTH: 21
<212> TYPE: DNA
<213> ORGANISM: Artificial Sequence
<220> FEATURE:
<223> OTHER INFORMATION: Antisense primer

<400> SEQUENCE: 355
cgttccagga ctcctcgcct a                                              21

<210> SEQ ID NO 356
<211> LENGTH: 19
<212> TYPE: DNA
<213> ORGANISM: Artificial Sequence
<220> FEATURE:
<223> OTHER INFORMATION: Antisense primer

<400> SEQUENCE: 356
cccccgcctt tgtagagcg                                                 19

<210> SEQ ID NO 357
<211> LENGTH: 20
<212> TYPE: DNA
<213> ORGANISM: Artificial Sequence
<220> FEATURE:
<223> OTHER INFORMATION: Antisense primer

<400> SEQUENCE: 357
ttcagcgagg aaccgttcca                                                20

<210> SEQ ID NO 358
<211> LENGTH: 19
<212> TYPE: DNA
<213> ORGANISM: Artificial Sequence
<220> FEATURE:
<223> OTHER INFORMATION: Antisense primer

<400> SEQUENCE: 358
attcccccgc ctttgtaga                                                 19
```

```
<210> SEQ ID NO 359
<211> LENGTH: 19
<212> TYPE: DNA
<213> ORGANISM: Artificial Sequence
<220> FEATURE:
<223> OTHER INFORMATION: Antisense primer

<400> SEQUENCE: 359
ttgtagagcg gggaaaagc                                                 19

<210> SEQ ID NO 360
<211> LENGTH: 21
<212> TYPE: DNA
<213> ORGANISM: Artificial Sequence
<220> FEATURE:
<223> OTHER INFORMATION: Antisense primer

<400> SEQUENCE: 360
atctccctcc tcagggtagg t                                              21

<210> SEQ ID NO 361
<211> LENGTH: 19
<212> TYPE: DNA
<213> ORGANISM: Artificial Sequence
<220> FEATURE:
<223> OTHER INFORMATION: Antisense primer

<400> SEQUENCE: 361
gggttatctc cctcctcag                                                 19

<210> SEQ ID NO 362
<211> LENGTH: 19
<212> TYPE: DNA
<213> ORGANISM: Artificial Sequence
<220> FEATURE:
<223> OTHER INFORMATION: Antisense primer

<400> SEQUENCE: 362
tcgcctatgg gagattatc                                                 19

<210> SEQ ID NO 363
<211> LENGTH: 20
<212> TYPE: DNA
<213> ORGANISM: Artificial Sequence
<220> FEATURE:
<223> OTHER INFORMATION: Antisense primer

<400> SEQUENCE: 363
tcagggtagg ttagccacgt                                                20

<210> SEQ ID NO 364
<211> LENGTH: 19
<212> TYPE: DNA
<213> ORGANISM: Artificial Sequence
<220> FEATURE:
<223> OTHER INFORMATION: Antisense primer

<400> SEQUENCE: 364
cctcagggta ggttagcca                                                 19

<210> SEQ ID NO 365
<211> LENGTH: 19
<212> TYPE: DNA
<213> ORGANISM: Artificial Sequence
<220> FEATURE:
<223> OTHER INFORMATION: Antisense primer

<400> SEQUENCE: 365
```

```
ccggggttat ctccctcct                                                  19

<210> SEQ ID NO 366
<211> LENGTH: 19
<212> TYPE: DNA
<213> ORGANISM: Artificial Sequence
<220> FEATURE:
<223> OTHER INFORMATION: Antisense primer

<400> SEQUENCE: 366
tcctcgccta tgggagatt                                                  19

<210> SEQ ID NO 367
<211> LENGTH: 19
<212> TYPE: DNA
<213> ORGANISM: Artificial Sequence
<220> FEATURE:
<223> OTHER INFORMATION: Antisense primer

<400> SEQUENCE: 367
cctcctcagg gtaggttag                                                  19

<210> SEQ ID NO 368
<211> LENGTH: 20
<212> TYPE: DNA
<213> ORGANISM: Artificial Sequence
<220> FEATURE:
<223> OTHER INFORMATION: Sense primer

<400> SEQUENCE: 368
tcctgaaagg acgaccggtg                                                 20

<210> SEQ ID NO 369
<211> LENGTH: 19
<212> TYPE: DNA
<213> ORGANISM: Artificial Sequence
<220> FEATURE:
<223> OTHER INFORMATION: Sense primer

<400> SEQUENCE: 369
ggactgaggg ctgtaactc                                                  19

<210> SEQ ID NO 370
<211> LENGTH: 21
<212> TYPE: DNA
<213> ORGANISM: Artificial Sequence
<220> FEATURE:
<223> OTHER INFORMATION: Sense primer

<400> SEQUENCE: 370
gaggttgaat gtactttcag g                                               21

<210> SEQ ID NO 371
<211> LENGTH: 20
<212> TYPE: DNA
<213> ORGANISM: Artificial Sequence
<220> FEATURE:
<223> OTHER INFORMATION: Sense primer

<400> SEQUENCE: 371
ggtggcgaaa gcgttcaact                                                 20

<210> SEQ ID NO 372
<211> LENGTH: 19
<212> TYPE: DNA
<213> ORGANISM: Artificial Sequence
```

```
<220> FEATURE:
<223> OTHER INFORMATION: Sense primer

<400> SEQUENCE: 372
gccctcacga atgtggatt                                                   19

<210> SEQ ID NO 373
<211> LENGTH: 20
<212> TYPE: DNA
<213> ORGANISM: Artificial Sequence
<220> FEATURE:
<223> OTHER INFORMATION: Sense primer

<400> SEQUENCE: 373
acctcgaaac ccgttcgtag                                                  20

<210> SEQ ID NO 374
<211> LENGTH: 19
<212> TYPE: DNA
<213> ORGANISM: Artificial Sequence
<220> FEATURE:
<223> OTHER INFORMATION: Sense primer

<400> SEQUENCE: 374
tccgtagtaa tcgtaggtc                                                   19

<210> SEQ ID NO 375
<211> LENGTH: 21
<212> TYPE: DNA
<213> ORGANISM: Artificial Sequence
<220> FEATURE:
<223> OTHER INFORMATION: Sense primer

<400> SEQUENCE: 375
atcctgtaat cctgaaagga c                                                21

<210> SEQ ID NO 376
<211> LENGTH: 20
<212> TYPE: DNA
<213> ORGANISM: Artificial Sequence
<220> FEATURE:
<223> OTHER INFORMATION: Sense primer

<400> SEQUENCE: 376
gtagtcagga ctgagggctg                                                  20

<210> SEQ ID NO 377
<211> LENGTH: 21
<212> TYPE: DNA
<213> ORGANISM: Artificial Sequence
<220> FEATURE:
<223> OTHER INFORMATION: Sense primer

<400> SEQUENCE: 377
aggacgaccg gtggcgaaag c                                                21

<210> SEQ ID NO 378
<211> LENGTH: 20
<212> TYPE: DNA
<213> ORGANISM: Artificial Sequence
<220> FEATURE:
<223> OTHER INFORMATION: Sense primer

<400> SEQUENCE: 378
taactcgccc tcacgaatgt                                                  20
```

```
<210> SEQ ID NO 379
<211> LENGTH: 19
<212> TYPE: DNA
<213> ORGANISM: Artificial Sequence
<220> FEATURE:
<223> OTHER INFORMATION: Sense primer

<400> SEQUENCE: 379
gaaggtgtta agtgggtca                                                  19

<210> SEQ ID NO 380
<211> LENGTH: 21
<212> TYPE: DNA
<213> ORGANISM: Artificial Sequence
<220> FEATURE:
<223> OTHER INFORMATION: Sense primer

<400> SEQUENCE: 380
aaacccgttc gtagtcagga c                                               21

<210> SEQ ID NO 381
<211> LENGTH: 20
<212> TYPE: DNA
<213> ORGANISM: Artificial Sequence
<220> FEATURE:
<223> OTHER INFORMATION: Sense primer

<400> SEQUENCE: 381
tacggtgaat atgcccctgc                                                 20

<210> SEQ ID NO 382
<211> LENGTH: 21
<212> TYPE: DNA
<213> ORGANISM: Artificial Sequence
<220> FEATURE:
<223> OTHER INFORMATION: Sense primer

<400> SEQUENCE: 382
cacttggtgt tgcttctccg t                                               21

<210> SEQ ID NO 383
<211> LENGTH: 19
<212> TYPE: DNA
<213> ORGANISM: Artificial Sequence
<220> FEATURE:
<223> OTHER INFORMATION: Sense primer

<400> SEQUENCE: 383
gatcactttt attgagtct                                                  19

<210> SEQ ID NO 384
<211> LENGTH: 20
<212> TYPE: DNA
<213> ORGANISM: Artificial Sequence
<220> FEATURE:
<223> OTHER INFORMATION: Sense primer

<400> SEQUENCE: 384
agcatcagga ataaggactg                                                 20

<210> SEQ ID NO 385
<211> LENGTH: 19
<212> TYPE: DNA
<213> ORGANISM: Artificial Sequence
<220> FEATURE:
<223> OTHER INFORMATION: Sense primer

<400> SEQUENCE: 385
``` aagacccca tctctaatt                                        19

<210> SEQ ID NO 386
<211> LENGTH: 19
<212> TYPE: DNA
<213> ORGANISM: Artificial Sequence
<220> FEATURE:
<223> OTHER INFORMATION: Sense primer

<400> SEQUENCE: 386
ccggtcttat aaatcttca                                       19

<210> SEQ ID NO 387
<211> LENGTH: 20
<212> TYPE: DNA
<213> ORGANISM: Artificial Sequence
<220> FEATURE:
<223> OTHER INFORMATION: Sense primer

<400> SEQUENCE: 387
ataacgagca agacccccat                                      20

<210> SEQ ID NO 388
<211> LENGTH: 20
<212> TYPE: DNA
<213> ORGANISM: Artificial Sequence
<220> FEATURE:
<223> OTHER INFORMATION: Antisense primer

<400> SEQUENCE: 388 cagggcata ttcaccgtag                                       20

<210> SEQ ID NO 389
<211> LENGTH: 19
<212> TYPE: DNA
<213> ORGANISM: Artificial Sequence
<220> FEATURE:
<223> OTHER INFORMATION: Antisense primer

<400> SEQUENCE: 389
tcaggattac aggatttta                                       19

<210> SEQ ID NO 390
<211> LENGTH: 21
<212> TYPE: DNA
<213> ORGANISM: Artificial Sequence
<220> FEATURE:
<223> OTHER INFORMATION: Antisense primer

<400> SEQUENCE: 390
accctgaaag tacattcaac c                                    21

<210> SEQ ID NO 391
<211> LENGTH: 19
<212> TYPE: DNA
<213> ORGANISM: Artificial Sequence
<220> FEATURE:
<223> OTHER INFORMATION: Antisense primer

<400> SEQUENCE: 391
gccaccggtc gtcctttca                                       19

<210> SEQ ID NO 392
<211> LENGTH: 19
<212> TYPE: DNA
<213> ORGANISM: Artificial Sequence

```
<220> FEATURE:
<223> OTHER INFORMATION: Antisense primer

<400> SEQUENCE: 392
ctagttgaac gctttcgcc                                              19

<210> SEQ ID NO 393
<211> LENGTH: 21
<212> TYPE: DNA
<213> ORGANISM: Artificial Sequence
<220> FEATURE:
<223> OTHER INFORMATION: Antisense primer

<400> SEQUENCE: 393
tcgtcctttc aggattacag g                                           21

<210> SEQ ID NO 394
<211> LENGTH: 21
<212> TYPE: DNA
<213> ORGANISM: Artificial Sequence
<220> FEATURE:
<223> OTHER INFORMATION: Antisense primer

<400> SEQUENCE: 394
acgctttcgc caccggtcgt c                                           21

<210> SEQ ID NO 395
<211> LENGTH: 19
<212> TYPE: DNA
<213> ORGANISM: Artificial Sequence
<220> FEATURE:
<223> OTHER INFORMATION: Antisense primer

<400> SEQUENCE: 395
gggtttcgag gttagcttc                                              19

<210> SEQ ID NO 396
<211> LENGTH: 19
<212> TYPE: DNA
<213> ORGANISM: Artificial Sequence
<220> FEATURE:
<223> OTHER INFORMATION: Antisense primer

<400> SEQUENCE: 396
ccctcagtcc tgactacga                                              19

<210> SEQ ID NO 397
<211> LENGTH: 20
<212> TYPE: DNA
<213> ORGANISM: Artificial Sequence
<220> FEATURE:
<223> OTHER INFORMATION: Antisense primer

<400> SEQUENCE: 397
ctgaagattt ataagaccgg                                             20

<210> SEQ ID NO 398
<211> LENGTH: 21
<212> TYPE: DNA
<213> ORGANISM: Artificial Sequence
<220> FEATURE:
<223> OTHER INFORMATION: Antisense primer

<400> SEQUENCE: 398
ttacagccct cagtcctgac t                                           21
```

```
<210> SEQ ID NO 399
<211> LENGTH: 21
<212> TYPE: DNA
<213> ORGANISM: Artificial Sequence
<220> FEATURE:
<223> OTHER INFORMATION: Antisense primer

<400> SEQUENCE: 399
aatccacatt cgtgagggcg a                                           21

<210> SEQ ID NO 400
<211> LENGTH: 20
<212> TYPE: DNA
<213> ORGANISM: Artificial Sequence
<220> FEATURE:
<223> OTHER INFORMATION: Antisense primer

<400> SEQUENCE: 400
atgggggtct tgctcgttat                                             20

<210> SEQ ID NO 401
<211> LENGTH: 19
<212> TYPE: DNA
<213> ORGANISM: Artificial Sequence
<220> FEATURE:
<223> OTHER INFORMATION: Antisense primer

<400> SEQUENCE: 401
gctgttgacc tacgattac                                              19

<210> SEQ ID NO 402
<211> LENGTH: 21
<212> TYPE: DNA
<213> ORGANISM: Artificial Sequence
<220> FEATURE:
<223> OTHER INFORMATION: Antisense primer

<400> SEQUENCE: 402
cctacgatta ctacggaatc c                                           21

<210> SEQ ID NO 403
<211> LENGTH: 19
<212> TYPE: DNA
<213> ORGANISM: Artificial Sequence
<220> FEATURE:
<223> OTHER INFORMATION: Antisense primer

<400> SEQUENCE: 403
acccacttaa caccttcgc                                              19

<210> SEQ ID NO 404
<211> LENGTH: 20
<212> TYPE: DNA
<213> ORGANISM: Artificial Sequence
<220> FEATURE:
<223> OTHER INFORMATION: Antisense primer

<400> SEQUENCE: 404
cccaagtctt acagtctctt                                             20

<210> SEQ ID NO 405
<211> LENGTH: 20
<212> TYPE: DNA
<213> ORGANISM: Artificial Sequence
<220> FEATURE:
<223> OTHER INFORMATION: Antisense primer

<400> SEQUENCE: 405
```

```
ctaccctgaa agtacattca                                          20

<210> SEQ ID NO 406
<211> LENGTH: 19
<212> TYPE: DNA
<213> ORGANISM: Artificial Sequence
<220> FEATURE:
<223> OTHER INFORMATION: Antisense primer

<400> SEQUENCE: 406
cagcccttat tcctgatgc                                           19

<210> SEQ ID NO 407
<211> LENGTH: 20
<212> TYPE: DNA
<213> ORGANISM: Artificial Sequence
<220> FEATURE:
<223> OTHER INFORMATION: Antisense primer

<400> SEQUENCE: 407
ggtcgtcctt tcaggattac                                          20

<210> SEQ ID NO 408
<211> LENGTH: 18
<212> TYPE: DNA
<213> ORGANISM: Artificial Sequence
<220> FEATURE:
<223> OTHER INFORMATION: PCR primer

<400> SEQUENCE: 408
gtgccagcmg ccgcggta                                            18

<210> SEQ ID NO 409
<211> LENGTH: 17
<212> TYPE: DNA
<213> ORGANISM: Artificial Sequence
<220> FEATURE:
<223> OTHER INFORMATION: PCR primer

<400> SEQUENCE: 409
cctacgggag gcagcag                                             17

<210> SEQ ID NO 410
<211> LENGTH: 19
<212> TYPE: DNA
<213> ORGANISM: Artificial Sequence
<220> FEATURE:
<223> OTHER INFORMATION: PCR primer

<400> SEQUENCE: 410
ccgtcaattc ctttgagtt                                           19

<210> SEQ ID NO 411
<211> LENGTH: 18
<212> TYPE: DNA
<213> ORGANISM: Artificial Sequence
<220> FEATURE:
<223> OTHER INFORMATION: PCR primer

<400> SEQUENCE: 411
gctgcctccc gtaggagt                                            18

<210> SEQ ID NO 412
<211> LENGTH: 18
<212> TYPE: DNA
<213> ORGANISM: Artificial Sequence
```

```
<220> FEATURE:
<223> OTHER INFORMATION: PCR primer

<400> SEQUENCE: 412
gggcggwgtg tacaaggc                                                 18

<210> SEQ ID NO 413
<211> LENGTH: 20
<212> TYPE: DNA
<213> ORGANISM: Artificial Sequence
<220> FEATURE:
<223> OTHER INFORMATION: PCR primer

<400> SEQUENCE: 413
acggggcgca gcaggcgcga                                               20

<210> SEQ ID NO 414
<211> LENGTH: 19
<212> TYPE: DNA
<213> ORGANISM: Artificial Sequence
<220> FEATURE:
<223> OTHER INFORMATION: PCR primer

<400> SEQUENCE: 414
gtgccagcag ccgcggtaa                                                19

<210> SEQ ID NO 415
<211> LENGTH: 19
<212> TYPE: DNA
<213> ORGANISM: Artificial Sequence
<220> FEATURE:
<223> OTHER INFORMATION: PCR primer

<400> SEQUENCE: 415
yccggcgttg amtccaatt                                                19

<210> SEQ ID NO 416
<211> LENGTH: 20
<212> TYPE: DNA
<213> ORGANISM: Artificial Sequence
<220> FEATURE:
<223> OTHER INFORMATION: PCR primer

<400> SEQUENCE: 416
gtgctccccc gccaattcct                                               20

<210> SEQ ID NO 417
<211> LENGTH: 17
<212> TYPE: DNA
<213> ORGANISM: Artificial Sequence
<220> FEATURE:
<223> OTHER INFORMATION: PCR primer

<400> SEQUENCE: 417
attaccgcgg ctgctgg                                                  17
```